(12) United States Patent
Phanstiel, IV et al.

(10) Patent No.: US 12,365,659 B2
(45) Date of Patent: Jul. 22, 2025

(54) NON-POLYAMINE BASED POLYAMINE TRANSPORT INHIBITORS AND THEIR USE IN THE TREATMENT OF HUMAN CANCERS

(71) Applicants: UNIVERSITY OF CENTRAL FLORIDA RESEARCH FOUNDATION, INC., Orlando, FL (US); SANFORD BURNHAM PREBYS MEDICAL DISCOVERY INSTITUTE, La Jolla, CA (US)

(72) Inventors: Otto Phanstiel, IV, Oviedo, FL (US); Holly Moots, Cape Canaveral, FL (US); Patrick Maloney, Orlando, FL (US); Paul Hershberger, Orlando, FL (US); Satyamaheshwar Peddibhotla, Orlando, FL (US)

(73) Assignees: UNIVERSITY OF CENTRAL FLORIDA RESEARCH FOUNDATION, INC., Orlando, FL (US); SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 0 days.

(21) Appl. No.: 18/413,352

(22) Filed: Jan. 16, 2024

(65) Prior Publication Data
US 2024/0166614 A1 May 23, 2024

Related U.S. Application Data

(62) Division of application No. 17/267,649, filed as application No. PCT/US2019/046122 on Aug. 12, 2019, now Pat. No. 11,905,268.

(60) Provisional application No. 62/717,754, filed on Aug. 10, 2018.

(51) Int. Cl.
| C07D 295/155 | (2006.01) |
| A61K 45/06 | (2006.01) |
| C07D 211/46 | (2006.01) |

(52) U.S. Cl.
CPC .......... *C07D 295/155* (2013.01); *A61K 45/06* (2013.01); *C07D 211/46* (2013.01)

(58) Field of Classification Search
None
See application file for complete search history.

(56) References Cited

U.S. PATENT DOCUMENTS

| 6,172,261 B1 | 1/2001 | Vermeulin et al. |
| 6,872,852 B2 | 3/2005 | Burns |
| 6,949,679 B1 | 9/2005 | Poulin et al. |
| 8,497,398 B1 | 7/2013 | Phanstiel, IV et al. |
| 9,212,131 B2 | 12/2015 | Phanstiel et al. |
| 9,598,351 B2 | 3/2017 | Phanstiel, IV |
| 9,730,902 B2 | 8/2017 | Phanstiel, IV et al. |
| 2014/0057989 A1 | 2/2014 | Phanstiel, IV |
| 2016/0311756 A1 | 10/2016 | Phanstiel, IV et al. |

FOREIGN PATENT DOCUMENTS

| WO | 2004018428 A1 | 3/2004 |
| WO | 2010103278 A1 | 9/2010 |
| WO | 2019121661 A1 | 6/2019 |
| WO | 2020033944 A2 | 2/2020 |
| WO | 2020033944 A3 | 2/2020 |

OTHER PUBLICATIONS

CAS 959501-13-4 (entered into STN on Dec. 26, 2007) (Year: 2007).*
Rotas, Georgios et al., "Synthesis of 5-alkyl(or aryl)pryrolo[1,2-a]quinoxzlin-4(5H)-ones by denitrocyclisation of N-alkyl (or aryl)-1-(2-nitrophenyl)-1H-pyrrole-2carboxamides. Evidence of a smiles rearrangement", Tetrahedron 60 (2004) 10825-10832.
PCT/US19/46122, PCT Search Report & Written Opinion, mailed Jan. 31, 2020, 10 pages.
Alexander, Eric T. et al., "A novel polyamine blockade therapy activates an anti-tumor immune response" Oncotarget, 2017, vol. 8, No. 48, pp. 84140-84152.
Burns, Mark R. et al., "Lipophilic Lysine-Spermine Conjugates Are Potent Polyamine Transport Inhibitors for Use in Combination with a Polyamine Biosynthesis Inhibitor", J. Med. Chem., 2009, vol. 52, pp. 1983-1993.
Burns, Mark R. et al., "Amino Acid/Spermine Conjugates: Polyamine Amides as Potent Spermidine Uptake Inhibitors", J. Med. Chem., 2001, vol. 44, pp. 3632-3644.
Chen, Yan et al., "Combination therapy with 2-difluoromethylornithine and a polyamine transport inhibitor against murine squamous cell carcinoma", Int. J. Cancer, 2006, vol. 118, pp. 2344-2349.
Gardner, Richard Andrew et al., "N1-Substituent Effects in the Selective Delivery of Polyamine Conjugates into Cells Containing Active Polyamine Transporters", J. Med. Chem., 2004, vol. 47, pp. 6055-6069.
Gitto, Sarah B. et al., "Difluoromethylornithine Combined with a Polyamine Transport Inhibitor Is Effective against Gemcitabine Resistant Pancreatic Cancer", Mol. Pharmaceutics, 2018, vol. 15, pp. 369-376.
Graminski, Gerard F. et al., "Synthesis of Bis-Spermine Dimers that are Potent Polyamine Transport Inhibitors", Bioorganic & Medicinal Chemistry Letters, 2002, vol. 12, pp. 35-40.
Hayes, Candace S. et al., "Polyamine blockade promotes antitumor immunity" OncoImmunology, 2014, vol. 3, No. 1, e27360-e27360-02.

(Continued)

*Primary Examiner* — Craig D Ricci
(74) *Attorney, Agent, or Firm* — Timothy H. Van Dyke; Wolter Van Dyke Davis, PLLC

(57) ABSTRACT

Various embodiments relate to compounds and methods useful for preventing or treating a cancer in a subject. The method may include administering to a subject a composition according to any of the embodiments described herein in an amount effective to inhibit metastatic activity or tumor growth in the subject.

8 Claims, 29 Drawing Sheets

(56) References Cited

OTHER PUBLICATIONS

Hayes, Candace S. et al., "Polyamine blockade Therapy Reverses Immunosuppression in the Tumor Microenvironment", Cancer Immunol Res, Mar. 2014, vol. 2, No. 3, pp. 274-285.
Kaur, Navneet et al., "Designing the Polyamine Pharmacophore: Influence of N-Substituents on the Transport Behavior of Polyamine Conjugates", J. Med. Chem., 2008, vol. 51, pp. 2551-2560.
Kurihara, Shin et al., "Putrescine Importer PlaP Contributes to Swarming Motility and Urothelial Cell Invasion in Proteus mirabilis", The Journal of Biological Chemistry, May 31, 2013, vol. 288, No. 22, pp. 15668-15676.
Lewis, John R. et al., "Polyamine Inhibitors for Treatment of Feline Oral Squamous Cell Carcinoma: A Proof-of-Concept Study". J Vet Dent, 2013, vol. 30, No. 3, pp. 140-145.
Massaro, Chelsea et al., "Investigation of Polyamine Metabolism and Homeostasis in Pancreatic Cancers", Med. Sci., 2017, vol. 5, No. 32, 14 pages.
Meyskens, Frank L. et al., "Development of Difluoromethylornithine (DFMO) as a Chemoprevention Agent", Clinical Cancer Research, May 1999, vol. 5, pp. 945-951.
Meyskens, Frank L. et al., "A phase II study-difluoromethylorinthine (DFMO) for the treatment of metastatic melanoma", Investigational New Drugs, 1986, vol. 4, pp. 257-262.
Muth, Aaron et al., "Polyamine Transport Inhibitors: Design, Synthesis, and Combination Therapies with Difluoromethylornithine", J. Med. Chem., 2014, vol. 57, pp. 348-363.
Muth, Aaron et al., "Development of Polyamine Transport Ligands with Improved Metabolic Stability and Selectivity against Specific Human Cancers", J. Med. Chem., 2013, vol. 56, pp. 5819-5828.
Kaur, Navneet et al., "A Comparison of Chloroambucil- and Xylene-Containing Polyamines Leads to Improved Ligands for Accessing the Polyamine Transport System",J. Med. Chem., 2008, vol. 51, pp. 1393-1401.
Niemand, Jandeli et al., "Anthracene-Polyamine Conjugates Inhibit In Vitro Proliferation of Intraerythrocytic Plasmodium falciparum Parasites", Antimicrobial Agents and Chemotherapy, Jun. 2013, vol. 57, No. 6, pp. 2874-2877.
Phanstiel IV, Otto et al., "Design of Polyamine Transport Inhibitors as Therapeutics", Drug Discovery Science, No. 17, p. 162.
Phanstiel IV, Otto et al., "Structure-activity investigations of polyamine-anthracene conjugates and their uptake via the polyamine transporter", Amino Acids, 2007, vol. 33, pp. 305-313.
Pubchem-CID, 112983934, Create Date, Jan. 28, 2016, pp. 1-7, p. 2 structure.
Raul, F, "Revival of 2-(difluoromethyl)ornithine (DFMO), an inhibitor of polyamine biosynthesis, as a cancer chemopreventive agent", Biochemical Society Transactions, 2007, vol. 35, part 2, pp. 353-355.
Reigada, Chantal et al., "Targeting polyamine transport in Trypanosoma cruzi" European Journal of Medicinal Chemistry, 2018, vol. 147, pp. 1-6.
Samal. Katherine et al., "AMXT-1501, a novel polyamine transport inhibitor, synergizes with DFMO in inhibiting neuroblastoma cell proliferation by targeting both ornithine decarboxylase and polyamine transport", Int. J. Cancer, 2013, vol. 133, pp. 1323-1334.
Skorupski, K. A. et al., "Phase I/II clinical trial of 2-difluoromethylornithine (DFMO) and a novel polyamine transport inhibitor (MQT 1426) for feline oral squamous cell carcinoma", Veterinary and Comparative Oncology, 2011, vol. 9, No. 4, pp. 275-282.
Traquete, Rui et al., "Ant 4,4, a polyamine-anthracene conjugate, induces cell death and recovery in human promyelogenous leukemia cells (HL-60)", Amino Acids, 2013, vol. 44, pp. 1193-1203.
Tsen, Chung et al., "A *Drosophila* Model To Identify Polyamine-Drug Conjugates That Target the Polyamine Transporter in an Intact Epithelium", J. Med. Chem., 2008, vol. 51, pp. 324-330.
Wang, Minpei et al., "Evaluation of Polyamine Transport Inhibitors in a *Drosophila* Epithelial Model Suggests the Existence of Multiple Transport Systems" Med. Sci., 2017, vol. 5, No. 27, 15 pages.
Weeks, Reitha S. et al. "Novel Lysine-Spermine Conjugate Inhibits Polyamine Transport and Inhibits Cell Growth When Given with DFMO", Experimental Cell Research, 2000, vol. 261, pp. 293-302.
Grossi, Mario et al., "Inhibition of Polyamine Uptake Potentiates the Anti-Proliferative Effect of Polyamine Synthesis Inhibition and Preserves the Contractile Phenotype of Vascular Smooth Muscle Cells," J. Cell. Physiol. 231: 1334-1342, 2016, 2015 Wiley Periodicals, Inc.
NCGC, RN 959501-13-4 Registry, Dec. 26, 2007, 1 page.
CAS, 901158-65-4, Registry, Aug. 14, 2006, 1 page.
CAS, 1923243-68-8, Registry, Jun. 2, 2016, 1 page.
ESSR, PCT/2019/046122, Sep. 3, 2022, 14 pages.
Al-Obaid, Abdulrahman et al., "Substituted quinazolines, part 3. Synthesis, in vitro antitumor activity and molecular modeling study of certain 2-thieno-4(3H)-quinazolinone analogs", European Journal of Medicinal Chemistry 44 (2009) 2379-2391.
CAS, 518009-05-7, Registry, May 21, 2003.
DataBase 1242906-85-9, Registry, Sep. 27, 2010.
DataBase1243095-98-8, Registry, Sep. 27, 2010.
DataBase1243104-25-7, Registry, Mar. 27, 2010.
DataBase1296316-61-4, Registry, May 18, 2011.
Deck, L.M. et al., "Synthesis of derivatives of thiophene using methyl 2-Isothiocyanatobenzoate", J. Heterocyclic Chem., 38, 343, 2001.
Dolzhenko, A.V. et al., "Synthesis and biological activity of N-Acyl-5-Bromanthranilic acids", Pharmaceutical Chemistry Journal, vol. 40, No. 8, 2006.
Hsieh, Pei-Wen et al., "The evaluation and structure-activity relationships of 2-benzoylaminobenzoic esters and their analogues as anti-inflammatory and anti-platelet aggregation agents", Bioorganic & Medicinal Chemistry letters 17 (2007) 1812-1817.
Sequence 92553-91-8, Registry, Dec. 17, 1984, 1 page.
Seaquence 1242875-40-6, Registry, Sep. 27, 2010.
Pattarawarapan, Mookda et al., "Mechanochemical synthesis of substituted 4H-3, 1-benzoxazin-4-ones, 2-Aminobenzoxazin-4-ones, and 2-Amino-4H-3, 1-benzothiazin-4-ones mediated by 2, 4, 6-Trichloro-1,3,5-triazine and Triphenylphospine", Synlett, 2017, 28, 289-592.
PubChem, N-[4-(4-Phenylpipearzin-1-yl)Phenyl]bensamide, Nov. 13, 2019, 7 pages.
Putin, Evgeny et al., "Adversarial threshold Neural computer for Molecular de Novo design", Pharmaceutics 2018, 15, 4386-4397.

\* cited by examiner

NON-POLYAMINE BASED POLYAMINE TRANSPORT INHIBITORS AND THEIR USE IN THE TREATMENT OF HUMAN CANCERS

FIELD OF INVENTION

This disclosure relates generally to polyamine transport inhibitors and more specifically to non-polyamine based polyamine transport inhibitors. The polyamine transport inhibitors according to various embodiments may affect the uptake and/or intracellular trafficking of polyamines.

BACKGROUND

Even though polyamines are an established anti-proliferative target, strategies to inhibit polyamine pools often fail. In general, efforts to inhibit the polyamine biosynthetic enzymes (ornithine decarboxylase (ODC), spermidine synthase (SRM) and spermine synthase (SMS) in human cancers often induce intracellular polyamine depletion, but have limited effect on growth unless the total polyamine pools (especially spermidine) are decreased dramatically.[1] For example, in pancreatic ductal adenocarcinoma (PDAC) cells (L3.6 pl cells) one needed to reduce the intracellular polyamine pools below 80% of the untreated control to affect growth in cell culture.[2] In this regard, cancers have excess pools of polyamines to accommodate/survive any temporary reduction of polyamine pools and polyamine homeostasis is tightly controlled via a balance between polyamine biosynthesis, catabolism and import. Indeed, as shown in the following tables, treatment of L3.6 pl cells with polyamine biosynthesis inhibitors (e.g., alpha-difluoromethylornithine (DFMO, an ODC inhibitor), trans-4-methylcyclohexylamine (MCHA, a SRM inhibitor) or N-cyclohexyl-1,3-diaminopropane (CDAP, a SMS inhibitor) caused a reshuffling of intracellular polyamine pools and little to no effect on cell growth, except for the DFMO-treated entries.[1] In this regard, ODC is a preferred target as its inhibition affects cell growth. The problem with targeting ODC is that ODC protein has a short half-life in humans (~30 min) and therefore requires high doses of the inhibitor (DFMO) in order to be effective.[3] DFMO has a 40 year history in the clinic, is well tolerated by patients and is non-toxic even at high doses (500-1500 mg/m$^2$/day).[3-5] DFMO is already FDA approved for the treatment of African sleeping sickness (i.e., African trypanosomiasis). Unfortunately, DFMO-treated tumors often circumvent the block of polyamine biosynthesis (i.e. the inhibition of ODC) by importing extracellular polyamines to make up the polyamine pool deficiency.[2] For this reason, a need exists for novel polyamine transport inhibitors (PTIs) to address this tumor escape pathway.[6-13] The prior art is essentially all based upon polyamine-containing scaffolds which have limitations in terms of significant off-target effects and rapid clearance times in vivo. The development of non-polyamine based PTIs, therefore, offers the opportunity to dramatically alter the pharmacokinetic profile of the drug, increase drug potency and therapeutic effectiveness. Greater potency could lead to reduced drug dosing and fewer side effects.

BRIEF SUMMARY

Various embodiments relate to a pharmacophore having the general structure according to Formula I.

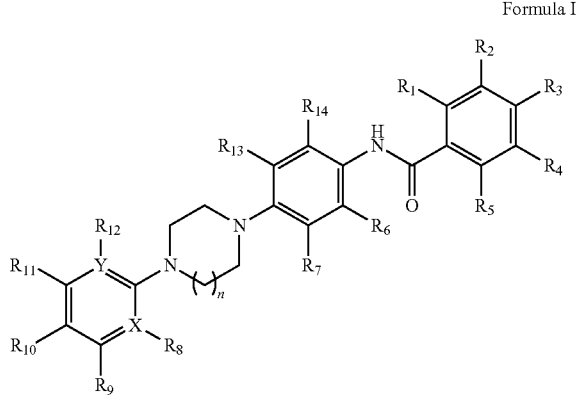

Formula I

Referring to Formula I, in general:
n may be selected from 1 and 2;
X may be selected from C and N;
Y may be selected from C and N;
$R_1$ may be selected from H, Cl, Me, and OMe;
$R_2$ may be selected from H and Me;
$R_3$ may be selected from H, F, CF$_3$, Me, OMe, and OPh;
$R_4$ may be selected from H, Cl, and Me;
$R_5$ may be selected from H, Cl, Me, and OMe;
$R_6$ may be selected from H and COOH;
$R_7$ may be selected from H and COOH;
$R_8$ may be selected from a lone pair of electrons, H, Cl, Me, OMe, OEt, OH, and CH$_2$OH;
$R_9$ may be selected from H, Cl, and Me;
$R_{10}$ may be selected from H, OH, OMe, and COMe;
$R_{11}$ may be selected from H, Cl, and Me;
$R_{12}$ may be selected from a lone pair of electrons, H, Cl, Me, OMe, OEt, OH, and CH$_2$OH;
$R_{13}$ may be selected from H and COOH; and
$R_{14}$ may be selected from H and COOH.

Various embodiments relate to a pharmacophore having the general structure according to Formula II.

Formula II

Referring to Formula II, in general:
n may be selected from 1 and 2;
X may be selected from C and N;
Y may be selected from C and N;
$R_1$ may be selected from H, Cl, Me, and OMe;
$R_2$ may be selected from H and Me;
$R_3$ may be selected from H, Me, and OMe;
$R_4$ may be selected from H and Me;

R₅ may be selected from H, Cl, Me, and OMe;
R₆ may be selected from H and COOH;
R₇ may be selected from H and COOH;
R₈ may be selected from a lone pair of electrons, H, Cl, Me, OMe, OEt, OH, and CH₂OH;
R₉ may be selected from H, Cl, and Me;
R₁₀ may be selected from H, O, OMe, and COMe;
R₁₁ may be selected from H, Cl, and Me;
R₁₂ may be selected from a lone pair of electrons, H, Cl, Me, OMe, OEt, OH, and CH₂OH;
R₁₃ may be selected from H and COOH; and
R₁₄ may be selected from H and COOH.

Various embodiments relate to a pharmacophore having the general structure according to Formula III.

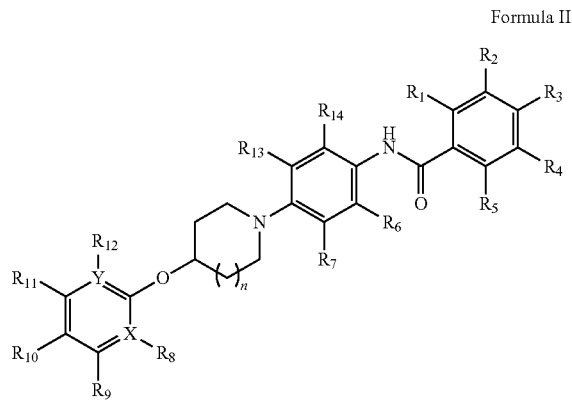

Formula III

Referring to Formula III, in general:
n may be selected from 1 and 2;
X may be selected from C and N;
Y may be selected from C and N;
R₁ may be selected from H, Cl, Me, and OMe;
R₂ may be selected from H and Me;
R₃ may be selected from H, Me, and OMe;
R₄ may be selected from H and Me;
R₅ may be selected from H, Cl, Me, and OMe;
R₆ may be selected from H and COOH;
R₇ may be selected from H and COOH;
R₈ may be selected from a lone pair of electrons, H, Cl, Me, OMe, OEt, OH, and CH₂OH;
R₉ may be selected from H, Cl, and Me;
R₁₀ may be selected from H, O, OMe, and COMe;
R₁₁ may be selected from H, Cl, and Me;
R₁₂ may be selected from a lone pair of electrons, H, Cl, Me, OMe, OEt, OH, and CH₂OH;
R₁₃ may be selected from H and COOH; and
R₁₄ may be selected from H and COOH.

Various embodiments relate to a compound having the structure, according to Formula IV:

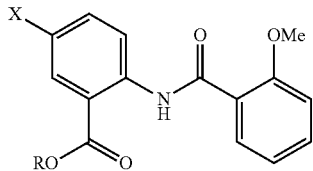

Formula IV

Referring to Formula IV, according to various embodiments, R may be selected from H, Me or Et or isopropyl or represents the counter-ion of a pharmaceutically acceptable salt like a carboxylate salt containing Na+ or K+. In general, X may be selected from the group consisting of H, a heteroatom, an alkyl, an alkylaryl, a dialkylamine, and a heterocycle. According to various embodiments, X may be a heterocycle selected from the group consisting of (connected at the wavy bond line):

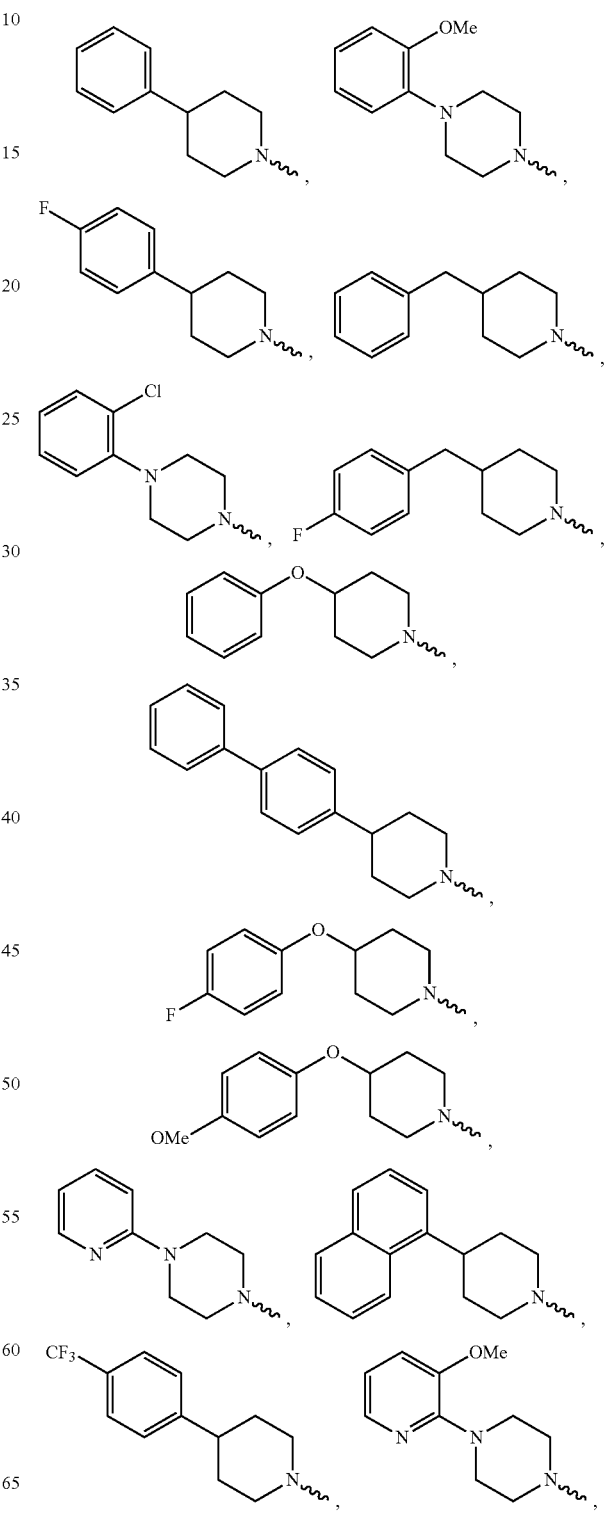

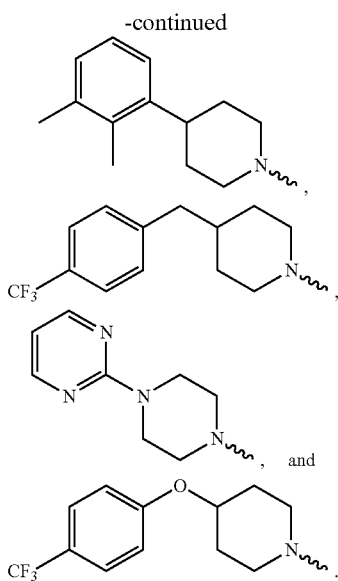

Still referring to Formula IV, according to various embodiments, the heterocycle may include a nitrogen-containing aromatic ring, and the heterocycle may be bonded to the compound via a nitrogen atom in the heterocyclic ring. According to various other embodiments of Formula IV, X may be a hydrogen atom. According to various embodiments of Formula IV, X may be a heteroatom. For example, the heteroatom may be F, Cl, Br, or I. According to various embodiments of Formula IV, X may be an alkyl chain. The alkyl chain may be any suitable length, for example a $C_1$-$C_{10}$ alkyl chain. For example, the alkyl chain may be methyl, ethyl, propyl, n-propyl, isopropyl, butyl, n-butyl, isobutyl, sec-butyl, pentyl, n-pentyl, 2-methylbutyl, isopentyl or other linear or branched alkyl chains up to 10 carbons. According to various embodiments of Formula IV, X may be an alkylaryl chain. The alkyl aryl chain may include one ore more alkyl chains. Each alkyl chain may be any suitable length, for example a $C_1$-$C_{10}$ alkyl chain. The alkyl chains may or may not have the same length. For example, the alkylaryl chain may be a benzyl, a phenethyl, or a dialkylamino. The dialkylamino may be a dimethylamino or a diethylamino group, for example. According to various embodiments X may be a dialkylamine. The dialkylamine may be, for example, $NMe_2$, $NEt_2$, $N^4$-methylpiperazinyl, $N^4$-ethylpiperazinyl, $N^4$-propylpiperazinyl, $N^4$-butylpiperazinyl, $N^4$-isopropylpiperazinyl, $N^4$-isobutylpiperazinyl, or $N^4$-isopentylpiperazinyl.

Various embodiments relate to a compound having the structure according to Formula V:

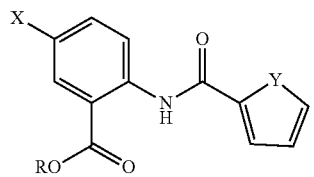

Formula V

Referring to Formula V, according to various embodiments, R may be selected from H, Me or Et or isopropyl or represents the counter-ion of a pharmaceutically acceptable salt like a carboxylate salt containing Na+ or K+. According to various embodiments, Y may be selected from either $CH_2$, NH, O, S, N—Me, N—Ac, N—Bn or N—Bz. In general, X may be selected from the group consisting of H, a heteroatom, an alkyl, an alkylaryl, a dialkylamine, and a heterocycle. According to various embodiment of Formula V, X may be a heterocycle selected from the group consisting of (connected at the wavy bond line):

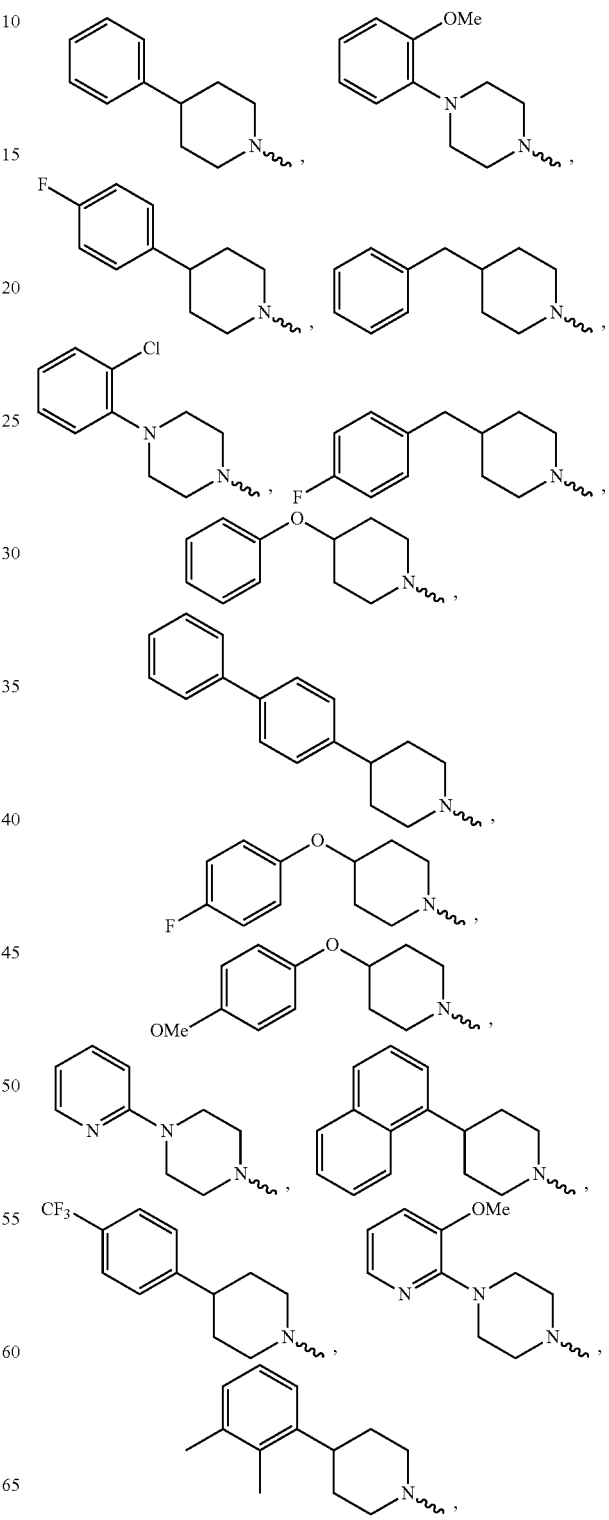

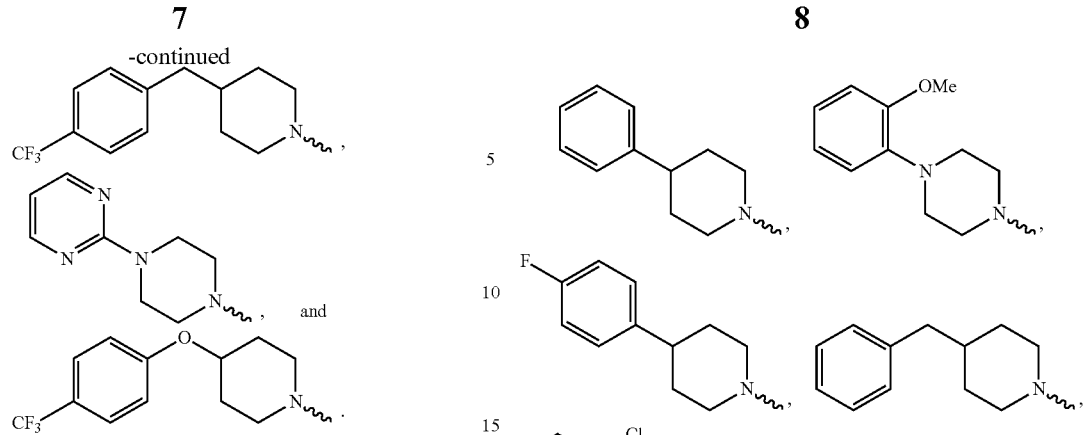

Still referring to Formula V, according to various embodiments, the heterocycle may include a nitrogen-containing aromatic ring, and the heterocycle may be bonded to the structure via a nitrogen atom in the heterocyclic ring. According to various other embodiments of Formula V, X may be a hydrogen atom. According to various embodiments of Formula V, X may be a heteroatom. For example, the heteroatom may be F, Cl, Br, or I. According to various embodiments, X may be an alkyl chain. The alkyl chain may be any suitable length, for example a $C_1$-$C_{10}$ alkyl chain. For example, the alkyl chain may be methyl, ethyl, propyl, n-propyl, isopropyl, butyl, n-butyl, isobutyl, sec-butyl, pentyl, n-pentyl, 2-methylbutyl, isopentyl. According to various embodiments of Formula V, X may be an alkylaryl chain. The alkyl aryl chain may include one ore more alkyl chains. Each alkyl chain may be any suitable length, for example a $C_1$-$C_{10}$ alkyl chain. The alkyl chains may or may not have the same length. For example, the alkylaryl chain may be a benzyl, a phenethyl, or a dialkylamino. The dialkylamino may be a dimethylamino or a diethylamino group, for example. According to various embodiments X may be a dialkylamine. The dialkylamine may be, for example, $NMe_2$, $NEt_2$, $N^4$-methylpiperazinyl, $N^4$-ethylpiperazinyl, $N^4$-propylpiperazinyl, $N^4$-butylpiperazinyl, $N^4$-isopropylpiperazinyl, $N^4$-isobutylpiperazinyl, or $N^4$-isopentylpiperazinyl.

Various embodiments relate to a compound having the structure, according to Formula VI

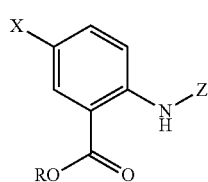

Formula VI

Referring to Formula VI, according to various embodiments, R may be selected from H, Me or Et or isopropyl or represents the counter-ion of a pharmaceutically acceptable salt like a carboxylate salt containing Na+ or K+. In general, X may be selected from the group consisting of H, a heteroatom, an alkyl, an alkylaryl, a dialkylamine, and a heterocycle. According to various embodiment, X may be a heterocycle selected from the group consisting of (connected at the wavy bond line):

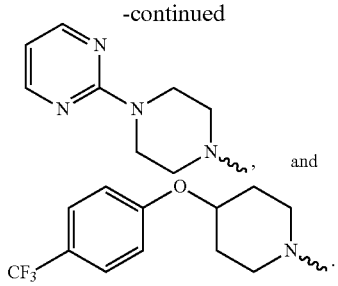

Still referring to Formula VI, according to various embodiments, the heterocycle may include a nitrogen-containing aromatic ring, and the heterocycle may be bonded to the structure via a nitrogen atom in the nitrogen-containing heterocyclic ring. According to various other embodiments, X may be a hydrogen atom. According to various embodiments of Formula VI, X may be a heteroatom. For example, the heteroatom may be F, Cl, Br, or I. According to various embodiments, X may be an alkyl chain. The alkyl chain may be any suitable length, for example a $C_1$-$C_{10}$ alkyl chain. For example, the alkyl chain may be methyl, ethyl, propyl, n-propyl, isopropyl, butyl, n-butyl, isobutyl, sec-butyl, pentyl, n-pentyl, 2-methylbutyl, isopentyl or other linear or branch chains up to ten carbons. According to various embodiments, X may be an alkylaryl chain. The alkyl aryl chain may include one or more alkyl chains. Each alkyl chain may be any suitable length, for example a $C_1$-$C_{10}$ alkyl chain. The alkyl chains may or may not have the same length. For example, the alkylaryl chain may be a benzyl, a phenethyl, or a dialkylamino. The dialkylamino may be a dimethylamino or a diethylamino group, for example. According to various embodiments X may be a dialkylamine. The dialkylamine may be, for example, $NMe_2$, $NEt_2$, $N^4$-methylpiperazinyl, $N^4$-ethylpiperazinyl, $N^4$-propylpiperazinyl, $N^4$-butylpiperazinyl, $N^4$-isopropylpiperazinyl, $N^4$-isobutylpiperazinyl, or $N^4$-isopentylpiperazinyl.

According to various embodiments of Formula VI, Z may be a heterocycle selected from

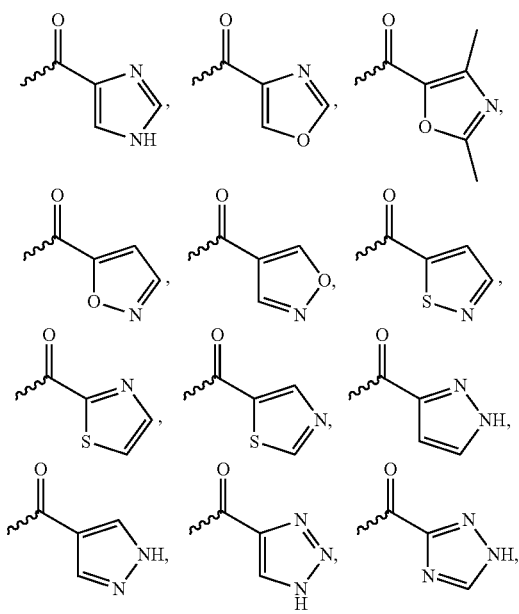

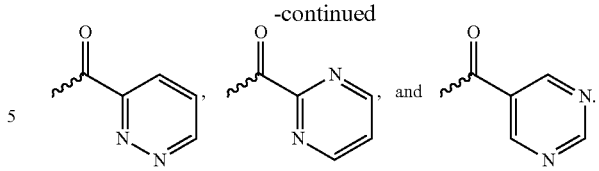

Alternatively, various embodiments of Formula VI, include reduced forms of the substituent Z, where the carbonyl from each heterocycle listed above is replaced by a $CH_2$ group. and is selected from one of the following (attached via the wavy line):

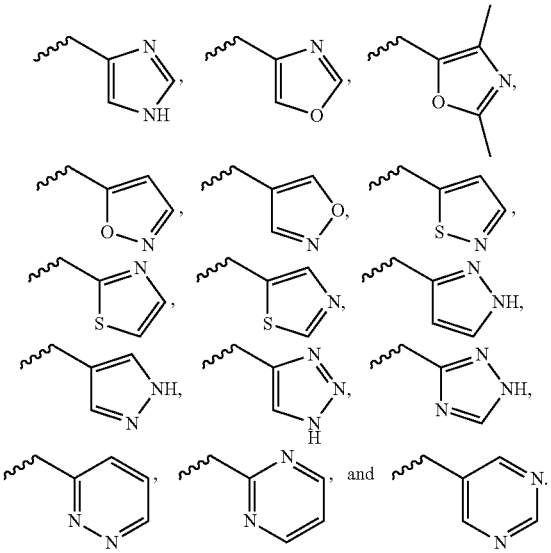

Various embodiments relate to methods for preventing or treating a cancer in a subject, the method comprising: administering to a subject a composition according to any of the embodiments described herein in an amount effective to inhibit metastatic activity or tumor growth in the subject. Another embodiment relates to the methods of inhibiting the proliferation of cells.

These and other features, aspects, and advantages of various embodiments will become better understood with reference to the following description, figures, and claims.

BRIEF DESCRIPTION OF THE FIGURES

These and other features, aspects, and advantages of the present disclosure will become better understood with reference to the following description and appended claims, and accompanying drawings where:

Figure 1:
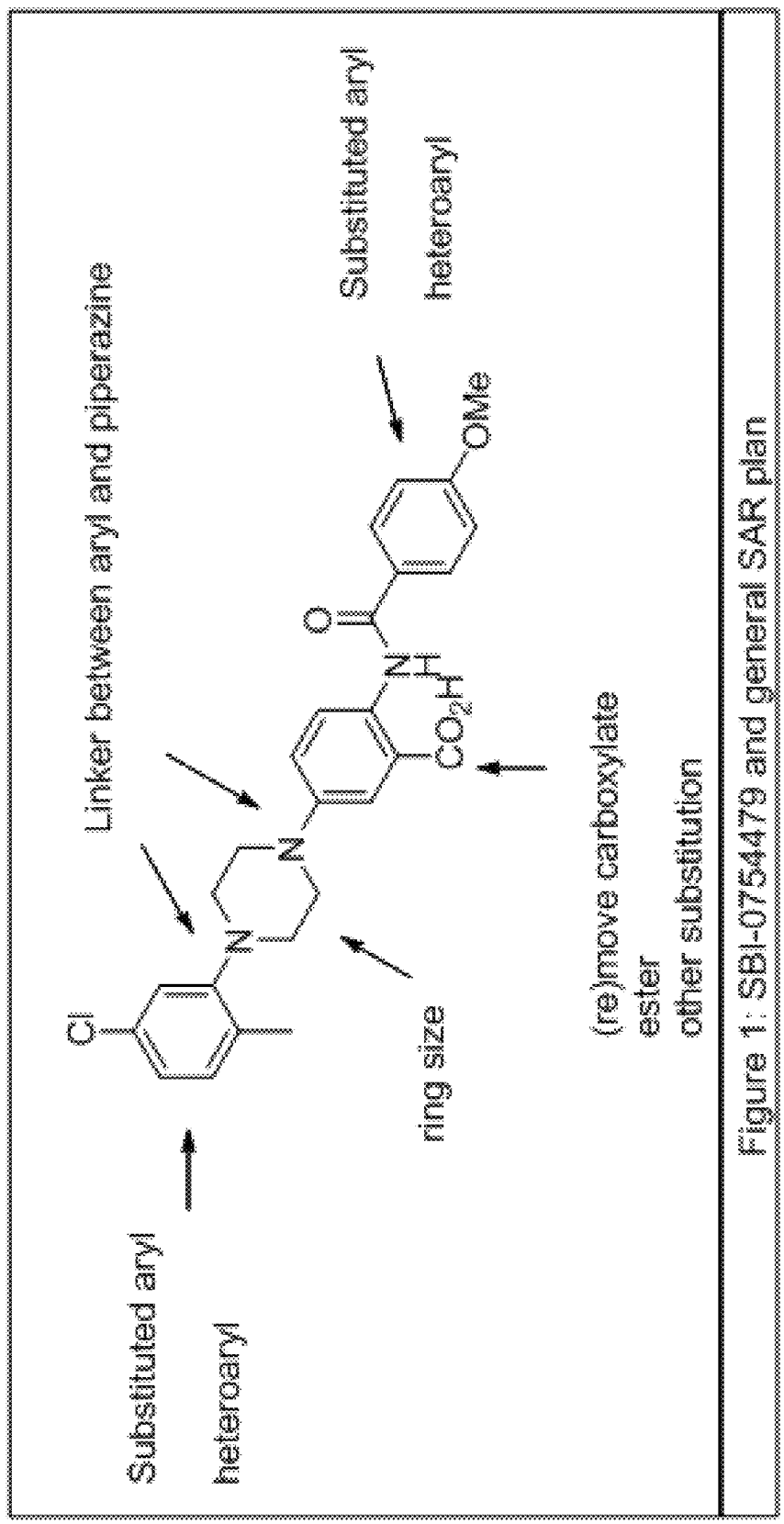
FIG. 1: is an example according to various embodiments illustrating a structural diagram of a compound.

It should be understood that the various embodiments are not limited to the arrangements and instrumentality shown in the drawings.

DETAILED DESCRIPTION

Targeting polyamine metabolism is a proven anticancer strategy. Polyamines play diverse roles in cells including key roles in translation, transcription, chromatin remodeling, autophagy, growth, eIF5A formation, and the immune response. One approach to inhibit cell growth is to starve cells of their polyamine components. This can be accomplished by the combination of a polyamine biosynthesis inhibitor (e.g., DFMO) and a polyamine transport inhibitor (PTI). A combination therapy is needed because proliferating cells like cancer cells when treated with a polyamine biosynthesis inhibitor often circumvent the biosynthesis inhibitor by increasing import of exogenous polyamines to maintain intracellular polyamine pools. Virtually all known polyamine transport inhibitors are based upon polyamine scaffolds and work via competitive inhibition of polyamine import (REF: Design of Polyamine Transport Inhibitors as Therapeutics. Otto Phanstiel IV; Jennifer J. Archer, in *Polyamine Drug Discovery*, P. Woster and R. A. Casero, eds., RSC Publishing, 2012. 162-187. ISBN 9781849731904). In short, these work by out-competing the native polyamines (putrescine, spermidine and spermine) for cell entry. In this regard, polyamine-based polyamine transport inhibitors compete and inhibit all modes of polyamine import. Various embodiments of the present disclosure provide new non-polyamine-based polyamine transport inhibitors. These small molecules are special and represent a first in class design of compounds which inhibit specific modes of polyamine import. While the literature suggests that multiple polyamine import modes were likely, the molecular tools needed to inhibit these putative modes of polyamine import have not been described. Various embodiments described herein provide these new tools which will be invaluable to basic scientist interested in polyamine metabolism, intracellular vesicular trafficking, and to the medical community for their ability to work in combination with a polyamine biosynthetic inhibitor to inhibit proliferative diseases like cancer and infectious diseases. To the best of our knowledge, existing molecular tools inhibit both basal polyamine uptake and DFMO-stimulated (obligate) polyamine import. These existing tools contain linear polyamine designs (and are therefore all polyamine based) and compete for cell entry in both the basal and obligate import pathways. The new molecules described here do not contain linear polyamines within their structure and contain the ability to selectively inhibit both pathways or just one mode of polyamine import and not the other. Armed with these selective inhibitors, one has the opportunity to block specific modes of polyamine uptake for clinical benefit in the treatment of proliferative diseases.

Each mode of uptake (basal or obligate) involves a multistep process, wherein the polyamine is bound and taken up into the cell and then trafficked to its ultimate destination inside the cell. Compounds which inhibit any one of these steps can be effective polyamine transport inhibitors as they disrupt or inhibit the ability of the polyamine to reach the cellular compartment(s) needed to affect cell growth.

Polyamines are charged at physiological pH and thus behave as polycations in vivo. As such, they can bind to many biological anions like DNA, RNA and proteoglycans and, therefore, can have significant off target effects and toxicity. By designing a non-polyamine based PTI compound, various embodiments limit these off target effects. In addition, polyamines are hydrophilic and are often cleared quickly by the kidney. Designing more lipophilic compounds, like those disclosed here, should increase the half-life of the drug in the body and improve potency and drug efficacy. The synthesis of these new compounds occurs in four synthetic steps from commercially available starting materials. In contrast, prior art methods require five steps.

Since polyamine transport plays critical roles in many proliferative diseases, a potent PTI can have many applications. For example, a PTI in combination with DFMO can starve human cancers of the polyamines they need to grow and thus have anticancer applications (Gitto, Sarah; Pandey, Veethika; Oyer, Jeremiah; Copik, Alicja; Hogan, Frederick; Phanstiel, Otto; Altomare, Deborah. Difluoromethylornithine Combined with a Polyamine Transport Inhibitor is Effective against Gemcitabine Resistant Pancreatic Cancer. *Mol Pharm.* 2018, 15, 369-376). PTI+DFMO therapy also jump starts the immune response and can provide an effective immunotherapy in vivo against melanoma. (Alexander, E.; Minton, A.; Peters, M.; Phanstiel, O.; Gilmour, S., A Novel Polyamine Blockade Therapy Activates an Anti-Tumor Immune Response. *Oncotarget* 2017, 8, 84140-84152.) The ability to modulate the immune response could also have applications in viral infections such as HIV. Indeed, the HIV TAT protein competes with polyamines for cell entry (Katrin Mani, Staffan Sandgren, Johanna Lilja, Fang Cheng, Katrin Svensson, Lo Persson, and Mattias Belting. HIV-Tat protein transduction domain specifically attenuates growth of polyamine deprived tumor cells. *Mol Cancer Ther* 2007, 6, 782-788.). Therefore, a PTI may also function as an antiviral agent.

Certain organisms are wholly dependent on polyamine import for their survival and are, thus, very sensitive to blockade of polyamine import. Various embodiments have also shown that PTI compounds (that are polyamine based) can inhibit the growth of parasitic protozoa like *T. cruzi* (Chantal Reigada, Otto Phanstiel IV, Mariana R. Miranda, Claudio A. Pereira. Targeting polyamine transport in *Trypanosoma cruzi*. *Eur. J. Med. Chem.* 2018, 147, 1-6). Since *T. cruzi* is responsible for Chagas disease, these new PTI agents could provide new medicines for treating Chagas disease and other parasitic protozoan infections by blocking the ability of the parasite to import polyamines. Other organisms like *P. falciparum* (the malarial parasite) have the ability to both make and import polyamines. In another application, the combination of DFMO+PTI can starve microorganisms of the polyamines needed for their growth and could provide novel anti-infective agents. The PTIs can also affect swarming behavior of *Proteus mirabilis* (Putrescine importer PlaP contributes to swarming motility and urolithelial cell invasion in *Proteus mirabilis*. Kurihara, S.; Sakai, Y.; Suzuki, H.; Muth, A.; Phanstiel, O.; Rather, P. N. J. Biol. Chem. 2013, 288,15668-15676.). Since *P. mirabilis* is present in urinary tract infections in humans, these new compounds may have utility as antibiotics. The DFMO+PTI also affects vascular remodeling (Inhibition of Polyamine Uptake Potentiates the Anti-Proliferative Effect of Polyamine Synthesis Inhibition and Preserves the Contractile Phenotype of Vascular Smooth Muscle Cells. Grossi, M.; Phanstiel, O.; Rippe, K.; Sward, K.; Alajbegovic, A.; Albinsson, S.; Forte, A.; Persson, L.; Hellstrand, P.; Nilsson, B-O. *J. Cell. Physiol.* 2015, 9999, 1-9). As such the DFMO+PTI therapy may provide a viable approach for targeting unwanted vascular cell proliferation in vivo, including vascular restenosis.

In sum, since known polyamine-based PTI systems (like the trimer44NMe PTI compound) have these properties, the new PTI designs according to various embodiments should also provide similar outcomes.

Various non-polyamine PTI compounds disclosed herein may also be used alone or in combination with other medicines to limit the growth of target cell types (e.g., tumor cells, bacteria, protozoa, or vascular cells). Melanoma, colorectal cancers, breast cancers and pancreatic cancers may be especially sensitive to this DFMO+PTI approach due to their addiction to polyamine growth factors. For example, Kras driven tumors like pancreatic ductal adenocarcinomas (PDAC) have increased intracellular pools of polyamines and high polyamine uptake rates (ATP13A3 and Caveolin-1 as Potential Biomarkers for Difluoromethylornithine-based therapies in Pancreatic Cancers. Meenu Madan, Arjun Patel, Kristen Skruber, Dirk Geerts, Deborah A. Altomare, and Otto Phanstiel IV. *Am. J. Cancer Res.*, 2016, 6, 1231-1252.). Therefore, various embodiments allow for the development of a personalized medicine using established biomarkers (high ATP13A3, low Cav-1, high SMS, low SRM) to identify tumor types (i.e., patient tumors) that will best benefit from the combination therapy (DFMO+PTI). This is the type of focused, targeted (personalized) medicine of the future which can benefit patients by selectively targeting their tumors.

Various embodiments may be utilized to develop multiple applications for cancer, infectious disease and vascular restenosis. In this manner three or more products/biomedical applications may be derived from one molecule.

1.1 Definitions

The present disclosure may be understood more readily by reference to the following detailed description of preferred embodiments of the disclosure as well as to the examples included therein. All numeric values are herein assumed to be modified by the term "about," whether or not explicitly indicated. The term "about" generally refers to a range of numbers that one skilled in the art would consider equivalent to the recited value (i.e., having the same function or result). In many instances, the term "about" may include numbers that are rounded to the nearest significant figure. Generally, as used herein, the terms "about" and "approximately" refer to values that are ±10% of the stated value.

Various embodiments are described by reference to chemical structures. In the chemical structures various chemical moieties are represented by a lettered group such as "R-group." Some R-groups are described by reference to another chemical structure. A wavy bond line in a structure representing an R-group indicates the point at which the R-group is attached to or bonded to the main structure. In some chemical structures various cyclic moieties are represented by lettered rings. The lettered ring may represent a variety of cyclic structures. Some cyclic structures are described by reference to another chemical structure. A wavy bond line in a structure representing a cyclic structure indicates a bond that is shared with the main structure, or the point at which the cyclic structure is fused to the main structure to form a polycyclic structure. Various subscripts are also used. Each R-group has a numeric subscript which distinguishes it from other R-groups. R-groups and lettered rings may also include a lowercase alphabetical subscript, indicating that different embodiments, may have differing numbers of that moiety. If a lowercase alphabetical subscript may be 0, it means that, in some embodiments, the moiety may not be present. A dashed line in a cyclic structure indicates that in various embodiments one or more double-bounds may be present. When a compound may include more than one instance of a moiety, for example a moiety represented by an R-group, and that moiety is described as being "independently selected" from a list of options, each instance may be selected from the complete list without respect to any prior selections from the list; in other words, the instances may be the same or different and the same list item may be selected for multiple instances. Some R-group substitutions may indicate a range, such as $C_1$-$C_6$ alkyl. Such a range indicates that the R-group may be a $C_1$ alkyl, a $C_2$ alkyl, a $C_3$ alkyl, a $C_4$ alkyl, a $C_5$ alkyl, or a $C_6$ alkyl. In other words, all such ranges are intended to include an explicit reference to each member within the range.

As used herein, the terms "administering" or "administration" of a compound or agent as described herein to a subject includes any route of introducing or delivering to a subject a compound to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

As used herein, the term "analog" refers to a compound having a structure similar to that of another compound, but differing from the other compound with respect to a certain component or substituent. The compound may differ in one or more atoms, functional groups, or substructures, which may be replaced with other atoms, groups, or substructures. In one aspect, such structures possess at least the same or a similar therapeutic efficacy.

The term "cancer" as used herein refers to a physiological condition in mammals that is typically characterized by unregulated cell growth. Exemplary cancers include, but are not limited to carcinoma, lymphoma, blastoma, sarcoma, and leukemia. More particularly, examples of such cancers include lung cancer, bone cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, neuroblastoma, spinal axis tumors, glioma, meningioma, and pituitary adenoma.

As used herein, the terms "co-administered, "co-administering," or "concurrent administration", when used, for example with respect to administration of a conjunctive agent along with administration of a composition as described herein refers to administration of an anti-metastatic agent as described herein and a conjunctive agent such that both can simultaneously achieve a physiological effect. The two agents, however, need not be administered together. In certain embodiments, administration of one agent can precede administration of the other, however, such co-administering typically results in both agents being simultaneously present in the body (e.g. in the plasma) of the subject.

As used herein, "derivative" refers to a compound derived or obtained from another and containing essential elements of the parent compound. In one aspect, such a derivative possesses at least the same or similar therapeutic efficacy as the parent compound.

As used herein, the terms "disease," "disorder," or "complication" refers to any deviation from a normal state in a subject. In preferred embodiments, the methods and compositions of the present invention are useful in the diagnosis and treatment of diseases characterized at least in part by cell proliferation and/or differentiation where control of polyamine transport is required.

As used herein, by the term "effective amount," "amount effective," "therapeutically effective amount," or the like, it is meant an amount effective at dosages and for periods of time necessary to achieve the desired result.

As used herein, the term "metastases" or "metastatic" refers to a secondary tumor that grows separately elsewhere in the body from the primary tumor and has arisen from detached, transported cells, wherein the primary tumor is a solid tumor. The primary tumor, as used herein, refers to a tumor that originated in the location or organ in which it is present and did not metastasize to that location from another location.

As used herein, term "pharmaceutically acceptable salt" is intended to include art-recognized pharmaceutically acceptable salts. These non-toxic salts are usually hydrolyzed under physiological conditions, and include organic and inorganic acids and bases. Examples of salts include sodium, potassium, calcium, ammonium, copper, and aluminum as well as primary, secondary, and tertiary amines, polyamines, basic ion exchange resins, purines, piperazine, and the like. The term is further intended to include esters of lower hydrocarbon groups, such as methyl, ethyl, and propyl.

As used herein, the terms "composition" or "pharmaceutical composition" comprises one or more of the compounds described herein as active ingredient(s), or a pharmaceutically acceptable salt(s) thereof, and may also contain a pharmaceutically acceptable carrier and optionally other therapeutic ingredients. The compositions include compositions suitable for oral, rectal, ophthalmic, pulmonary, nasal, dermal, topical, parenteral (including subcutaneous, intramuscular and intravenous) or inhalation administration. The most suitable route in any particular case will depend on the nature and severity of the conditions being treated and the nature of the active ingredient(s). The compositions may be presented in unit dosage form and prepared by any of the methods well-known in the art of pharmacy. Dosage regimes may be adjusted for the purpose to improving the therapeutic response. For example, several divided dosages may be administered daily or the dose may be proportionally reduced over time. A person skilled in the art normally may determine the effective dosage amount and the appropriate regime.

As used herein, the term "preventing" means causing the clinical symptoms of a disorder or disease state, e.g., cancer, not to develop, e.g., inhibiting the onset of disease, in a subject that may be exposed to or predisposed to the disease state, but does not yet experience or display symptoms of the disease state.

As used herein, the term "prodrug" refers to a compound that is converted to a therapeutically active compound after administration, and the term should be interpreted as broadly herein as is generally understood in the art. Generally, but not necessarily, a prodrug is inactive or less active than the therapeutically active compound to which it is converted. For example, a methyl ester can be converted to a free carboxylic acid in vivo via the action of non-specific serum esterases.

As used herein, the term "stereoisomer" refers to a compound which has the identical chemical constitution, but differs with regard to the arrangement of the atoms or groups in space.

As used herein, the term "subject" refers to any animal (e.g., a mammal), including, but not limited to, humans, which may be the recipient of a particular treatment. The term is intended to include living organisms susceptible to conditions or diseases caused or contributed to by unrestrained cell proliferation and/or differentiation where control of polyamine transport is required. Examples of subjects include, but are not limited to, humans, dogs, cats, horses, cows, goats, sheep, and mice. As used herein, the terms "treating" or "treatment" refer to both therapeutic treatment and prophylactic or preventative measures, wherein the object is to prevent or slow down (lessen) the targeted pathologic condition or disorder.

1.2 Pharmaceutical Compositions

The compositions described herein may comprise an anti-metastatic agent as described herein. In one embodiment, there are provided pharmaceutical compositions comprising a compound of formula (1) above, or an analog, a derivative, a prodrug, a stereoisomer, or a pharmaceutically acceptable salt thereof, which can be administered to a patient to achieve a therapeutic effect, e.g., inhibit polyamine transport activity in the cells of a subject. In a particular embodiment, the pharmaceutical compound comprises a compound as described herein, or an analog, a derivative, a prodrug, a stereoisomer, or a pharmaceutically acceptable salt thereof. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones, such as anti-cancer agents.

In addition to the active ingredients, these pharmaceutical compositions can contain suitable pharmaceutically acceptable carriers comprising excipients and auxiliaries, which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage. Pharmaceutical preparations which will can be used orally include push fit capsules made of gelatin, as well as soft, sealed capsules made of gelatin and a coating, such as glycerol or sorbitol. Push fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also may contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Alternatively, salts can be formed with many amine motifs such as primary, secondary and tertiary amines or even the native polyamines themselves. Salts tend to be more soluble in aqueous or other protonic solvents than are the corresponding free base or free acid forms.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent to a particular site in an animal, such as a human. Preferably, the lipid composition of the liposome is capable of targeting to a specific organ of an animal, such as the lung, liver, spleen, pancreas, heart brain, lymph nodes, and skin.

A liposome useful in the present invention comprises a lipid composition that is capable of fusing with the plasma membrane of the targeted cell to deliver its contents to the cell. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

1.3 Determination of a Therapeutically Effective Dose

The determination of a therapeutically effective dose is well within the capability of those skilled in the art. A therapeutically effective dose refers to that amount of active ingredient which causes cytotoxicity to cancer cells and/or reduced metastatic behavior in a subject.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions which exhibit large therapeutic indices are preferred. The data obtained from cell culture assays and animal studies may be used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration. The toxicity of the present compounds of this invention can be further modulated by terminal N-alkylation. For example, polyamine compounds containing N-methyl groups are most stable to amine oxidases and are less toxic (see Designing the Polyamine Pharmacophore: Influence of N-substituents on the transport behavior of polyamine conjugates, Kaur, N.; Delcros, J.-G.; Archer, J.; Weagraff, N. Z.; Martin, B.; Phanstiel IV, O. *J. Med. Chem.* 2008, 51, 2551-2560.). These insights can be applied to the other compounds described herein. For example, tertiary amine systems should be stable to amine oxidases. In addition, methyl esters are less toxic than the free carboxylic acid form of the novel compositions (described herein in vitro) and provide an approach for lowered toxicity and pro-drug designs reliant upon hydrolysis or esterase activity in vivo to liberate the active carboxylic acid form.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of container and labeled for treatment of an indicated condition. Such labeling would include amount, frequency, and method of administration.

Normal dosage amounts can vary from 0.1 to 100,000 micrograms, up to a total dose of about 1 g, depending upon the route of administration, clearance rates, and/or duration of therapy. Guidance as to particular dosages and methods of delivery is provided in the literature and generally available to practitioners in the art. Those skilled in the art will employ different formulations for nucleotides than for proteins or their inhibitors.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects. Any of the therapeutic methods described above can be applied to any subject in need of such therapy, including, for example, mammals such as dogs, cats, cows, horses, rabbits, sheep, monkeys, and most preferably, humans.

1.4 Applications

The compositions and methods described herein may be useful for the treatment and/or prevention of a cancer. In one embodiment, the methods and compositions may be utilized for the treatment of a metastatic cancer. It is appreciated that the cancer being treated may already have metastasized or is potentially metastatic. The cancer may comprise non-solid tumors, e.g., leukemia, multiple myeloma, hematologic malignancies or lymphoma. In another embodiment, the cancer is characterized by solid tumors and their potential or actual metastases including, but not limited to, melanoma; non-small cell lung cancer; glioma; hepatocellular (liver) carcinoma; glioblastoma; carcinoma and tumors of the thyroid, bile duct, bone, gastric, brain/CNS, head and neck; and hepatic, stomach, prostrate, breast, renal, testicular, ovarian, skin, cervical, lung, muscle, neuronal, esophageal, bladder, lung, uterine, vulval, endometrial, kidney, colorectal, pancreatic, pleural/peritoneal membranes, salivary gland, and epidermoid.

1.5 Conjunctive Delivery

In accordance with another aspect, there is provided a method for preventing or treating a cancer in a subject. The method comprises (a) administering to a subject a composition comprising a compound according to formula (1) in an amount effective to inhibit or slow tumor cell growth in the subject; and (b) administering at least one of radiation or a cytotoxic chemotherapeutic agent to the subject in an amount effective to induce a cytotoxic effect in cancer cells of the subject. The administering steps (a) and (b) may comprise inserting a delivery mechanism into the subject. The delivery mechanism comprises a structure insertable into the subject through which the composition can be delivered and an actuating mechanism for directing the composition into the subject. The use of such a delivery mechanism may be applied to any other embodiment of a method for treating a subject described herein as well.

The delivery mechanism may be any suitable structure known in the art, such as a syringe having a needle insertable into the subject and a plunger. Instead of a syringe, other delivery mechanisms may be used for the intermittent or continuous distribution of the compositions, such as infusion pumps, syringe pumps, intravenous pumps or the like. Typically, these mechanisms include an actuating mechanism, e.g., a plunger or pump, for directing a composition into the subject. In one embodiment, a structure, e.g., catheter or syringe needle, which may be inclusive of or separate from the delivery mechanism, is first inserted into the subject and the composition is administered through the structure through activation of the actuating mechanism.

As explained herein, the compounds have been shown to exhibit exceptional anti-cancer activity with low toxicity. Thus, in certain embodiments, the one or more anti-cancer agents of the present invention may be administered to a subject in combination with a known therapy to help block the spread of a tumor and allow time for another therapy to work on the tumor. In one embodiment, the tumor is a primary tumor. When the cancer being prevented or treated herein is pancreatic cancer, the conjunctive therapy may comprise radiation, Whipple surgery, and/or administration of chemotherapeutic agents, including targeted therapies, such as Fluorouracil, Erlotinib Hydrochloride, Gemcitabine Hydrochloride, Abraxane (protein-bound paclitaxel), Mitozytrex (Mitomycin C), Mutamycin (Mitomycin C), or Tarceva (Erlotinib Hydrochloride) or DFMO or with combination therapies like FOLFIRINOX.

When the cancer being prevented or treated herein is breast cancer, the conjunctive therapy may comprise radiation, surgery, and/or administration of chemotherapeutic agents, including targeted therapies, such as Abitrexate (Methotrexate), Abraxane (Paclitaxel Albumin-stabilized Nanoparticle Formulation), Adriamycin PFS (Doxorubicin Hydrochloride), Adriamycin RDF (Doxorubicin Hydrochloride), Adrucil (Fluorouracil), Anastrozole, Arimidex (Anastrozole), Aromasin (Exemestane), Capecitabine, Clafen (Cyclophosphamide), Cyclophosphamide, Cytoxan (Cyclophosphamide), Docetaxel, Doxorubicin Hydrochloride, Efudex (Fluorouracil), Ellence (Epirubicin Hydrochloride), Epirubicin Hydrochloride, Exemestane, Fareston (Toremifene), Faslodex (Fulvestrant), Femara (Letrozole), Fluorouracil, Folex (Methotrexate), Folex PFS (Methotrexate), Fulvestrant, Gemzar (Gemcitabine Hydrochloride), Ixabepilone, Ixempra (Ixabepilone), Lapatinib Ditosylate, Letrozole, Methotrexate, Methotrexate LPF (Methotrexate), Mexate (Methotrexate), Mexate-AQ (Methotrexate), Neosar (Cyclophosphamide), Nolvadex (Tamoxifen Citrate), Novaldex (Tamoxifen Citrate), Paclitaxel, Paclitaxel Albumin-stabilized Nanoparticle Formulation, Tamoxifen Citrate, Taxol (Paclitaxel), Taxotere (Docetaxel), Toremifene, Tykerb (Lapatinib Ditosylate), or Xeloda (Capecitabine) or DFMO.

In one embodiment, a composition comprising the antitumor agents may be delivered to the subject along with another chemotherapeutic agent or therapy as is known in the art for treating the particular type of cancer. In one embodiment, the one or more anti-cancer agents described herein can be used in conjunction with other known therapeutic/cytotoxic agents. PCT application no. PCT/US10/35800 is referred to as a resource of such chemotherapeutic agents, and is incorporated herein by reference. In one embodiment, the conjunctive agent comprises one or more cytotoxic chemotherapeutic agents shown to have been mutagenic, carcinogenic and/or teratogenic, either in treatment doses in in vivo or in vitro studies. In one embodiment, the DFMO+PTI therapy could be used in combination with a checkpoint inhibitor like the PD1 inhibitors (pembrolizumab, nivolumab) and/or with PD-L1 inhibitors (atezolizumab or cemiplimab) to augment the immune response.

The mode of administration for a conjunctive formulation in accordance with the present invention is not particularly limited, provided that the composition comprising one or more of the antineoplastic agents described herein and the conjunctive agent are combined upon administration. Such an administration mode may, for example, be (1) an administration of a single formulation obtained by formulating one or more of the anti-cancer agents and the conjunctive agent simultaneously; (2) a simultaneous administration via an identical route of the two agents obtained by formulating one or more of the anti-cancer agents and a conjunctive agent separately; (3) a sequential and intermittent administration via an identical route of the two agents obtained by formulating one or more the anti-cancer agents and a conjunctive agent separately; (4) a simultaneous administration via different routes of two formulations obtained by formulating one or more of the anti-cancer agents and a conjunctive agent separately; and/or (5) a sequential and intermittent administration via different routes of two formulations obtained by formulating one or more of the anti-cancer agents and a conjunctive agent separately (for example, one or more of the anti-cancer agents followed by a conjunctive agent or its composition, or inverse order) and the like.

The dose of a conjunctive formulation may vary depending on the formulation of the one or more anti-cancer agents and/or the conjunctive agent, the subject's age, body weight, condition, and the dosage form as well as administration mode and duration. One skilled in the art would readily appreciate that the dose may vary depending on various factors as described above, and a less amount may sometimes be sufficient and an excessive amount should sometimes be required.

The conjunctive agent may be employed in any amount within the range causing no problematic side effects. The daily dose of a conjunctive agent is not limited particularly and may vary depending on the severity of the disease, the subject's age, sex, body weight and susceptibility as well as time and interval of the administration and the characteristics, preparation, type and active ingredient of the pharmaceutical formulation. An exemplary daily oral dose per kg body weight in a subject, e.g., a mammal, is about 0.001 to 2000 mg, preferably about 0.01 to 500 mg, more preferably about 0.1 to about 100 mg as medicaments, which is given usually in 1 to 4 portions.

When one or more of the anti-cancer agents and a conjunctive agent are administered to a subject, the agents may be administered at the same time, but it is also possible that the conjunctive agent is first administered and then the one or more anti-cancer agents is administered, or that the one or more anti-cancer agents is first administered and then the conjunctive agent is administered. When such an intermittent administration is employed, the time interval may vary depending on the active ingredient administered, the dosage form and the administration mode, and for example, when the conjunctive agent is first administered, the one or more anti-cancer agents may be administered within 1 minute to 3 days, preferably 10 minutes to 1 day, more preferably 15 minutes to 1 hour after the administration of the conjunctive agent. When the one or more anti-cancer agents is first administered, for example, then the one or more anti-cancer agents may be administered within 1 minute to 1 day, preferably 10 minutes to 6 hours, more preferably 15 minutes to 1 hour after the administration of the one or more anti-cancer agents.

It is understood that when referring to the one or more anti-cancer agents and a conjunctive agent, it is meant the one or more anti-cancer agents alone, a conjunctive agent alone, as a part of a composition, e.g., composition, which optionally includes one or more pharmaceutical carriers. It is also contemplated that more than one conjunctive agent may be administered to the subject if desired.

Various embodiments provide new compositions of matter and uses thereof to block the import of polyamines into cells. Various embodiments also demonstrate a use of these compounds in combination with an inhibitor of polyamine biosynthesis to starve cancer cells of the polyamine resources they need to grow. As such the combination therapy can be used to curb the growth of rapidly proliferating cell types such as cancers and infectious diseases.

Various embodiments relate to a pharmacophore having the general structure according to Formula I.

Formula I

Referring to Formula I, in general:
n may be selected from 1 and 2;
X may be selected from C and N;
Y may be selected from C and N;
$R_1$ may be selected from H, Cl, Me, and OMe;
$R_2$ may be selected from H and Me;
$R_3$ may be selected from H, F, $CF_3$, Me, OMe, and OPh;
$R_4$ may be selected from H, Cl, and Me;
$R_5$ may be selected from H, Cl, Me, and OMe;
$R_6$ may be selected from H and COOH;
$R_7$ may be selected from H and COOH;
$R_8$ may be selected from a lone pair of electrons, H, Cl, Me, OMe, OEt, OH, and $CH_2OH$;
$R_9$ may be selected from H, Cl, and Me;
$R_{10}$ may be selected from H, OH, OMe, and COMe;
$R_{11}$ may be selected from H, Cl, and Me;
$R_{12}$ may be selected from a lone pair of electrons, H, Cl, Me, OMe, OEt, OH, and $CH_2OH$;
$R_{13}$ may be selected from H and COOH; and
$R_{14}$ may be selected from H and COOH.

Still referring to Formula I, according to certain embodiments:
n may be 1;
X may be C;
Y may be C;
$R_1$ may be H;
$R_2$ may be H;
$R_3$ may be OMe;
$R_4$ may be H;
$R_5$ may be H;
$R_6$ may be selected from H and COOH;
$R_7$ may be selected from H and COOH;
$R_8$ may be selected from a lone pair of electrons, Me, OMe, OEt, OH, and $CH_2OH$;
$R_9$ may be H;
$R_{10}$ may be H;
$R_{11}$ may be selected from H, Cl, and Me;
$R_{12}$ may be a lone pair of electrons and H;
$R_{13}$ may be H; and
$R_{14}$ may be H.

Still referring to Formula I, according to certain embodiments:
n is selected from 1 and 2;
X may be N;
Y may be N;
$R_1$ may be H;
$R_2$ may be H;
$R_3$ may be selected from H and OMe;
$R_4$ may be H;
$R_5$ may be selected from H and OMe;
$R_6$ may be COOH;
$R_7$ may be H;
$R_8$ may be a lone pair of electrons;
$R_9$ may be H;
$R_{10}$ may be H;
$R_{11}$ may be H;
$R_{12}$ may be a lone pair of electrons;
$R_{13}$ may be H; and
$R_{14}$ may be H.

Still referring to Formula I, according to certain embodiments:
n may be 1;
X may be C;
Y may be C;
$R_1$ may be selected from H, $C_1$;
$R_2$ may be H;
$R_3$ may be selected from H, Me, and OMe;
$R_4$ may be H;
$R_5$ may be selected from H, $C_1$;
$R_6$ may be selected from H and COOH;
$R_7$ may be H;
$R_8$ may be selected from H, Cl, and OMe;
$R_9$ may be H;
$R_{10}$ may be H;
$R_{11}$ may be H;
$R_{12}$ may be selected from H, Cl, and OMe;
$R_{13}$ may be H; and
$R_{14}$ may be selected from H and COOH.

Various embodiments relate to a pharmacophore having the general structure according to Formula II.

Formula II

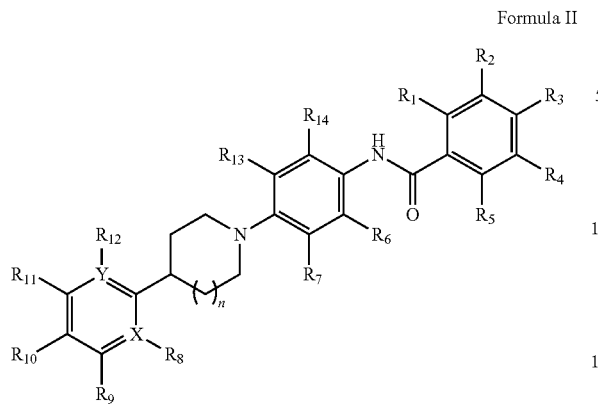

Formula III

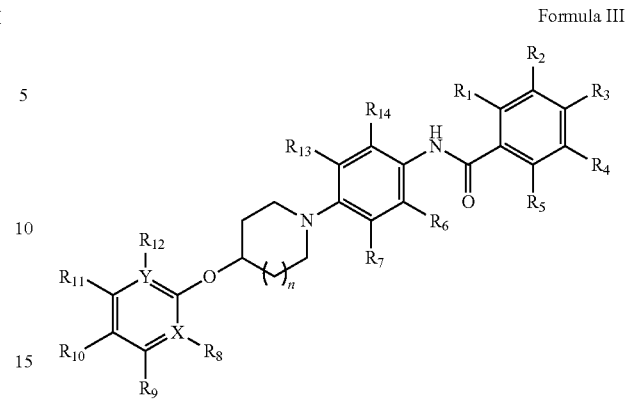

Referring to Formula II, in general:
n may be selected from 1 and 2;
X may be selected from C and N;
Y may be selected from C and N;
$R_1$ may be selected from H, Cl, Me, and OMe;
$R_2$ may be selected from H and Me;
$R_3$ may be selected from H, Me, and OMe;
$R_4$ may be selected from H and Me;
$R_5$ may be selected from H, Cl, Me, and OMe;
$R_6$ may be selected from H and COOH;
$R_7$ may be selected from H and COOH;
$R_8$ may be selected from a lone pair of electrons, H, Cl, Me, OMe, OEt, OH, and $CH_2OH$;
$R_9$ may be selected from H, Cl, and Me;
$R_{10}$ may be selected from H, O, OMe, and COMe;
$R_{11}$ may be selected from H, Cl, and Me;
$R_{12}$ may be selected from a lone pair of electrons, H, Cl, Me, OMe, OEt, OH, and $CH_2OH$;
$R_{13}$ may be selected from H and COOH; and
$R_{14}$ may be selected from H and COOH.

Still referring to Formula II, according to certain embodiments:
n may be 1;
X may be C;
Y may be C;
$R_1$ may be selected from H and OMe;
$R_2$ may be H;
$R_3$ may be H;
$R_4$ may be H;
$R_5$ may be selected from H and OMe;
$R_6$ may be COOH;
$R_7$ may be H;
$R_8$ may be H;
$R_9$ may be H;
$R_{10}$ may be H;
$R_{11}$ may be H;
$R_{12}$ may be H;
$R_{13}$ may be H; and
$R_{14}$ may be H.

Various embodiments relate to a pharmacophore having the general structure according to Formula III.

Referring to Formula III, in general:
n may be selected from 1 and 2;
X may be selected from C and N;
Y may be selected from C and N;
$R_1$ may be selected from H, Cl, Me, and OMe;
$R_2$ may be selected from H and Me;
$R_3$ may be selected from H, Me, and OMe;
$R_4$ may be selected from H and Me;
$R_5$ may be selected from H, Cl, Me, and OMe;
$R_6$ may be selected from H and COOH;
$R_7$ may be selected from H and COOH;
$R_8$ may be selected from a lone pair of electrons, H, Cl, Me, OMe, OEt, OH, and $CH_2OH$;
$R_9$ may be selected from H, Cl, and Me;
$R_{10}$ may be selected from H, O, OMe, and COMe;
$R_{11}$ may be selected from H, Cl, and Me;
$R_{12}$ may be selected from a lone pair of electrons, H, Cl, Me, OMe, OEt, OH, and $CH_2OH$;
$R_{13}$ may be selected from H and COOH; and
$R_{14}$ may be selected from H and COOH.

Still referring to Formula III, according to certain embodiments:
n may be 1;
X may be C;
Y may be C;
$R_1$ may be selected from H and OMe;
$R_2$ may be H;
$R_3$ may be H;
$R_4$ may be H;
$R_5$ may be selected from H and OMe;
$R_6$ may be COOH;
$R_7$ may be H;
$R_8$ may be H;
$R_9$ may be H;
$R_{10}$ may be H;
$R_{11}$ may be H;
$R_{12}$ may be H;
$R_{13}$ may be H; and
$R_{14}$ may be H.

Various embodiments relate to a compound having the structure, according to Formula IV:

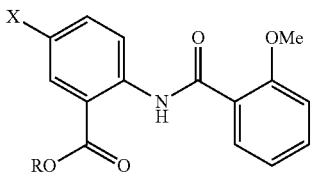

Formula IV

Referring to Formula IV, according to various embodiments, R may be selected from H, Me or Et or isopropyl or represents the counter-ion of a pharmaceutically acceptable salt like a carboxylate salt containing Na+ or K+. In general, X may be selected from the group consisting of H, a heteroatom, an alkyl, an alkylaryl, a dialkylamine, and a heterocycle. According to various embodiments, X may be a heterocycle selected from the group consisting of (connected at the wavy bond line):

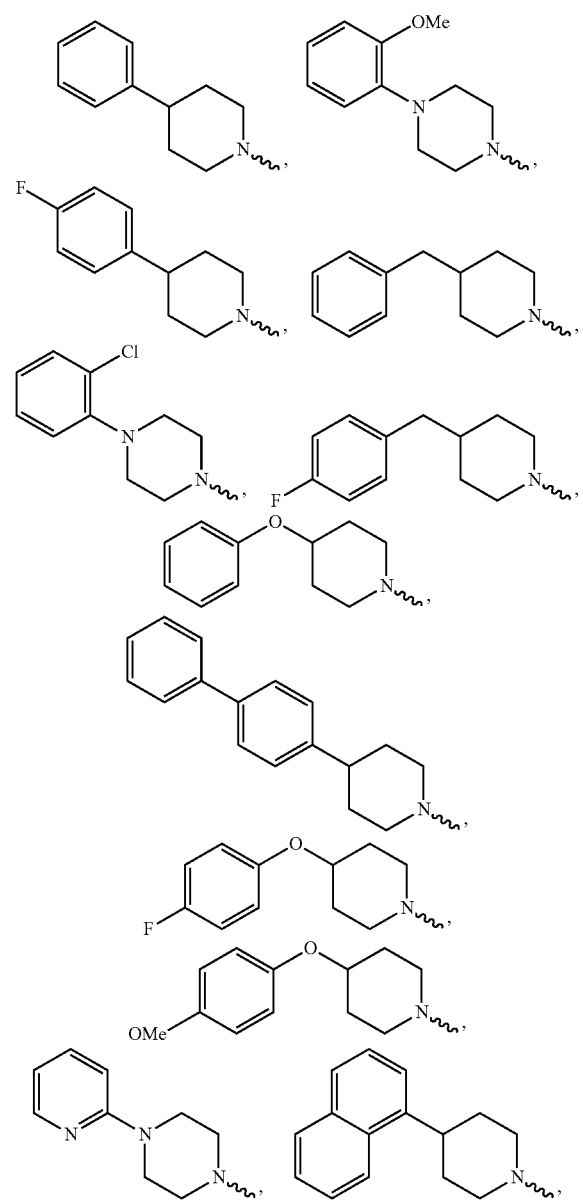

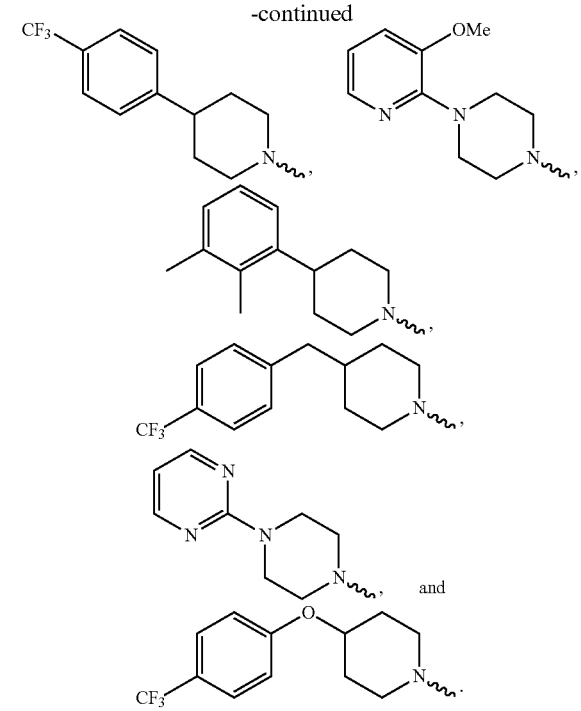

Still referring to Formula IV, according to various embodiments, the heterocycle may include a nitrogen-containing aromatic ring, and the heterocycle may be bonded to the compound via a nitrogen atom in the nitrogen-containing aromatic ring. According to various other embodiments, X may be a hydrogen atom. According to various embodiments, X may be a heteroatom. For example, the heteroatom may be F, Cl, Br, or I. According to various embodiments, X may be an alkyl chain. The alkyl chain may be any suitable length, for example a $C_1$-$C_{10}$ alkyl chain. For example, the alkyl chain may be methyl, ethyl, propyl, n-propyl, isopropyl, butyl, n-butyl, isobutyl, sec-butyl, pentyl, n-pentyl, 2-methylbutyl, isopentyl. According to various embodiments, X may be an alkylaryl chain. The alkyl aryl chain may include one ore more alkyl chains. Each alkyl chain may be any suitable length, for example a $C_1$-$C_{10}$ alkyl chain. The alkyl chains may or may not have the same length. For example, the alkylaryl chain may be a benzyl, a phenethyl, or a dialkylamino. The dialkylamino may be a dimethylamino or a diethylamino group, for example. According to various embodiments X may be a dialkylamine. The dialkylamine may be, for example, $NMe_2$, $NEt_2$, $N^4$-methylpiperazinyl, $N^4$-ethylpiperazinyl, $N^4$-propylpiperazinyl, $N^4$-butylpiperazinyl, $N^4$-isopropylpiperazinyl, $N^4$-isobutylpiperazinyl, or $N^4$-isopentylpiperazinyl.

Various embodiments relate to a compound having the structure according to Formula V:

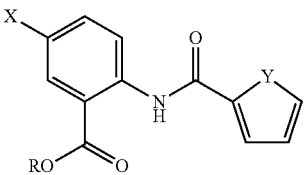

Formula V

Referring to Formula V, according to various embodiments, R may be selected from H, Me or Et or isopropyl or represents the counter-ion of a pharmaceutically acceptable salt like a carboxylate salt containing Na+ or K+. According to various embodiments, Y may be selected from either CH$_2$, NH, O, S, N—Me, N—Ac, N—Bn or N—Bz. In general, X may be selected from the group consisting of H, a heteroatom, an alkyl, an alkylaryl, a dialkylamine, and a heterocycle. According to various embodiment, X may be a heterocycle selected from the group consisting of (connected at the wavy bond line):

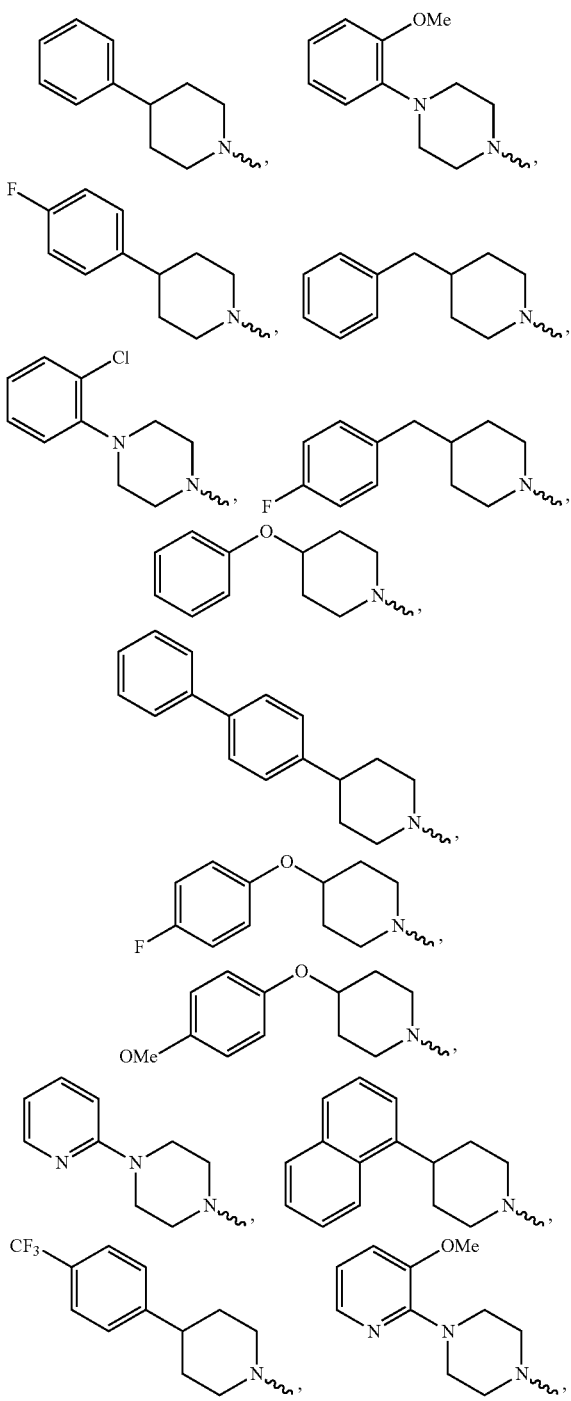

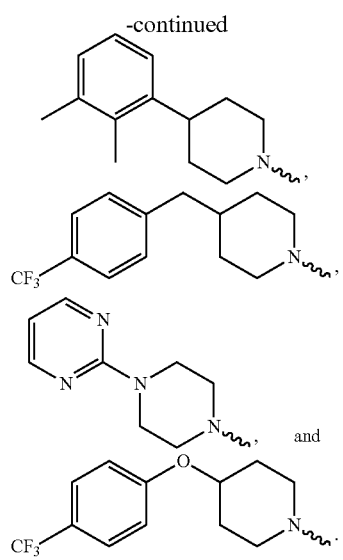

Still referring to Formula V, according to various embodiments, the heterocycle may include a nitrogen-containing aromatic ring, and the heterocycle may be bonded to the structure via a nitrogen atom in the nitrogen-containing aromatic ring. According to various other embodiments, X may be a hydrogen atom. According to various embodiments, X may be a heteroatom. For example, the heteroatom may be F, Cl, Br, or I. According to various embodiments, X may be an alkyl chain. The alkyl chain may be any suitable length, for example a $C_1$-$C_{10}$ alkyl chain. For example, the alkyl chain may be methyl, ethyl, propyl, n-propyl, isopropyl, butyl, n-butyl, isobutyl, sec-butyl, pentyl, n-pentyl, 2-methylbutyl, isopentyl. According to various embodiments, X may be an alkylaryl chain. The alkyl aryl chain may include one ore more alkyl chains. Each alkyl chain may be any suitable length, for example a $C_1$-$C_{10}$ alkyl chain. The alkyl chains may or may not have the same length. For example, the alkylaryl chain may be a benzyl, a phenethyl, or a dialkylamino. The dialkylamino may be a dimethylamino or a diethylamino group, for example. According to various embodiments X may be a dialkylamine. The dialkylamine may be, for example, NMe$_2$, NEt$_2$, N$^4$-methylpiperazinyl, N$^4$-ethylpiperazinyl, N$^4$-propylpiperazinyl, N$^4$-butylpiperazinyl, N$^4$-isopropylpiperazinyl, N$^4$-isobutylpiperazinyl, or N$^4$-isopentylpiperazinyl.

Various embodiments relate to a compound having the structure, according to Formula VI

Formula VI

Referring to Formula VI, according to various embodiments, R may be selected from H, Me or Et or isopropyl or represents the counter-ion of a pharmaceutically acceptable salt like a carboxylate salt containing Na+ or K+. According to various embodiments, Y may be selected from either CH$_2$, NH, O, S, N—Me, N—Ac, N—Bn or N—Bz. In general, X may be selected from the group consisting of H, a heteroatom, an alkyl, an alkylaryl, a dialkylamine, and a heterocycle. According to various embodiment, X may be a heterocycle selected from the group consisting of (connected at the wavy bond line):

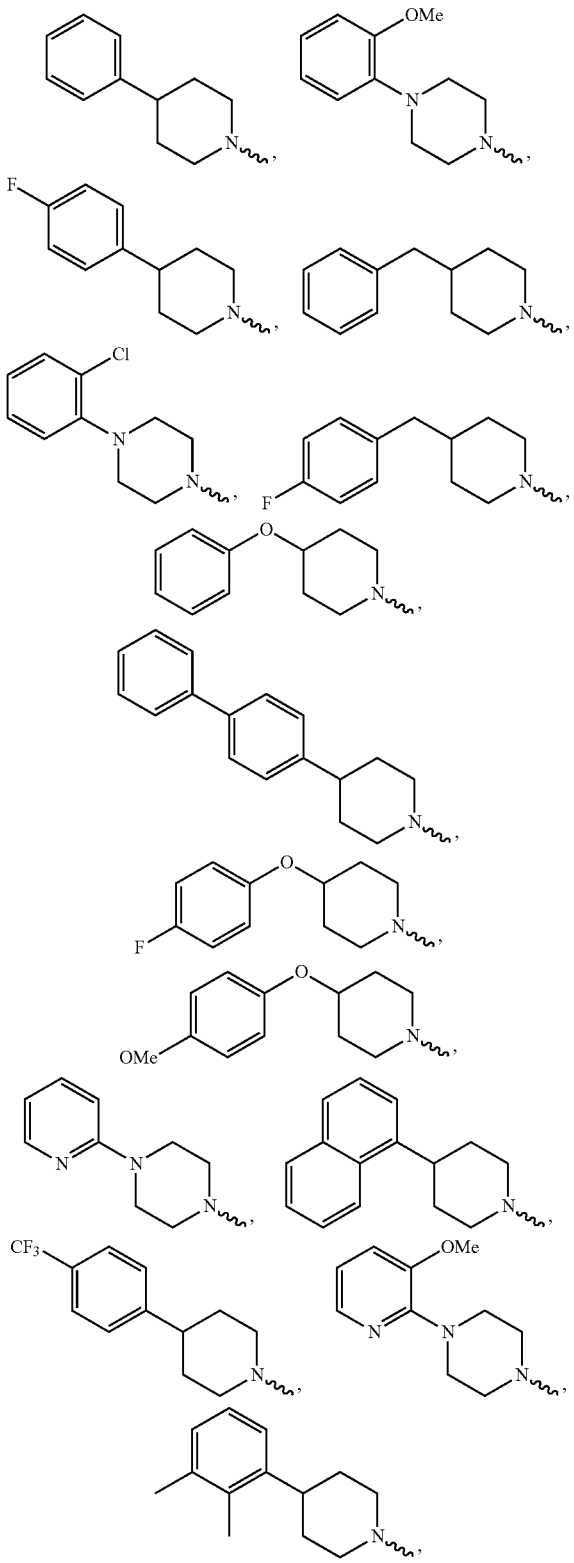

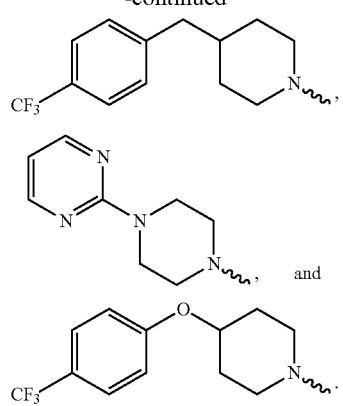

Still referring to Formula VI, according to various embodiments, the heterocycle may include a nitrogen-containing aromatic ring, and the heterocycle may be bonded to the structure via a nitrogen atom in the nitrogen-containing aromatic ring. According to various other embodiments, X may be a hydrogen atom. According to various embodiments, X may be a heteroatom. For example, the heteroatom may be F, Cl, Br, or I. According to various embodiments, X may be an alkyl chain. The alkyl chain may be any suitable length, for example a $C_1$-$C_{10}$ alkyl chain. For example, the alkyl chain may be methyl, ethyl, propyl, n-propyl, isopropyl, butyl, n-butyl, isobutyl, sec-butyl, pentyl, n-pentyl, 2-methylbutyl, isopentyl. According to various embodiments, X may be an alkylaryl chain. The alkyl aryl chain may include one ore more alkyl chains. Each alkyl chain may be any suitable length, for example a $C_1$-$C_{10}$ alkyl chain. The alkyl chains may or may not have the same length. For example, the alkylaryl chain may be a benzyl, a phenethyl, or a dialkylamino. The dialkylamino may be a dimethylamino or a diethylamino group, for example. According to various embodiments X may be a dialkylamine. The dialkylamine may be, for example, $NMe_2$, $NEt_2$, $N^4$-methylpiperazinyl, $N^4$-ethylpiperazinyl, $N^4$-propylpiperazinyl, $N^4$-butylpiperazinyl, $N^4$-isopropylpiperazinyl, $N^4$-isobutylpiperazinyl, or $N^4$-isopentylpiperazinyl.

According to various embodiments, Z may be a heterocycle selected from

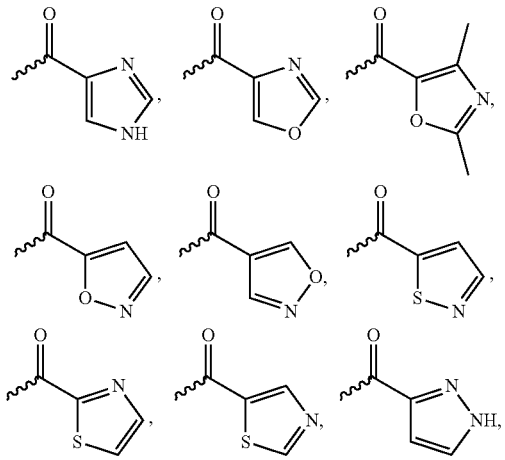

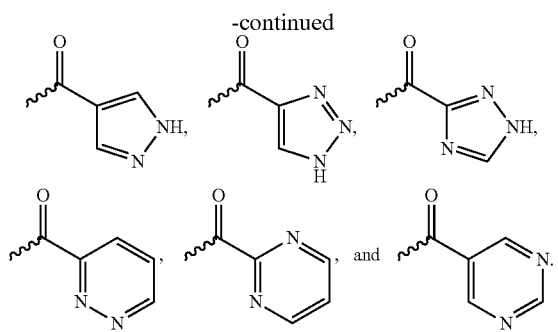

Alternatively, Z may contain an alkyl linker in lieu of the carbonyl linker and may be selected from:

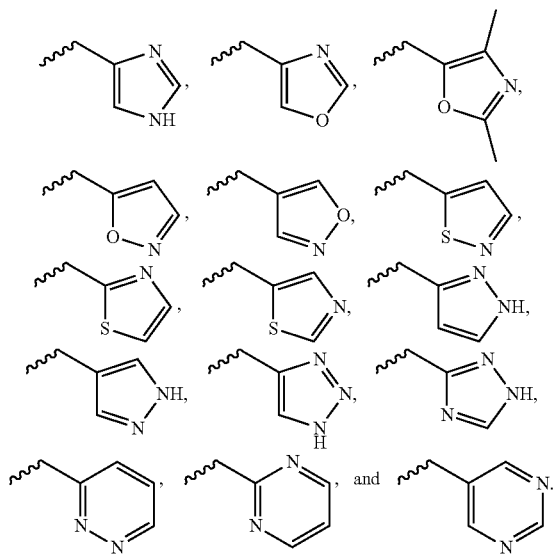

Various embodiments relate to methods for preventing or treating a cancer in a subject, the method comprising: administering to a subject a composition according to any of the embodiments described herein in an amount effective to inhibit metastatic activity or tumor growth in the subject.

EXAMPLES

Materials

CHO-K1 cells were from ATCC. DFMO, aminoguanidine and spermidine were from Sigma. 0.25% Trypsin, 100× Penicillin/Streptomycin (P/S), 100× l-glutamine, RPMI and phenol free RPMI were from GIBCO. Dulbecco's PBS (PBS) was from Corning.

Heat inactivated fetal bovine serum (FBS) was from Hyclone. ATPLite was from Perkin Elmer. $N^1$-(9-anthracenylmethyl)-homospermidine (Ant44) was synthesized and provided by the Phanstiel lab at UCF. 384-well white plates were from Greiner, 1536-well white plates were from Aurora.

Methods (1536-Well Assays, HTS Phase of the Project)

Ant44 Assay (Primary Screening Assay)

CHO K1 cells were grown in growth medium (RPMI+ 10% FBS+1×P/S+1% l-glutamine) to 70% confluency, washed in PBS and trypsinized. Cells were plated in assay medium (serum free RPMI+2% FBS+1× l-glutamine+1× P/S+300 mM aminoguanidine) at 50000 cells/mL for 200 cells per well in 4 ul using a Thermo Multidrop Combi into a 1536-well white Aurora plate. Cells were spun at 100×g for 1 minute and incubated at 37° C. in a humidified $CO_2$ incubator for 24 hours. 10 nL of 10 mM test compound was then dispensed with a Labcyte Echo 555 acoustic dispenser for a final assay concentration (FAC) of 20 uM followed by 1 ul of 10 uM Ant44 (FAC 2 uM) in assay medium added with a Beckman BioRAPTR FRD dispenser or 1 ul of cells added in assay medium (positive control). The plates were spun at 200×g for 1 minute and incubated at 37° C. in a humidified 5% $CO_2$ incubator for 48 hours. Cellular ATP content (cell viability) was then assayed by adding 3 ul of ATPLite with a Beckman BioRAPTR FRD dispenser and incubated for 10' at room temperature. Plates were spun at 200×g for 1 minute and read on a Perkin Elmer Viewlux multimode plate reader using luminescence mode. In the primary HTS assay compounds were run as singletons with an average z' of 0.62. In the reconfirmation assay, compounds were run in quadruplicate with an average z' of 0.56.

DFMO/Spermidine Assay

CHO K1 cells were grown in growth medium to 70% confluency and washed in PBS and trypsinized. Cells were plated in assay medium at 15000 cells/mL for 60 cells per well using a Thermo Multidrop Combi in 4 ul into a 1536-well white Aurora plate. Cells were spun at 100×g for 1 minute and incubated at 37° C. in a humidified $CO_2$ incubator for 24 hours. 10 nL of 10 mM test compound was then dispensed with a Labcyte Echo 555 acoustic dispenser for a final assay concentration of 20 uM followed by 1 uL of 5 mM DFMO and 5 uM spermidine (FAC 5 mM DFMO and 1 uM spermidine) added in assay medium with a Beckman BioRAPTR FRD dispenser or 1 uL of 5 mM DFMO added in assay medium (positive control). The plates were spun at 200×g for 1 minute and incubated at 37° C. in a humidified 5% $CO_2$ incubator for 48 hours. Cellular ATP content (cell viability) was then assayed by adding 3 μL of ATPLite with a Beckman BioRAPTR FRD dispenser and incubated for 10 min at room temperature. Plates were spun at 200×g for 1 minute and read on a Perkin Elmer Viewlux multimode plate reader using luminescence mode. In the reconfirmation assay compounds were run in quadruplicate. The average z' was 0.24. A PTI compound is expected to block the entry or disrupt the intracellular trafficking of spermidine and inhibit the ability of spermidine to rescue the growth or viability of DFMO treated cells.

Cytotoxicity

CHO K1 cells were grown in growth medium to 70% confluency and washed in PBS and trypsinized. Cells were plated in assay medium at 15625 cells/mL for 62 cells per well using a Thermo Multidrop Combi in 4 uL into a 1536-well white Aurora plate. Cells were spun at 100×g for 1 minute and incubated at 37° C. in a humidified $CO_2$ incubator for 24 hours. 10 nL of test compound was then dispensed with a Labcyte Echo 555 acoustic dispenser for a final assay concentration (FAC) of 20 μM followed by adding 1 uL of assay medium with a Beckman BioRAPTR FRD dispenser, spun at 200×g for 1 minute and incubated at 37° C. in a humidified 5% $CO_2$ incubator for 48 hours. Cellular ATP content was then assayed by adding 3 uL of ATPLite with a Beckman BioRAPTR FRD dispenser and incubated for 10 minutes at room temperature. Plates were spun at 200×g for 1 minute and read on a Perkin Elmer Viewlux multimode plate reader using luminescence mode. This assay was used for testing dose-response of dry powders.

384-Well HTL Assays (Dose Response Only)

Please note that the Envision is used for the 384-well assays because the Viewlux luminescence signal was saturated.

Ant44 Assay

Ant44 is a cytotoxic polyamine, i.e., $N^1$-(9-anthracenyl)-homospermidine. A non-toxic PTI compound would block entry or intracellular trafficking of the Ant44 toxin and rescue the cells back to high viability. Therefore, this screen tested for compounds which rescued cells from Ant44 toxicity. CHO K1 cells were grown in growth medium to 70% confluency and washed in PBS and trypsinized. Cells were plated in assay medium at 20000 cells/ml for 400 cells per well using a Thermo Multidrop Combi in 20 uL into a white Greiner plate. Cells were spun at 100×g for 1 minute and incubated at 37° C. in a humidified $CO_2$ incubator for 24 hours. 15, 30 or 60 nL of 0.31, 2.5 or 20 mM test compound was then dispensed with a Labcyte Echo 555 acoustic dispenser for a final assay concentration range of 0.156-20 uM (1 to 2 dilutions). This was followed by adding 10 uL of 10 uM Ant44 (FAC 2 uM) in assay medium with a Beckman BioRAPTR FRD dispenser or 10 uL of cells added in assay medium (positive control). The plates were spun at 200×g for 1 minute and incubated at 37° C. in a humidified 5% $CO_2$ incubator for 48 hours. Cellular ATP content was then assayed by adding 20 μL of ATPLite with a Beckman BioRAPTR FRD dispenser and incubated for 10' at room temperature. Plates were spun at 200×g for 1 minute and read on a Perkin Elmer Envision multimode plate reader using luminescence mode. Duplicates were run for each compound concentration, and the curves represent the average of the duplicates as percent activity (rescuing the cells from Ant44 toxicity, 100% activity=100% viability). The average z' was 0.54.

DFMO/Spermidine Assay

Here cells were treated with an inhibitor of polyamine biosynthesis (DFMO) and rescued back to high viability by the presence of exogenous polyamine (spermidine). Putative PTI compounds were screened for their ability to block the entry or intracellular trafficking of exogenous spermidine (or otherwise disrupt the intracellular trafficking of spermidine) by measuring cell viability in the presence of DFMO+ spermidine+PTI compound. A non toxic PTI compound should give a viability reading similar to the DFMO only control even though spermidine is present (because it blocks uptake of the rescuing dose of spermidine or disrupts its intracellular trafficking). CHO-K1 cells were grown in growth medium to 70% confluency and washed in PBS and trypsinized. Cells were plated in assay medium at 10000 cells/mL for 200 cells per well using a Thermo Multidrop Combi in 20 uL into a white Greiner plate. Cells were spun at 100×g for 1 minute and incubated at 37° C. in a humidified $CO_2$ incubator for 24 hours. 15, 30 or 60 nL of 0.31, 2.5 or 20 mM test compound was then dispensed with a Labcyte Echo 555 acoustic dispenser for a final assay concentration range of 0.156-20 μM (1 to 2 dilutions). This was followed by adding 10 μL of 5 mM DFMO and 5 μM spermidine (FAC 5 mM DFMO and 1 μM spermidine) in assay medium with a Beckman BioRAPTR FRD dispenser or 10 μL of 5 mM DFMO added in assay medium (positive control). The plates were spun at 200×g for 1 minute and incubated at 37° C. in a humidified 5% $CO_2$ incubator for 48 hours. Cellular ATP content was then assayed by adding 20 uL of ATPLite with a Beckman BioRAPTR FRD dispenser and incubated for 10 min at room temperature. Plates were spun at 200×g for 1 minute and read on a Perkin Elmer Envision multimode plate reader using luminescence mode. Duplicates were run for each compound concentration, and the curves represent the average of the duplicates as percent activity (DFMO-induced cell death from competition of the PTI with spermidine). The average z' was 0.34. A PTI compound is expected to block the entry or disrupt the intracellular trafficking of spermidine and inhibit the ability of spermidine to rescue the growth or viability of DFMO treated cells Cytotoxicity CHO K1 cells were grown in growth medium to 70% confluency and washed in PBS and trypsinized. Cells were plated in assay medium at 10000 cells/mL for 200 cells per well using a Thermo Multidrop Combi in 20 uL into a white Greiner plate. Cells were spun at 100×g for 1 minute and incubated at 37° C. in a humidified $CO_2$ incubator for 24 hours. 15, 30 or 60 nL of 0.31, 2.5 or 20 mM test compound stock was then dispensed with a Labcyte Echo 555 acoustic dispenser for a final assay concentration range of 0.156-20 μM (1 to 2 dilutions). This was followed by adding by 10 μL of assay medium to all wells with a Beckman BioRAPTR FRD dispenser. The plates were spun at 200×g for 1 minute and incubated at 37° C. in a humidified 5% $CO_2$ incubator for 48 hours. Cellular ATP content was then assayed by adding 20 μL of ATPLite with a Beckman BioRAPTR FRD dispenser and incubated for 10 min at room temperature. Plates were spun at 200×g for 1 minute and read on a Perkin Elmer Envision for multimode plate reader using luminescence mode. Duplicates were run for each compound concentration, and the curves represent the average of the duplicates as percent viability.

Example 1

Having developed two orthogonal assays to identify polyamine transport inhibitors, 322,716 compounds were screened for their ability to block the 48 h uptake of a cytotoxic polyamine probe (Ant44, 2 μM) into Chinese hamster ovary (CHO) cells. The final compound concentration was either 20 μM or 10 μg/mL (depending upon the compound source). A successful PTI in Assay 1 would block the uptake of the toxic Ant44 probe and rescue the cells back to >90% relative growth vs an untreated control. It was critical to also evaluate the toxicity of the PTI by itself as a toxic PTI would give a false negative in Assay1 (and a false positive in Assay 2). As such the data from each assay was only considered valid if the compound when tested alone at the same concentration gave a relative % growth of >90% (i.e., was non-toxic). 1028 compounds met the criteria for promotion from Assay 1 to Assay 2, (e.g., a 0.3% hit rate). However, when these were retested in the primary assay again only 362 reconfirmed in the primary assay. These reconfirmed 362 compounds were then promoted to Assay 2. Assay 2 then evaluated the ability of the compound to inhibit the uptake of a rescuing dose of Spermidine (Spd, 1 μM) into DFMO-treated CHO cells. Here the DFMO was dosed at its 48 h $IC_{50}$ concentration (4.2 mM in CHO cells) with and without the rescuing dose of spermidine. DFMO alone gave 50% viability whereas the DFMO+Spd control gave ~95% viability. A successful PTI was expected to block the rescuing dose of spermidine from entering cells (or block its intracellular trafficking) and give a relative growth % somewhere between the DFMO and DFMO+Spd controls. Of the 362 compounds tested in quadruplicate 138 compounds had an average activity of 40%, these were then triaged by medicinal chemists to provide 80 compounds of interest. Powders were then ordered and these tested again via dose response experiments in both assays.

Of these additional screens piperazinyl benzoic acid derivatives were found to be valid PTI compounds and are the subject of this patent disclosure. Table 1 shows top hits from the HTS screening.

TABLE 1

| DFMO Assay (μM) | DFMO hit structures | Ant44 (μM) | Ant44 hit structures |
|---|---|---|---|
| SBI-0801308.001 (IC50 10-20 μM, tox >20 μM) | | SBI-0801308.001 (5-10 μM EC50) Tox >31 μM | |
| SBI-0351221.0002 (IC50 ~10), toxic >10 | | SBI-0351221.0002 (10 EC50) Tox >10 | |
| SBI-0800670.0001 (IC50 ~10-15), tox >15 | | SBI-0800670.0001 (20 EC50) Tox >20 | |

TABLE 1-continued

| DFMO Assay (μM) | DFMO hit structures | Ant44 (μM) | Ant44 hit structures |
|---|---|---|---|
| SBI-0800676.0001 (IC50 ~15, tox >15) | | SBI-0800676.0001 (20 EC50) Tox >20 | |
| SBI-0800678.0001 (IC50 ~15-25, tox >15) | | SBI-0800678.0001 (20 EC50) Tox >20 | |
| SBI-0800683.0001 (IC50 ~20 μM, tox >20 μM) | | SBI-0800683.0001 (20 μM EC50) Tox >20 μM | |
| SBI-0800675.0001 (IC50 >25, no tox) | | SBI-0800675.0001 (31 EC50) Tox >31 | |

TABLE 1-continued

| DFMO Assay (μM) | DFMO hit structures | Ant44 (μM) | Ant44 hit structures |
|---|---|---|---|
| SBI-0800674.0001 (IC50 ~5, tox >10) | | SBI-0800674.0001 (no effect, tox after 5) | |
| SBI-0800680.0001 IC50 >31, no tox Rel poor potency | | SBI-0800680.0001 31 EC50 but some tox near 5? | |
| SBI-0800691.0001 No effect, poor potency, No tox | | SBI-0800691.0001 (10-15 EC50) No tox | |
| SBI-0800679.0001 (Ic50 10-15 μM, tox >15 μM) | | SBI-0800679.0001 EC40 near 20 μM, Tox >20 μM) | |

TABLE 1-continued
| DFMO Assay (μM) | DFMO hit structures | Ant44 (μM) | Ant44 hit structures |
|---|---|---|---|
| SBI-0800682.0001 IC50 10-15, tox >10) | 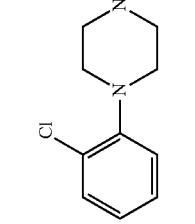 | SBI-0800682.0001 Tox >20, EC40 near 15 | 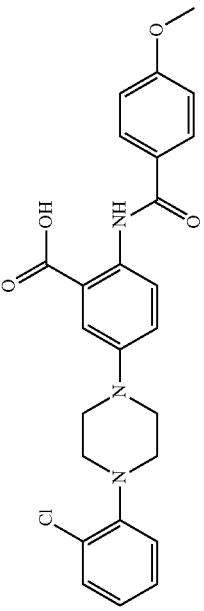 |
| SBI-0800686.0001 (IC50 ~5, tox >5) | 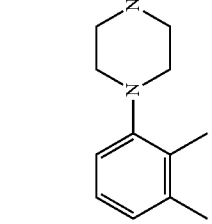 | SBI-0800686.0001 Tox >10, EC50 near 10 | 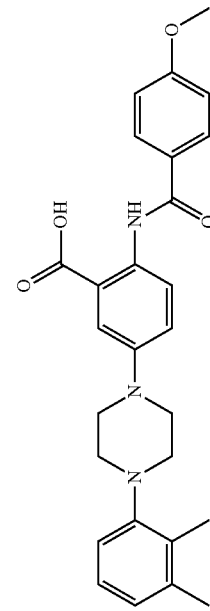 |
| SBI-0800692.0001 (IC50 ~20, tox >20) |  | SBI-0800692.0001 (EC40 at 31) | 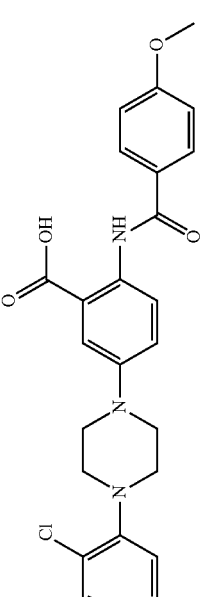 |
| SBI-0800690.0001 (IC50 ~20, tox >20) |  | SBI-0800690.0001 No effect | 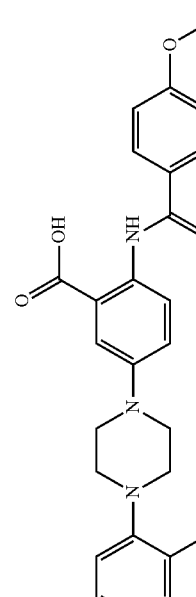 |

TABLE 1-continued

| DFMO Assay (μM) | DFMO hit structures | Ant44 (μM) | Ant44 hit structures |
|---|---|---|---|
| SBI-0800693.0001 (Ic50 ~10 μM, tox >10 μM) | | SBI-0800693.0001 (NO EFFECT) | |
| SBI-0800661.0001 (EC50 >20) | | SBI-0800661.0001 No effect | |
| SBI-0800662.0001 (IC50 ~5) | | SBI-0800662.0001 No effect | |
| SBI-0800666.0001 (IC50 ~20-32) | | SBI-0800666.0001 No effect | |

TABLE 1-continued

| DFMO Assay (μM) | DFMO hit structures | Ant44 (μM) | Ant44 hit structures |
|---|---|---|---|
| SBI-0800669.0001 (IC50 ~2-5), tox >10 | (structure) | SBI-0800669.0001 No effect | (structure) |
| SBI-0801324.0001 IC40 at 31 μM, Non tox, | (structure) | SBI-0801324.0001 EC50 at 31 μM | (structure) |
| SBI-0754480.0001 IC50 5-10 μM, tox >20 μM | (structure) | SBI-0754480.0001 (31 μM EC50) | (structure) |

Example 2

The initial hits from Example 1 were then focused via a small structure activity study and the results shown below. The EC50 value in the Ant44 assay (Assay 1) was the concentration of the compound needed to reach 50% of the way between the Ant44 only control (50% rel growth) and the untreated control (100% rel growth), i.e. 75% relative growth in the presence of the Ant44 compound. In Assay 2, the EC50 value is the concentration of the compound needed to reach 50% of the way between the % relative growth values established by the DEMO only control (50% relative growth) and the DFMO+Spd control (100% rel growth), i.e. 75% relative growth in the presence of DFMO+Spd. Table 2 summarizes DFMO+Spd rescue assay top hits. Table 3 summarizes Ant44 assay top hits.

TABLE 2

| Compound | Compd # | CHO EC50 DFMO rescue (μM) | CHO MTD (μM) | Active in Ant44 assay? | L3.6pl EC50 (μM) | L3.6pl MTD (μM) |
|---|---|---|---|---|---|---|
| [structure: 4-phenylpiperidine linked to benzene with COOH and NHC(O)-2-methoxyphenyl] | SBI-0814418 | 21 | >32 | Yes in CHO EC50 is 19, no in L3.6pl (too toxic) | 5 | 5, at 10 μM (80%) |
| [structure: 2-pyridylmethyl-piperazine linked to benzene with COOH and NHC(O)-2-methoxyphenyl] | SBI-0814421 | 20 | >20 | No in CHO | >10 | 10 |
| [structure: 2-methoxyphenyl-piperazine linked to benzene with COOH and NHC(O)-4-methoxyphenyl] | SBI-0800678 | ~25 | >32 | Yes in CHO EC50 is ~20 uM | | |
| [structure: 2-ethoxyphenyl-piperazine linked to benzene with COOH and NHC(O)-4-methoxyphenyl] | SBI-0800683 | ~20 | 20 | Yes in CHO EC50 is ~20 uM | | |

TABLE 2-continued

| Compound | Compd # | CHO EC50 DFMO rescue (μM) | CHO MTD (μM) | Active in Ant44 assay? | L3.6pl EC50 (μM) | L3.6pl MTD (μM) |
|---|---|---|---|---|---|---|
| *(structure: 3-(o-tolyl)pyrrolidine linked to benzene with COOH and NHC(O)-C6H4-OMe)* | SBI-0800687 | 32 | >32 | No | | |
| *(structure: 4-phenylpiperazine linked to benzene with COOH and NHC(O)-C6H4-OMe)* | SBI-0800679 | 10 | 10 | Yes but EC50 > 10 in CHO | | |

Table 3 summarizes Ant44 assay top hits.

TABLE 3

| Compound | Compd # | Active in DFMO assay? | Ant44 rescue EC50 CHO (μM) | MTD CHO (μM) | Ant44 rescue EC50 L3.6pl (μM) | MTD L3.6pl (μM) |
|---|---|---|---|---|---|---|
| *(structure: 4-(pyridin-2-yl)piperazine linked to benzene with COOH and NHC(O)-furan)* | SBI-0814419 | No in CHO and in L3.6pl | >32 | >32 | 10 | >20 |
| *(structure: 1-(pyrimidin-2-yl)-1,4-diazepane linked to benzene with COOH and NHC(O)-C6H4-OMe)* | SBI-0800691 | No in CHO | ~11 | >32 | | |

TABLE 3-continued

| Compound | Compd # | Active in DFMO assay? | Ant44 rescue EC50 CHO (μM) | MTD CHO (μM) | Ant44 rescue EC50 L3.6pl (μM) | MTD L3.6pl (μM) |
|---|---|---|---|---|---|---|
| 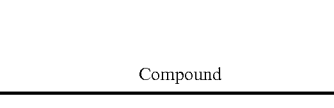 | SBI-0801308 | No in CHO | 10 | ~10 | | |

Example 3

The purpose of this example was to identify non-toxic PTIs that prevent spermidine rescue of DFMO-challenged CHO cells. Of additional interest was to identify PTIs that protect CHO cells by blocking uptake of a toxic polyamine, Ant44, through possibly a separate polyamine transporter or a different intracellular trafficking step.

From the scaffolds presented, it was decided that the chemistry focus on the diaryl piperazine scaffold represented by SBI-0754479 in FIG. 1. The plan was to investigate multiple regions of the scaffold in order to improve inhibition of the polyamine transport system while avoiding general cytotoxicity.

Figure 2:
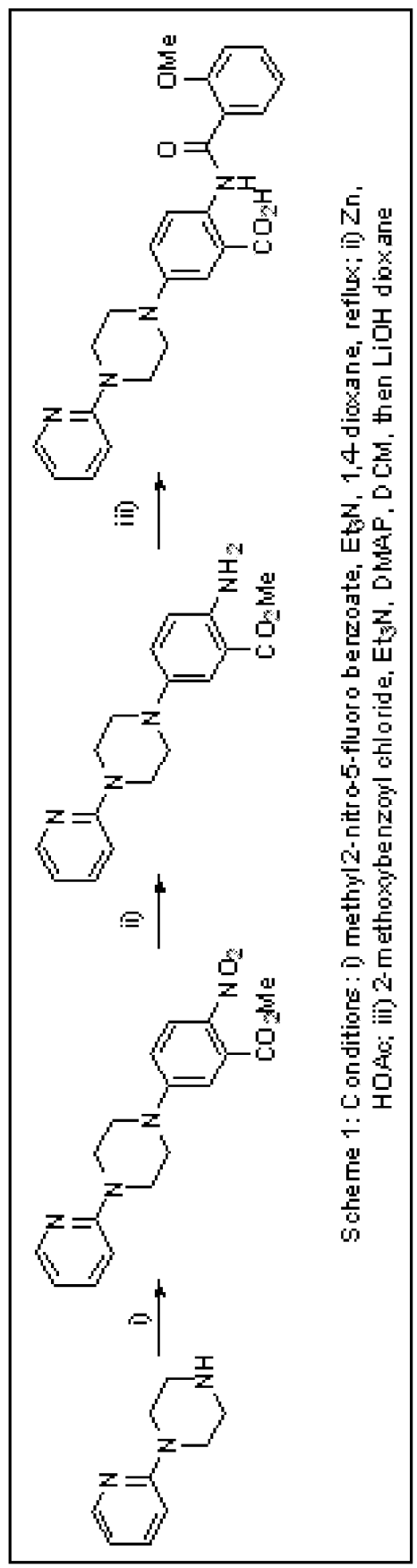
FIG. 2: is an example according to various embodiments illustrating a reaction pathway including structural diagrams of compounds according to various embodiments.

The initial round of SAR was primarily fueled by 38 compounds, which were purchased from commercial vendors (ChemDiv) while a robust synthetic route was under development. Subsequent SAR was derived from the approximately 20 synthesized compounds. A general synthetic route developed to provide diaryl piperazines is represented in Scheme 1, also shown in FIG. 2. Substituted piperazines were added to the active fluoro-bearing carbon of the nitro benzoates to provide the core diarylpiperazine motif. Reduction of the nitro group afforded the aniline which could be N-benzoylated. Finally, the esters were hydrolyzed to yield the free carboxylate moiety.

Throughout the SAR, many analogs with desired target activity (DFMO assay) also proved to be cytotoxic at or about the same calculated $IC_{50}$S. In the manner in which the assay is performed, general toxicity would present a false positive response. Thus, it was critical that positive hits in the DFMO assay be non-toxic. To this end, compounds were also screened for their cytotoxicity in parallel experiments. Table 4A provides structures of the compounds represented in Table 4B. Several examples represented in Table 4B indicates the possibility of divergent SAR. The presence of a phenyl piperidine instead of aryl piperazine (SBI-0814418) lead to modest activity in both DFMO and Ant44 assays without general toxicity. The compound also demonstrated micromolar activity, when the DFMO assay was run in the L3.6 pl pancreatic cancer cell line. A similar modification with phenyl pyrrolidine (SBI-0800687) showed similar, albeit weaker activity in the CHO cell assays. Insertion of a methylene between the 2-pyridyl and the piperazine (SBI-0814421) showed some level of activity in the DFMO assay. A comparison between SBI-0800678 and SBI-0800683 indicates lengthening a methoxy to an ethoxy increases cytotoxicity. The unsubstituted phenyl piperazine (SBI-0800679) was active in the DFMO assay with a modest level of toxicity.

TABLE 4A

(4-1)

(4-2)

(4-3)

TABLE 4A-continued

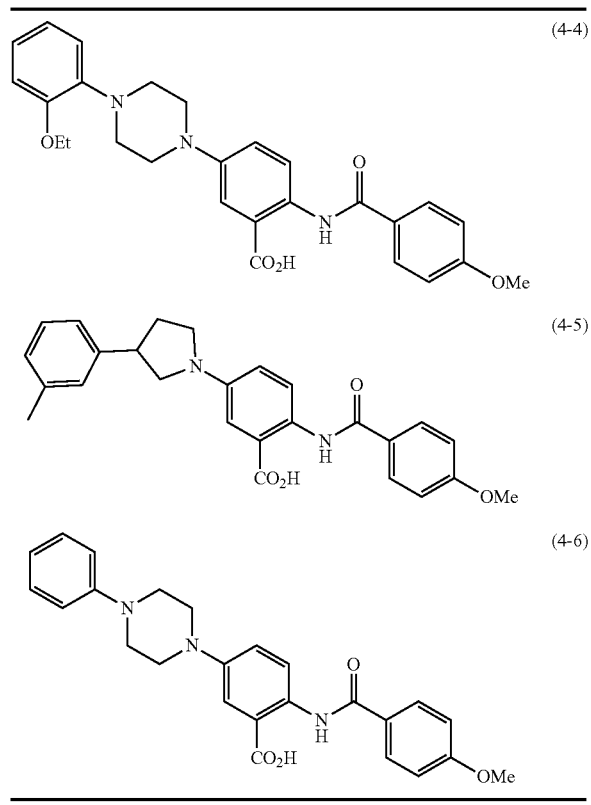

TABLE 4B

Featured samples in DFMO-spermidine rescue assay.

Figure 3:
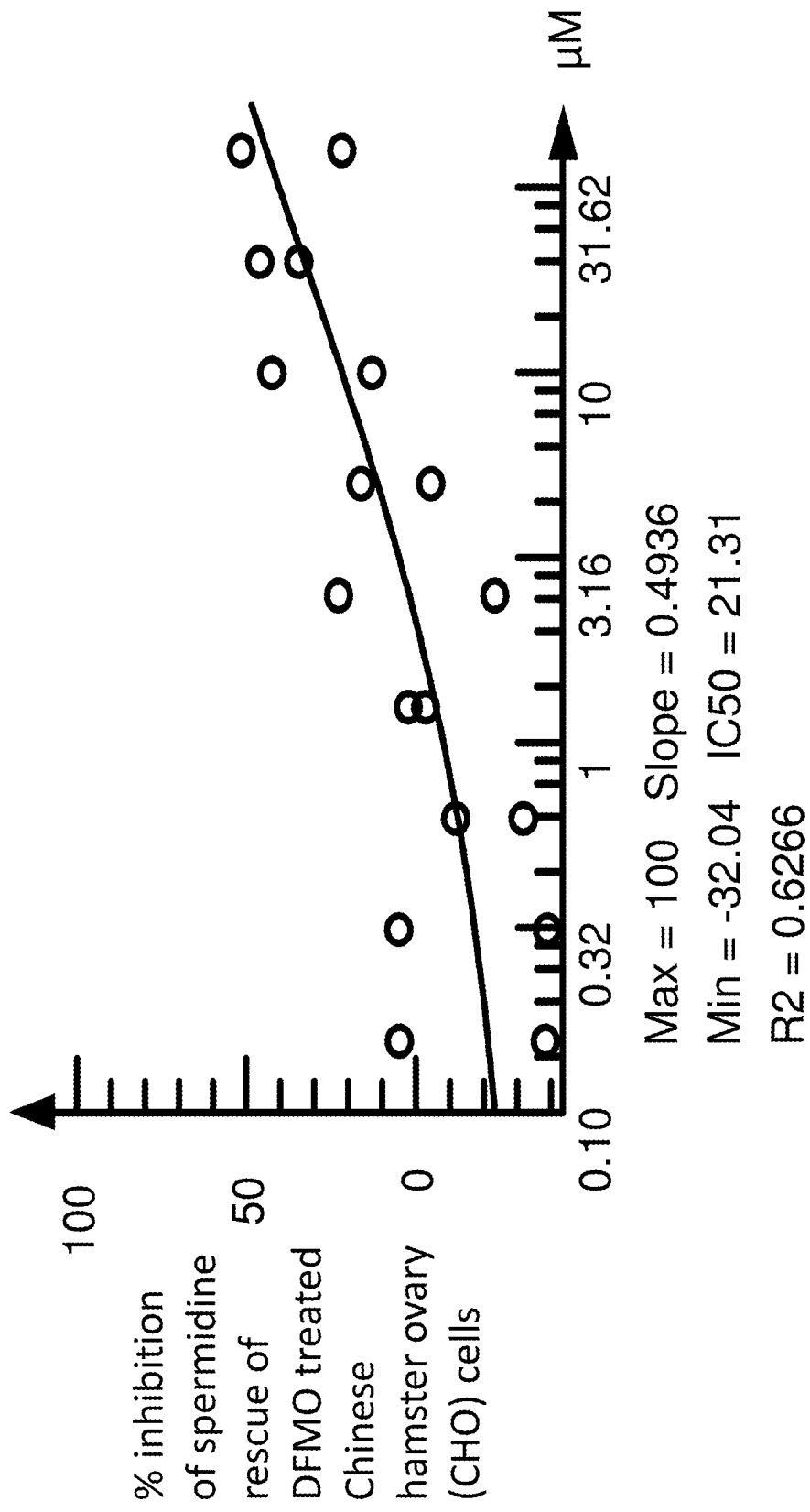
FIG. 3: is an example according to various embodiments illustrating a DFMO rescue experiment in CHO cells, in which the x-axis is concentration of the tested compound, which was the compound illustrated in structure (4-1) in Table 4A, in micromolar (μM) and the y-axis is % inhibition of spermidine rescue of DFMO treated Chinese hamster ovary (CHO) cells, where 100% represents the viability of the DFMO only control and the 0% represents the viability of DFMO+ spermidine treated cells. DFMO treated cells respond by increasing their polyamine import. A polyamine transport inhibitor will either inhibit the import or the intracellular trafficking of spermidine and alter spermidine's ability to rescue the DFMO-treated cells.
Figure 4:
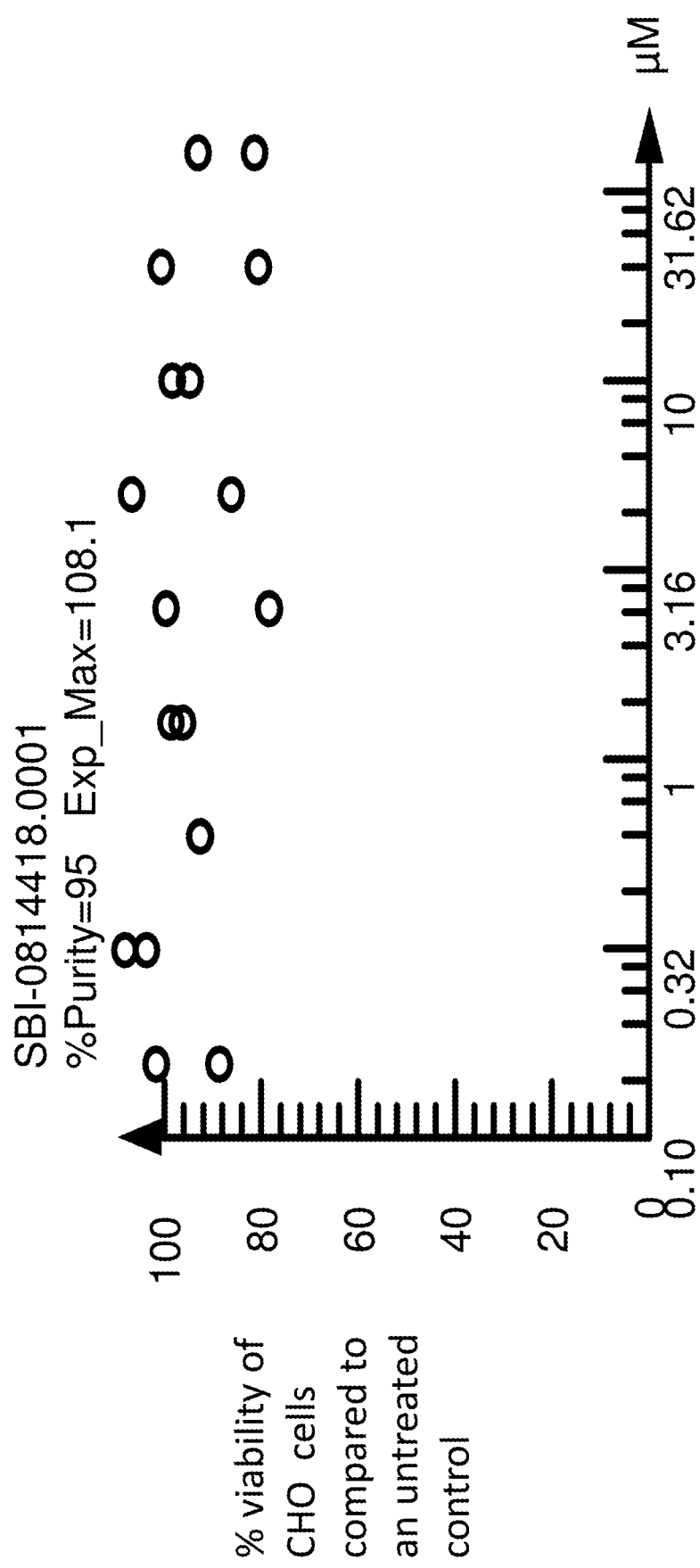
FIG. 4: is an example according to various embodiments illustrating a cytotoxicity screen in CHO cells, in which the x-axis is concentration of the tested compound, which was the compound illustrated in structure (4-1) in Table 4A, in micromolar (μM) and the y-axis is % viability of CHO cells compared to an untreated control.
Figure 5:
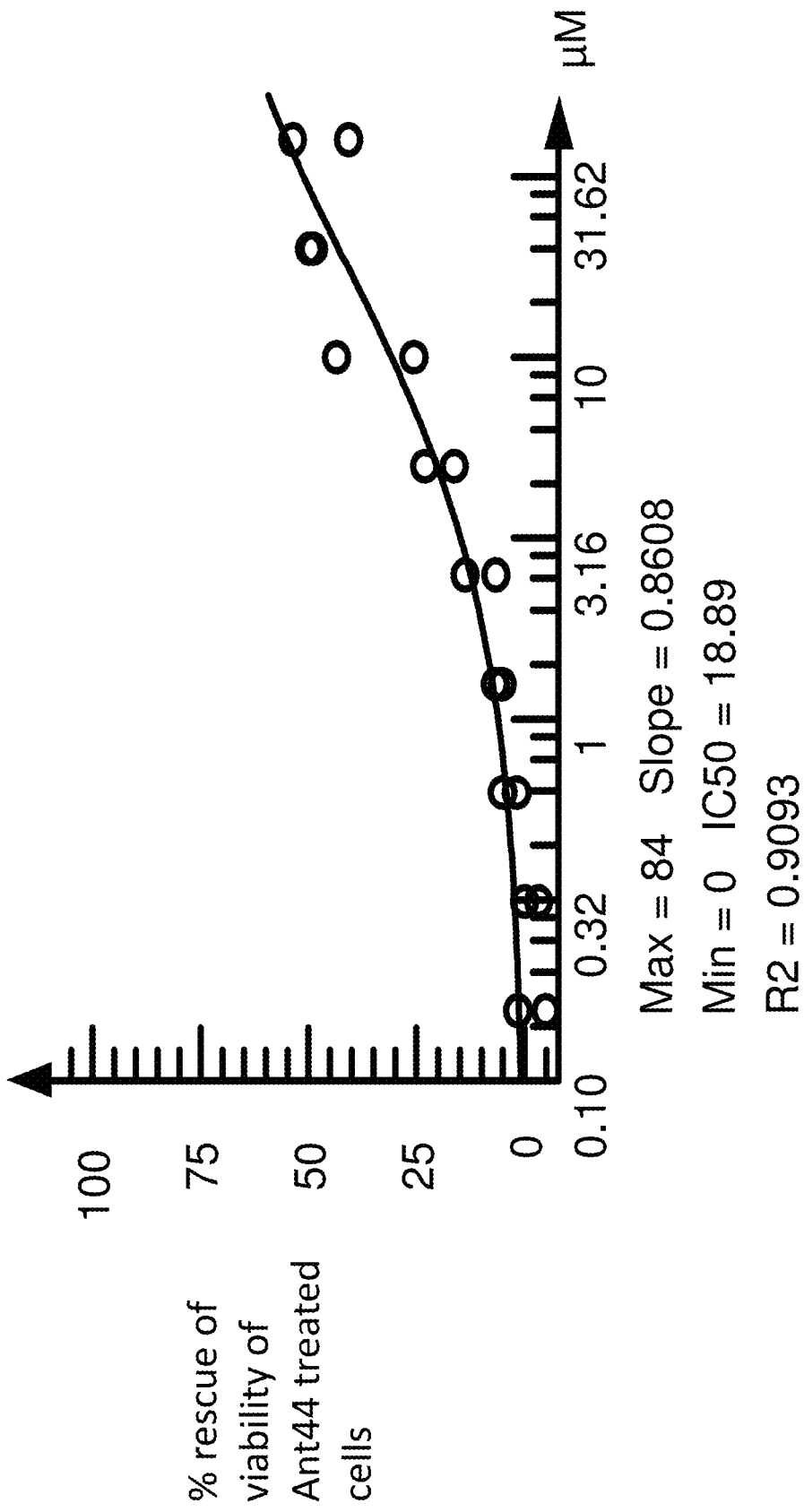
FIG. 5: is an example according to various embodiments illustrating an Ant44 rescue experiment in CHO cells, in which the x-axis is concentration of the tested compound, which was the compound illustrated in structure (4-1) in Table 4A, in micromolar (μM) and the y-axis is % rescue of viability of Ant44 treated cells, where 0% represents the viability of the Ant44 control and 100% represents the viability of untreated cells (i.e. complete rescue from Ant44 toxicity). Since Ant44 is a cytotoxic polyamine, a polyamine transport inhibitor will inhibit its import or intracellular transport and reduce its cytotoxicity.
Figure 6:
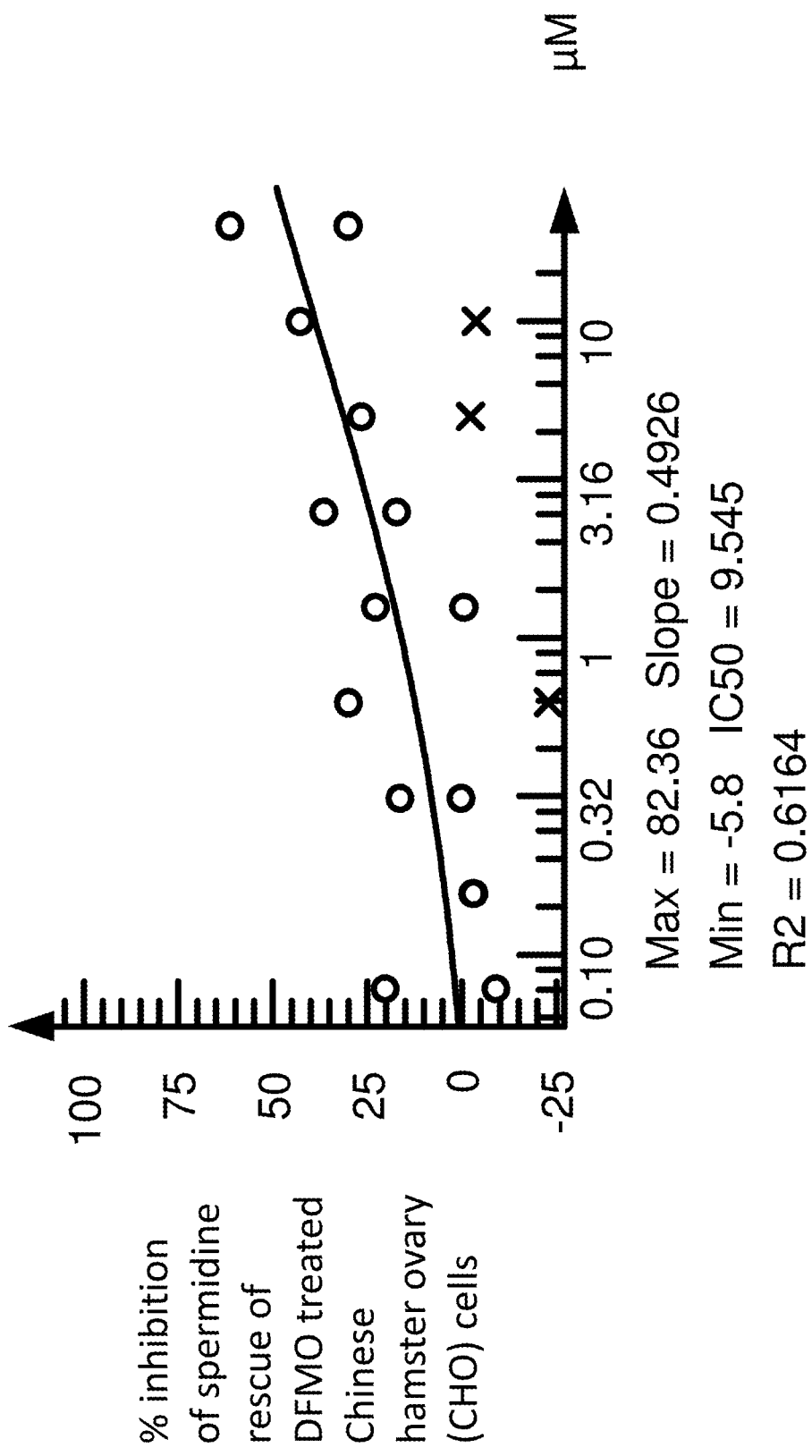
FIG. 6: is an example according to various embodiments illustrating a DFMO rescue experiment in CHO cells, in which the x-axis is concentration of the tested compound, which was the compound illustrated in structure (4-2) in Table 4A, in micromolar (μM) and the y-axis is % inhibition of spermidine rescue of DFMO treated Chinese hamster ovary (CHO) cells, where 100% represents the viability of the DFMO only control and the 0% represents the viability of DFMO+ spermidine treated cells.
Figure 7:
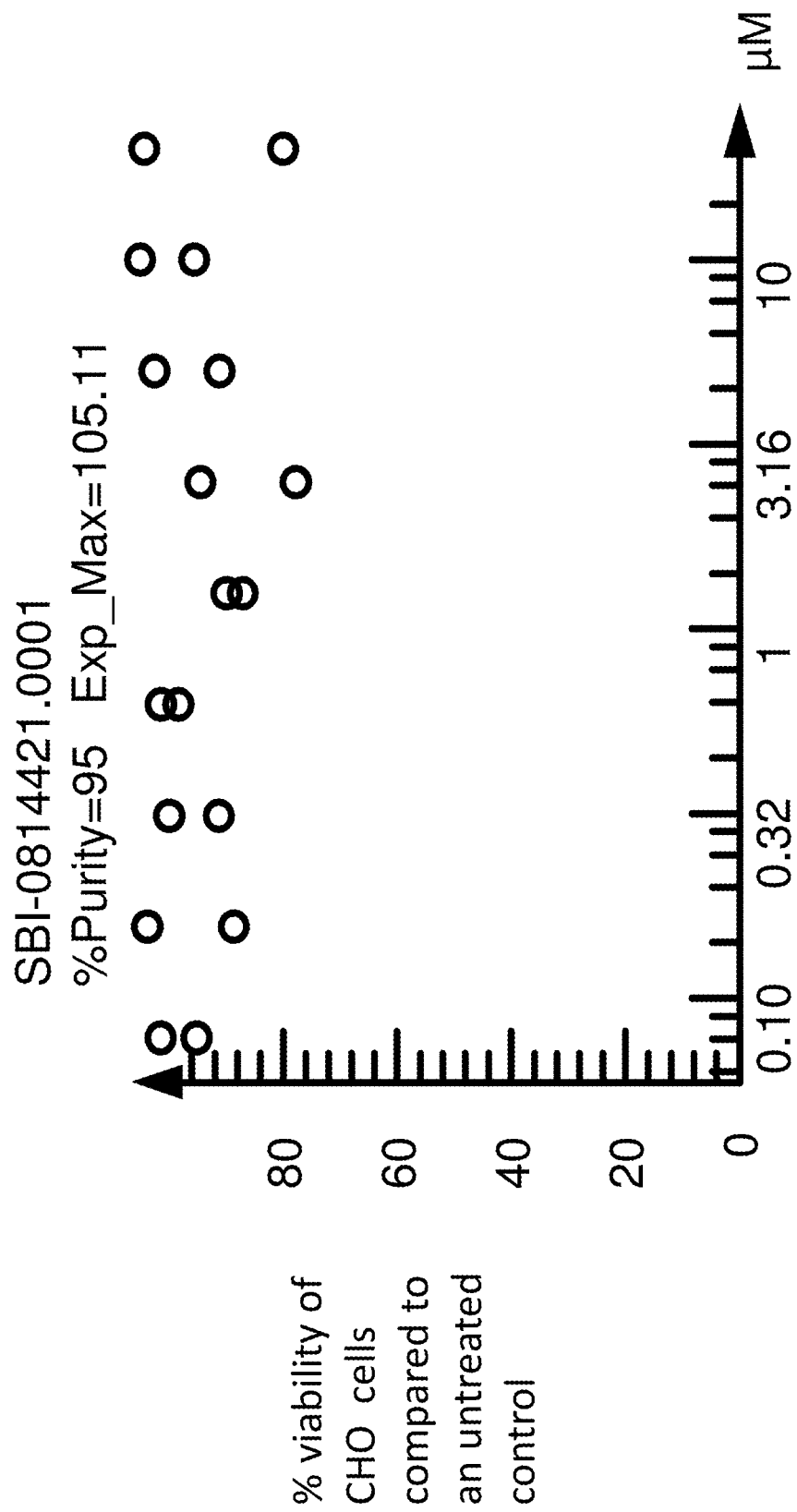
FIG. 7: is an example according to various embodiments illustrating a cytotoxicity screen in CHO cells, in which the x-axis is concentration of the tested compound, which was the compound illustrated in structure (4-2) in Table 4A, in micromolar (μM) and the y-axis is % viability of CHO cells compared to an untreated control.
Figure 8:
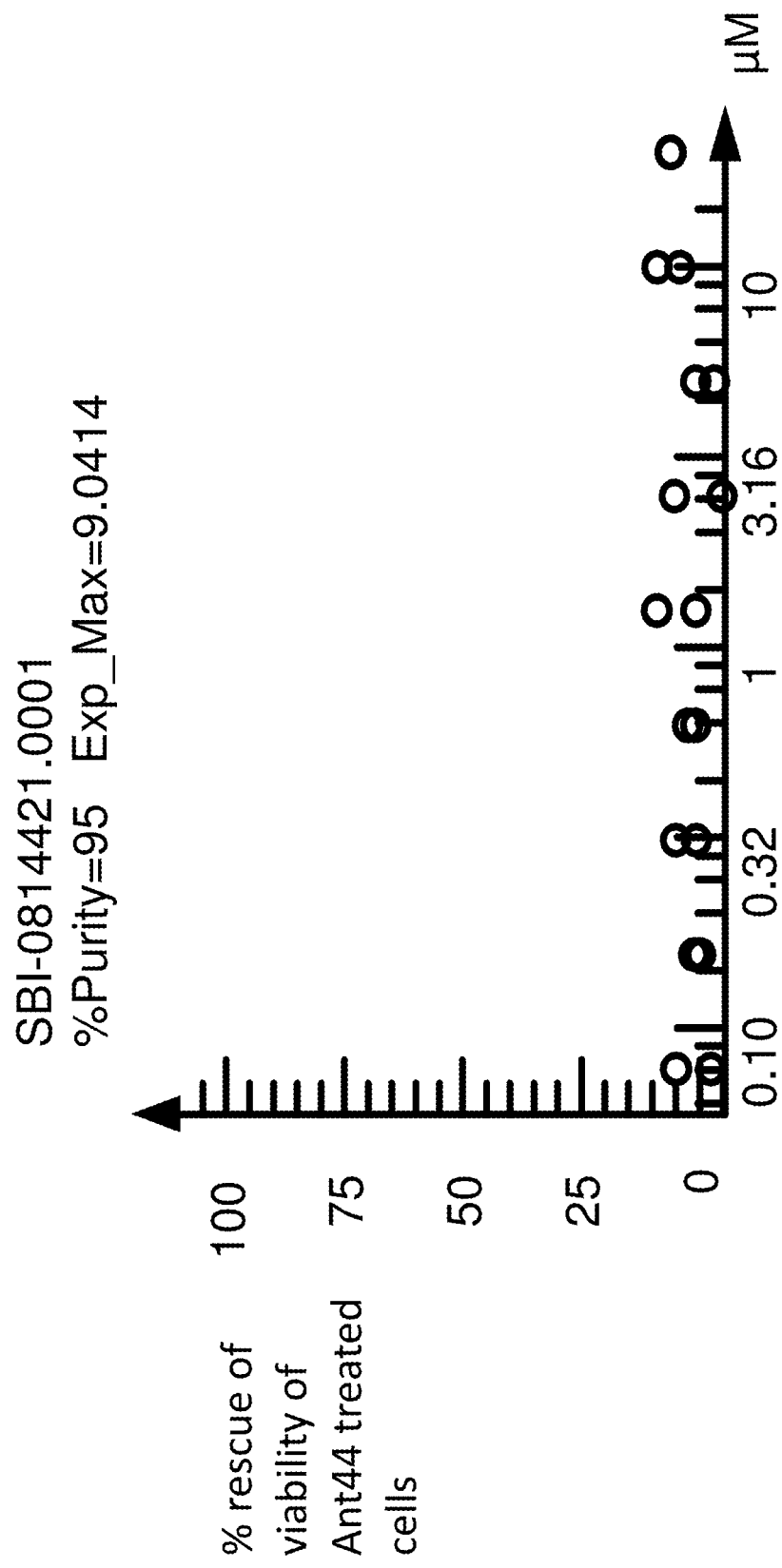
FIG. 8: is an example according to various embodiments illustrating an Ant44 rescue experiment in CHO cells, in which the x-axis is concentration of the tested compound, which was the compound illustrated in structure (4-2) in Table 4A, in micromolar (μM) and the y-axis is % rescue of viability of Ant44 treated cells, where 0% represents the viability of the Ant44 control and 100% represents the viability of untreated cells (i.e. complete rescue from Ant44 toxicity)
Figure 9:
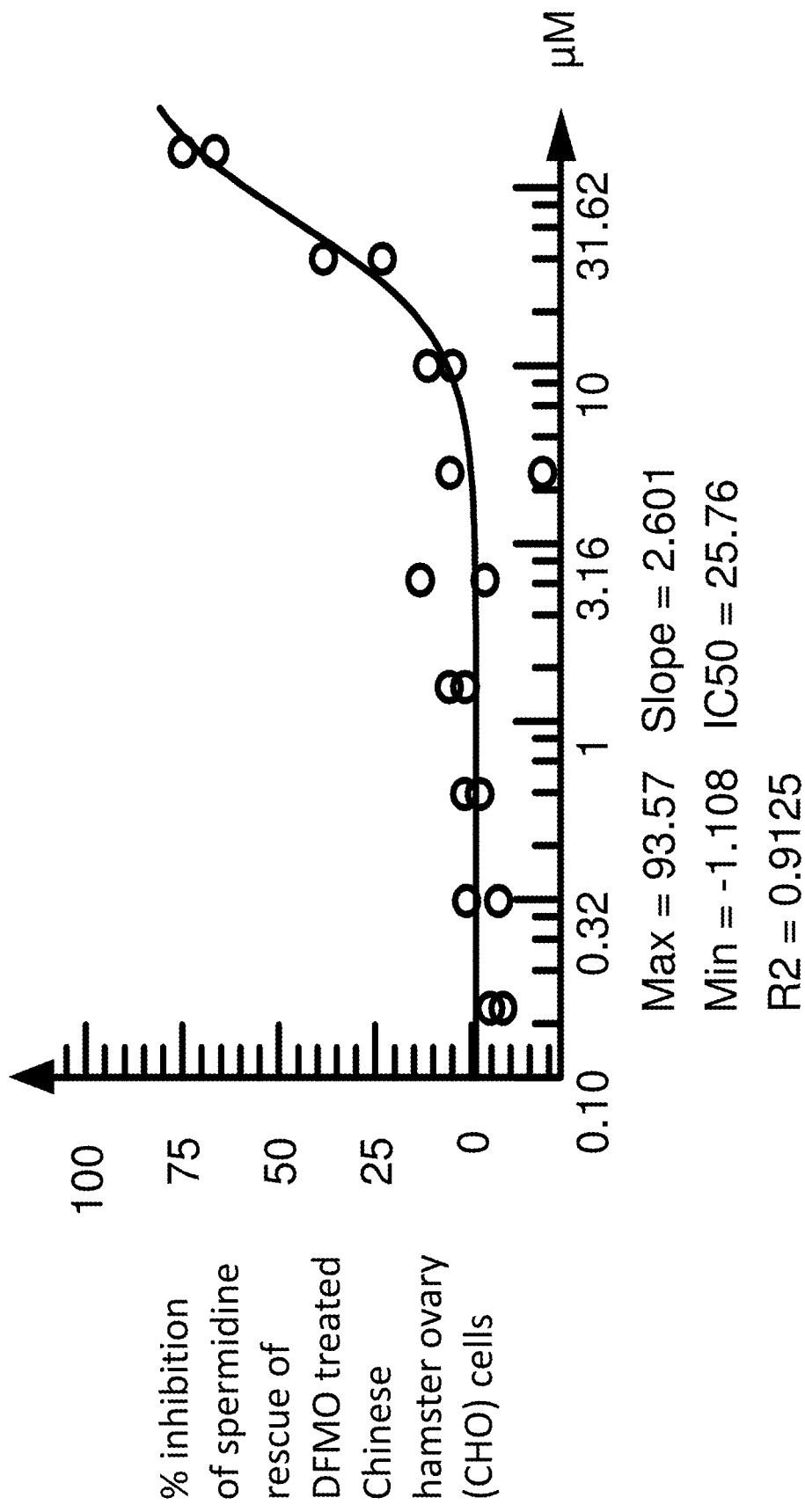
FIG. 9: is an example according to various embodiments illustrating a DFMO rescue experiment in CHO cells, in which the x-axis is concentration of the tested compound, which was the compound illustrated in structure (4-3) in Table 4A, in micromolar (μM) and the y-axis is % inhibition of spermidine rescue of DFMO treated Chinese hamster ovary (CHO) cells, where 100% represents the viability of the DFMO only control and the 0% represents the viability of DFMO+ spermidine treated cells.
Figure 10:
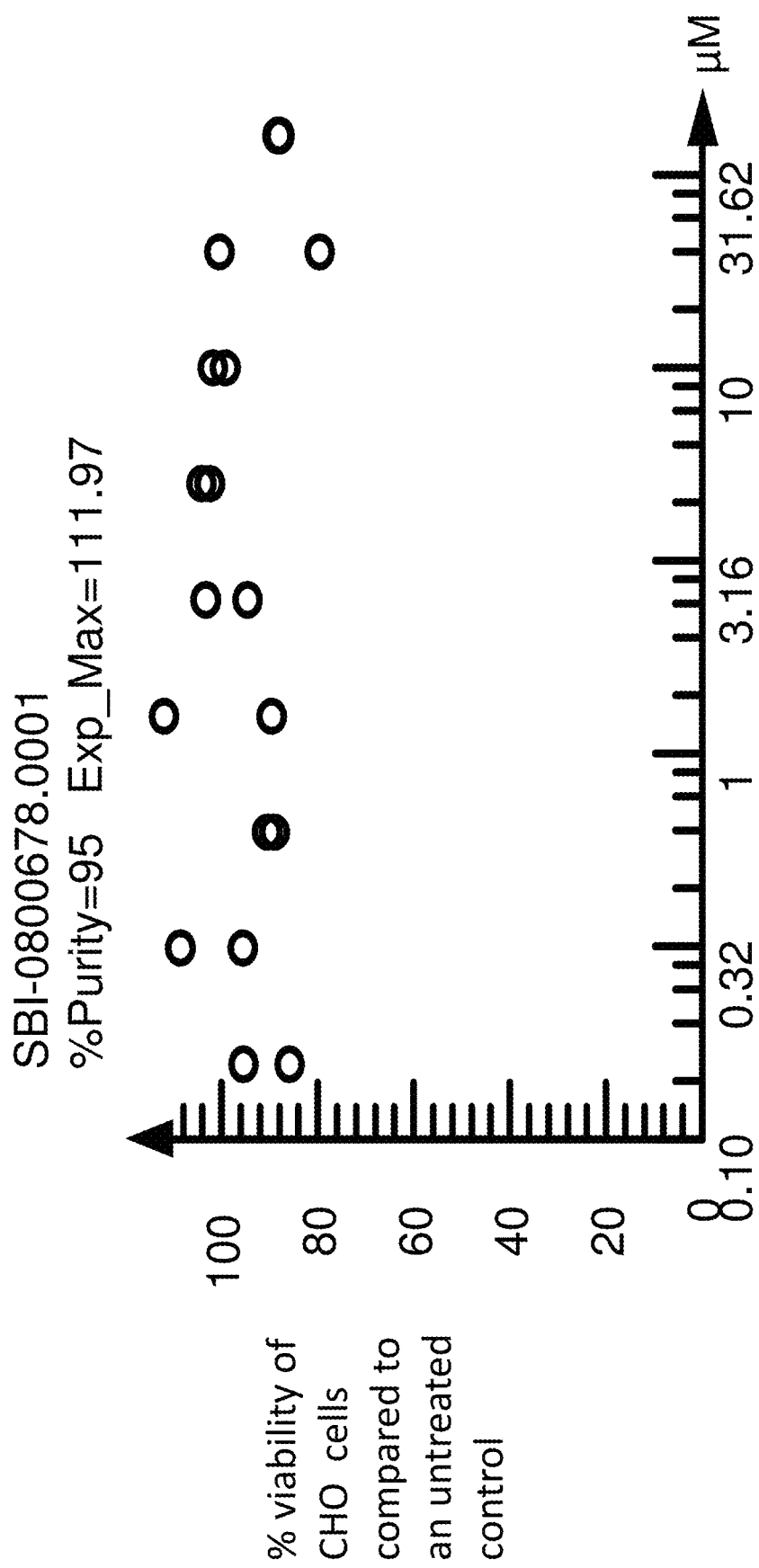
FIG. 10: is an example according to various embodiments illustrating a cytotoxicity screen in CHO cells, in which the x-axis is concentration of the tested compound, which was the compound illustrated in structure (4-3) in Table 4A, in micromolar (μM) and the y-axis is % viability of CHO cells compared to an untreated control.
Figure 11:
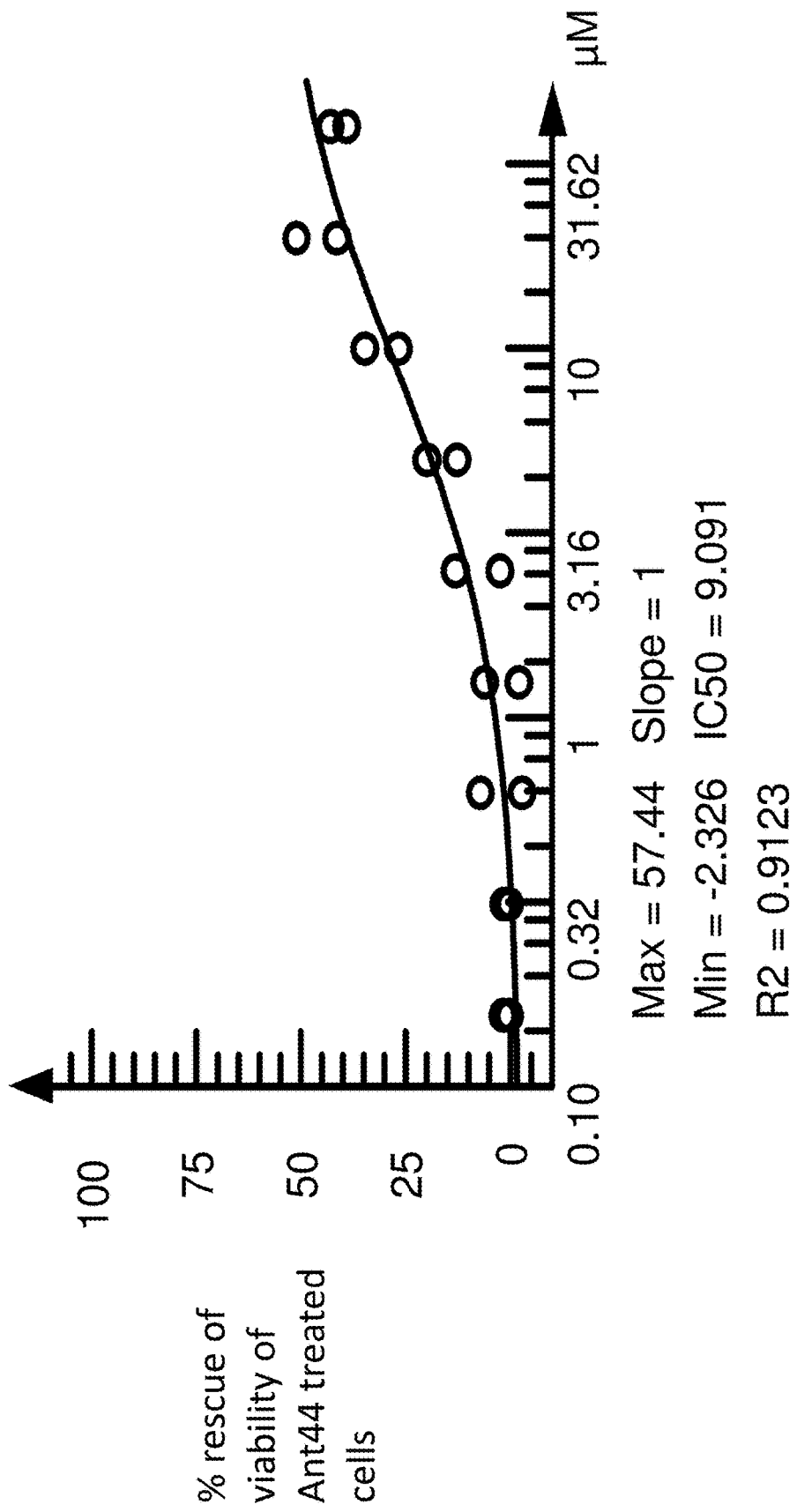
FIG. 11: is an example according to various embodiments illustrating an Ant44 rescue experiment in CHO cells, in which the x-axis is concentration of the tested compound, which was the compound illustrated in structure (4-3) in Table 4A, in micromolar (μM) and the y-axis is % rescue of viability of Ant44 treated cells, where 0% represents the viability of the Ant44 control and 100% represents the viability of untreated cells (i.e. complete rescue from Ant44 toxicity)
Figure 12:
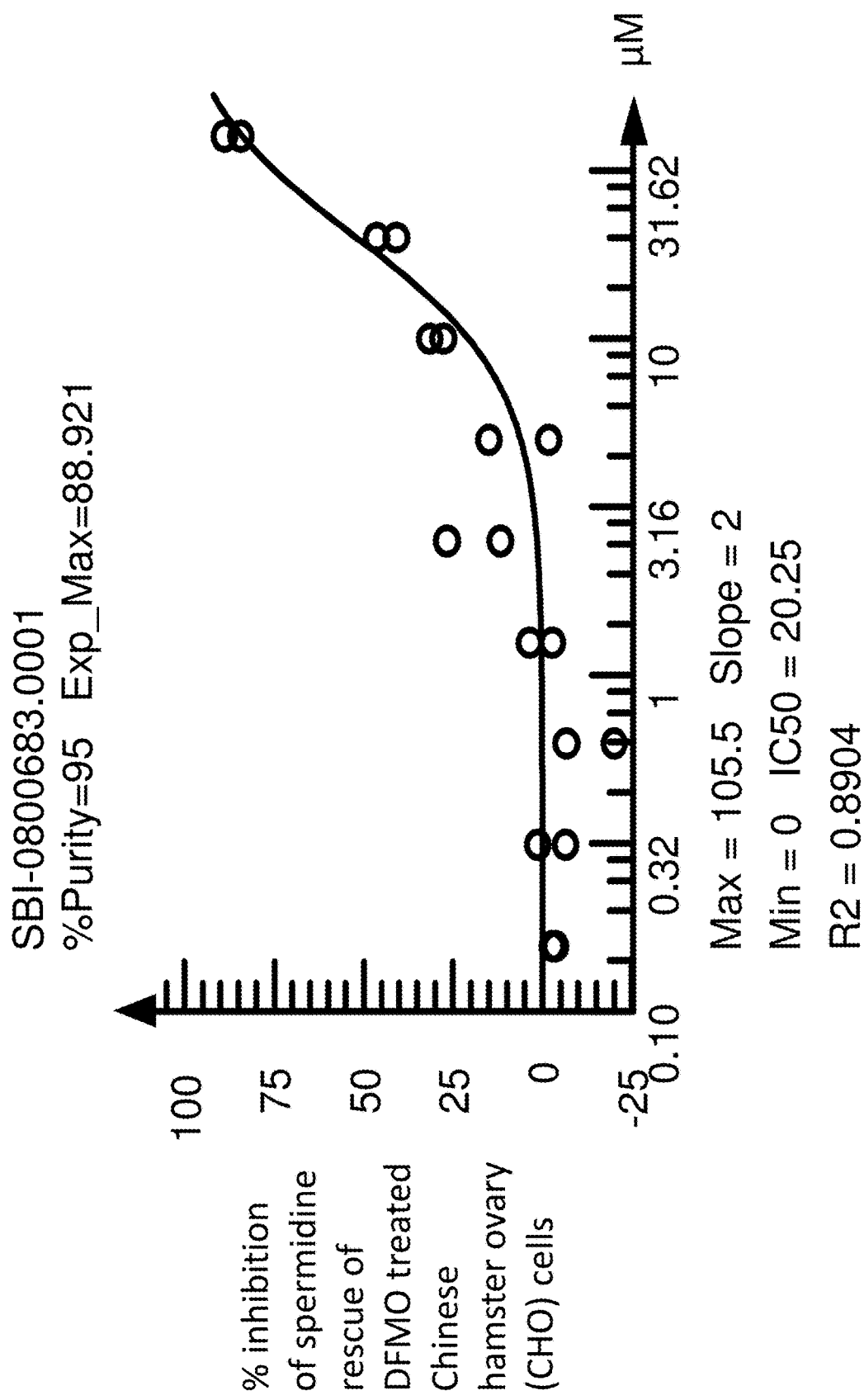
FIG. 12: is an example according to various embodiments illustrating a DFMO rescue experiment in CHO cells, in which the x-axis is concentration of the tested compound, which was the compound illustrated in structure (4-4) in Table 4A, in micromolar (μM) and the y-axis is % inhibition of spermidine rescue of DFMO treated Chinese hamster ovary (CHO) cells, where 100% represents the viability of the DFMO only control and the 0% represents the viability of DFMO+ spermidine treated cells.
Figure 13:
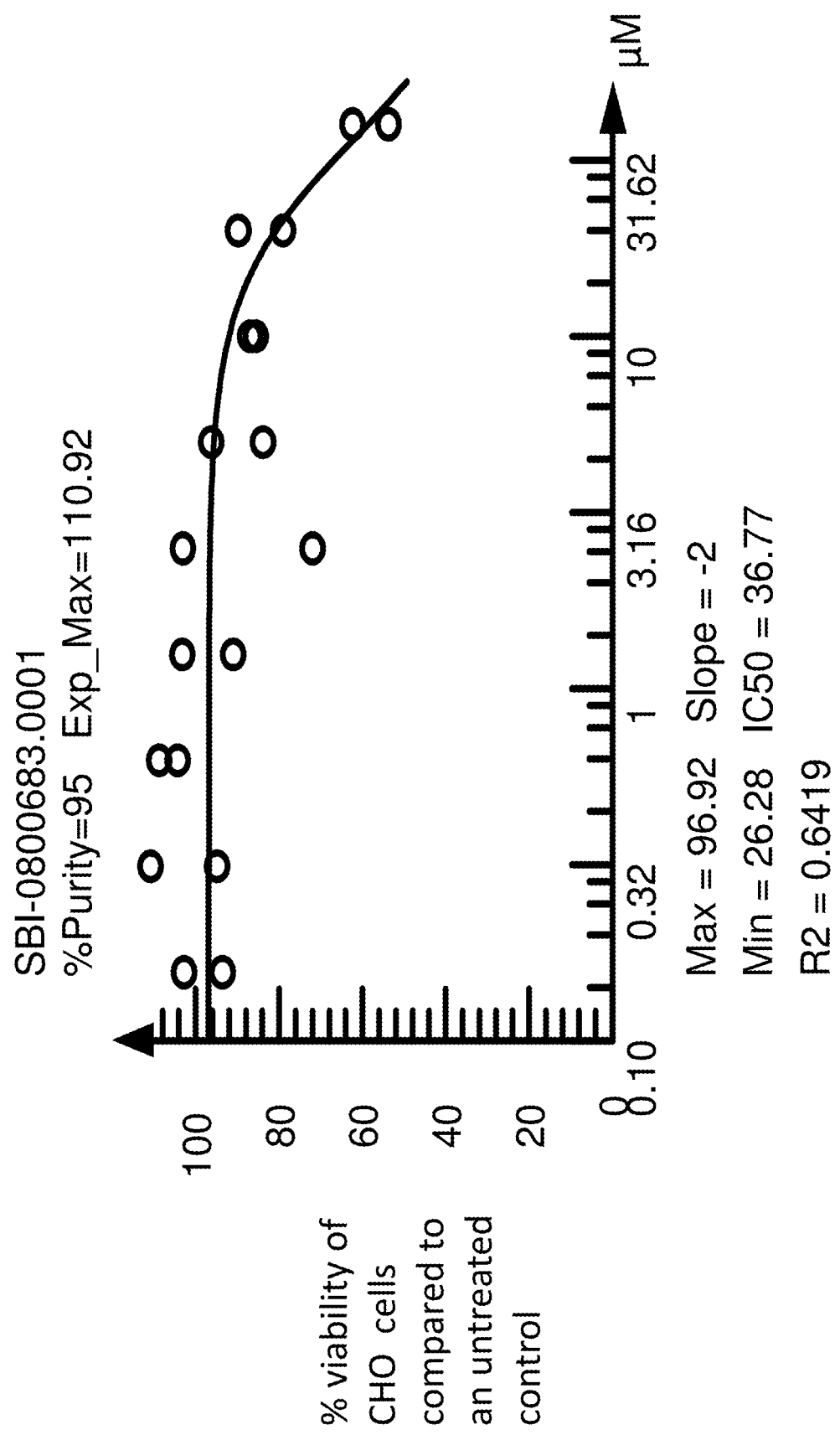
FIG. 13: is an example according to various embodiments illustrating a cytotoxicity screen in CHO cells, in which the x-axis is concentration of the tested compound, which was the compound illustrated in structure (4-4) in Table 4A, in micromolar (μM) and the y-axis is % viability of CHO cells compared to an untreated control.
Figure 14:
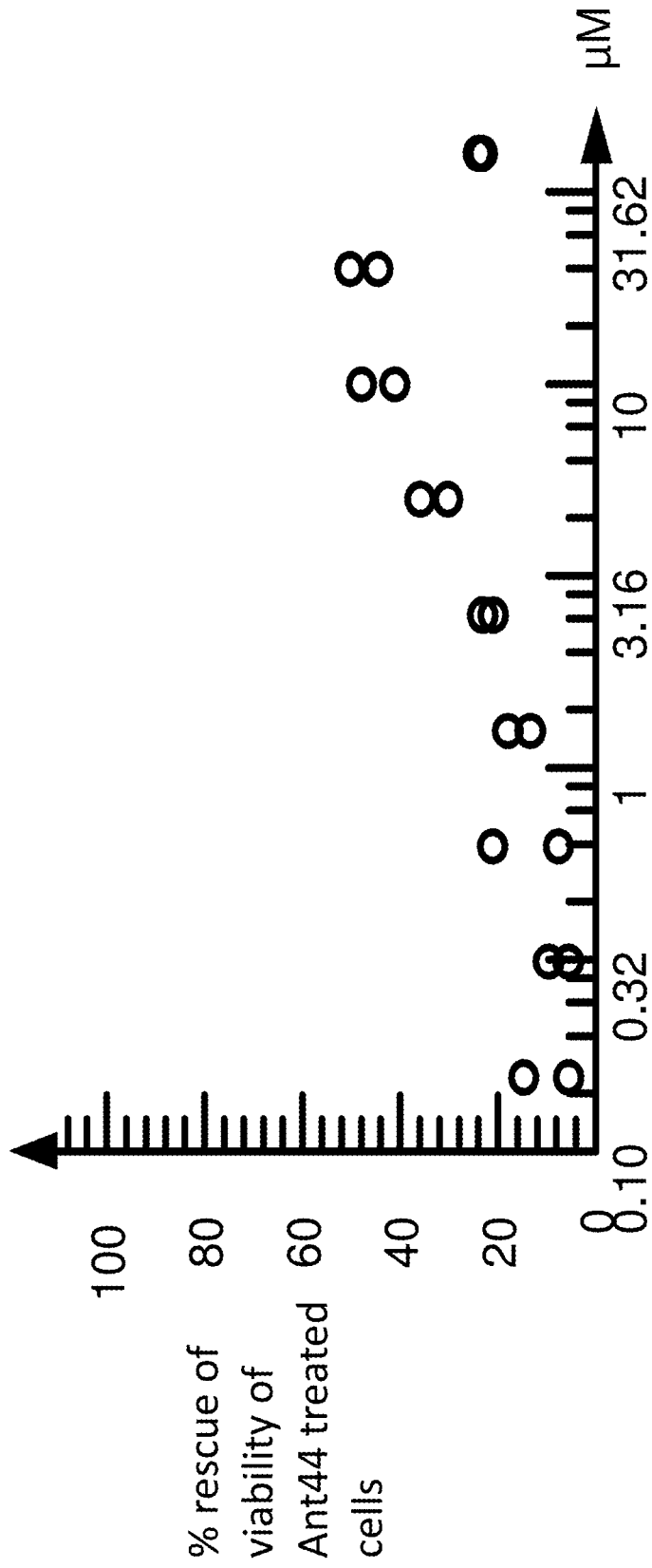
FIG. 14: is an example according to various embodiments illustrating an Ant44 rescue experiment in CHO cells, in which the x-axis is concentration of the tested compound, which was the compound illustrated in structure (4-4) in Table 4A, in micromolar (μM) and the y-axis is % rescue of viability of Ant44 treated cells, where 0% represents the viability of the Ant44 control and 100% represents the viability of untreated cells (i.e. complete rescue from Ant44 toxicity)
Figure 15:
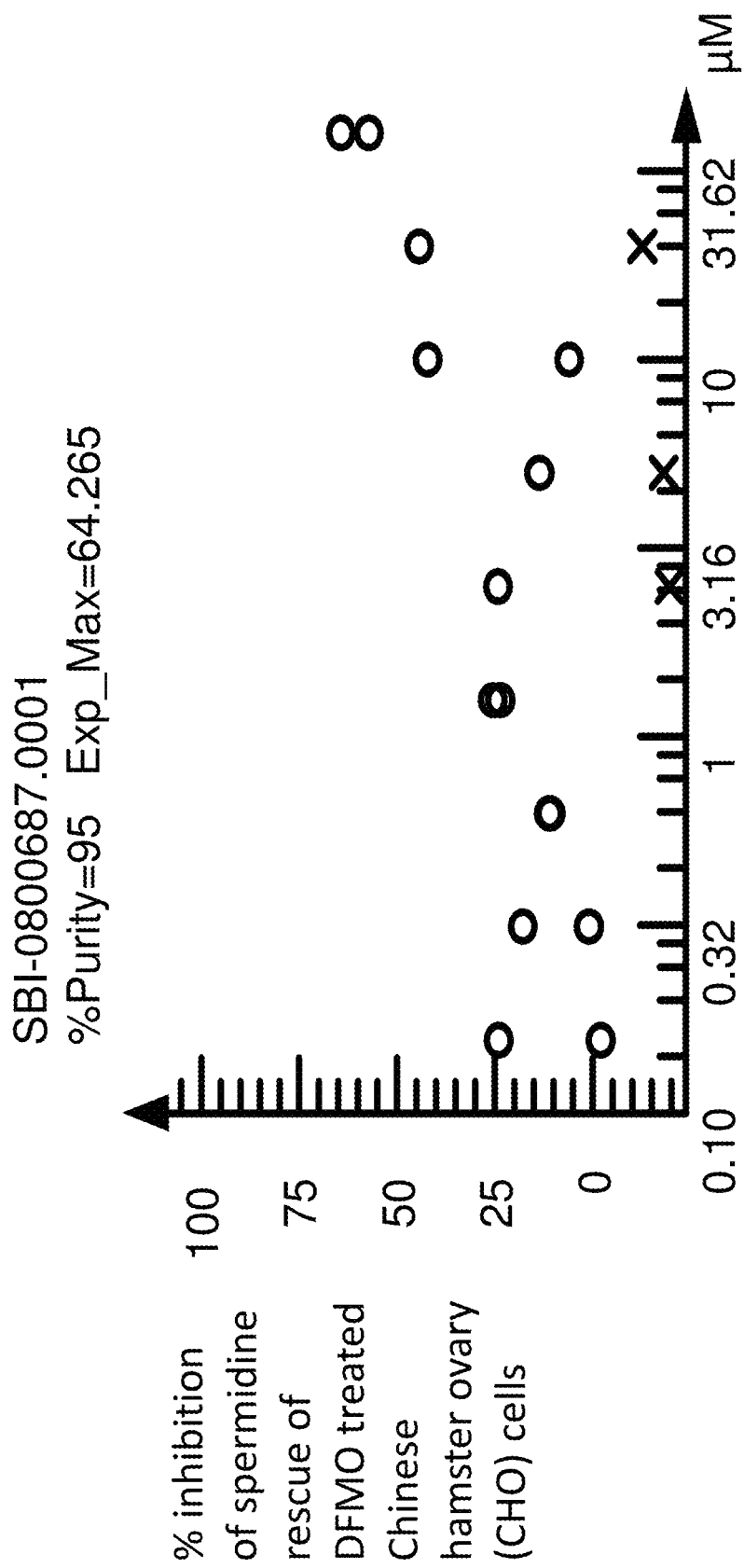
FIG. 15: is an example according to various embodiments illustrating a DFMO rescue experiment in CHO cells, in which the x-axis is concentration of the tested compound, which was the compound illustrated in structure (4-5) in Table 4A, in micromolar (μM) and the y-axis is % inhibition of spermidine rescue of DFMO treated Chinese hamster ovary (CHO) cells, where 100% represents the viability of the DFMO only control and the 0% represents the viability of DFMO+ spermidine treated cells.
Figure 16:
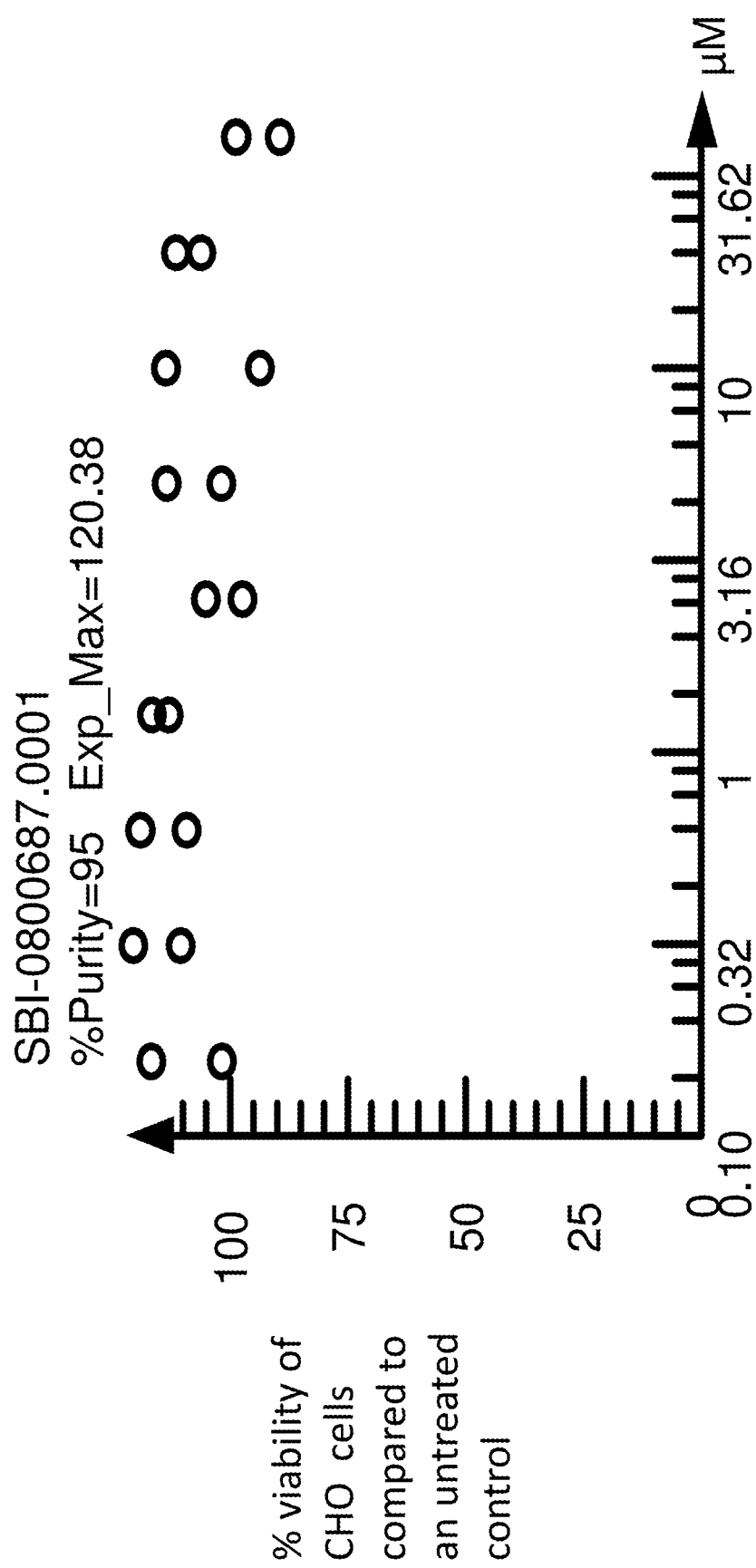
FIG. 16: is an example according to various embodiments illustrating a cytotoxicity screen in CHO cells, in which the x-axis is concentration of the tested compound, which was the compound illustrated in structure (4-5) in Table 4A, in micromolar (μM) and the y-axis is % viability of CHO cells compared to an untreated control.
Figure 17:
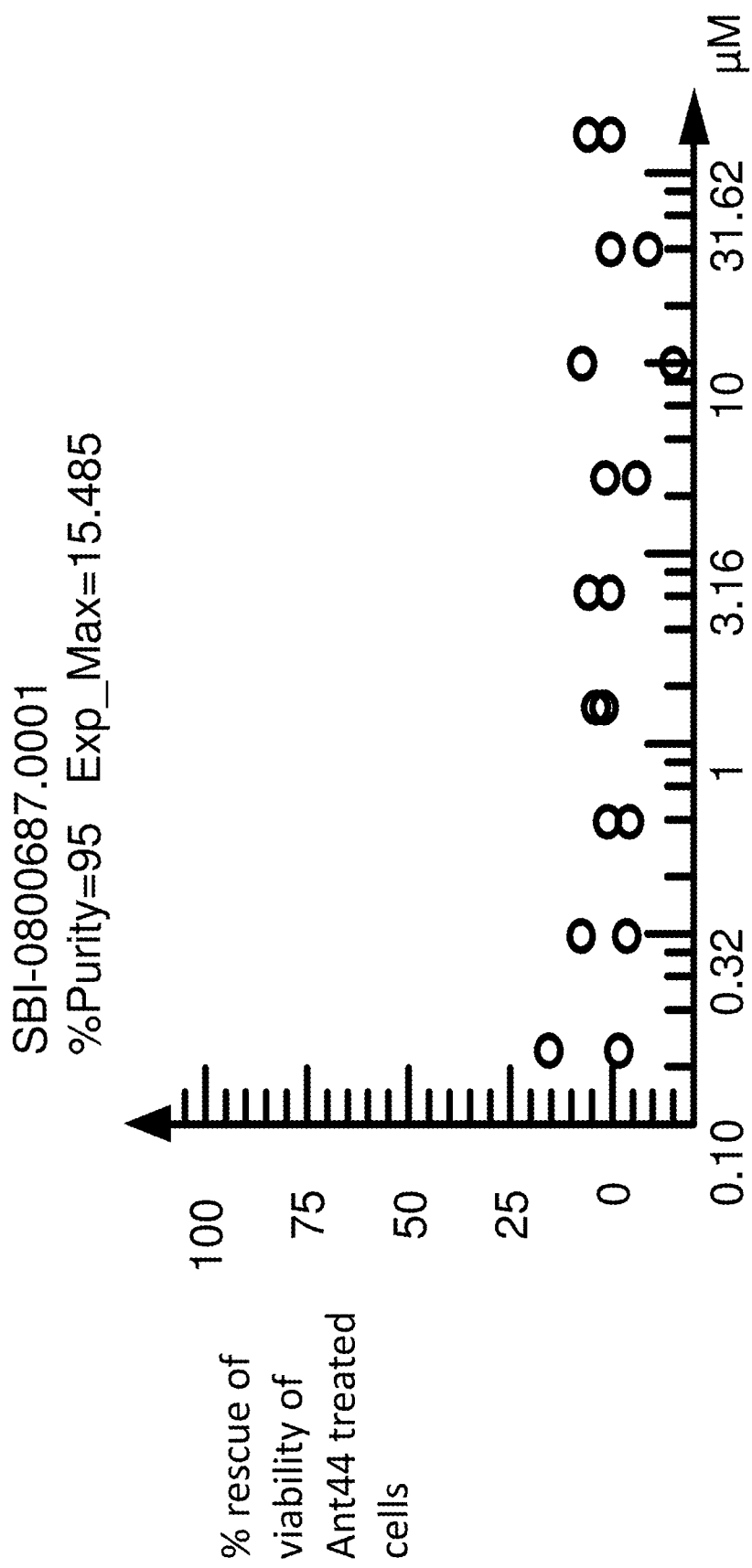
FIG. 17: is an example according to various embodiments illustrating an Ant44 rescue experiment in CHO cells, in which the x-axis is concentration of the tested compound, which was the compound illustrated in structure (4-5) in Table 4A, in micromolar (μM) and the y-axis is % rescue of viability of Ant44 treated cells, where 0% represents the viability of the Ant44 control and 100% represents the viability of untreated cells (i.e. complete rescue from Ant44 toxicity)
Figure 18:
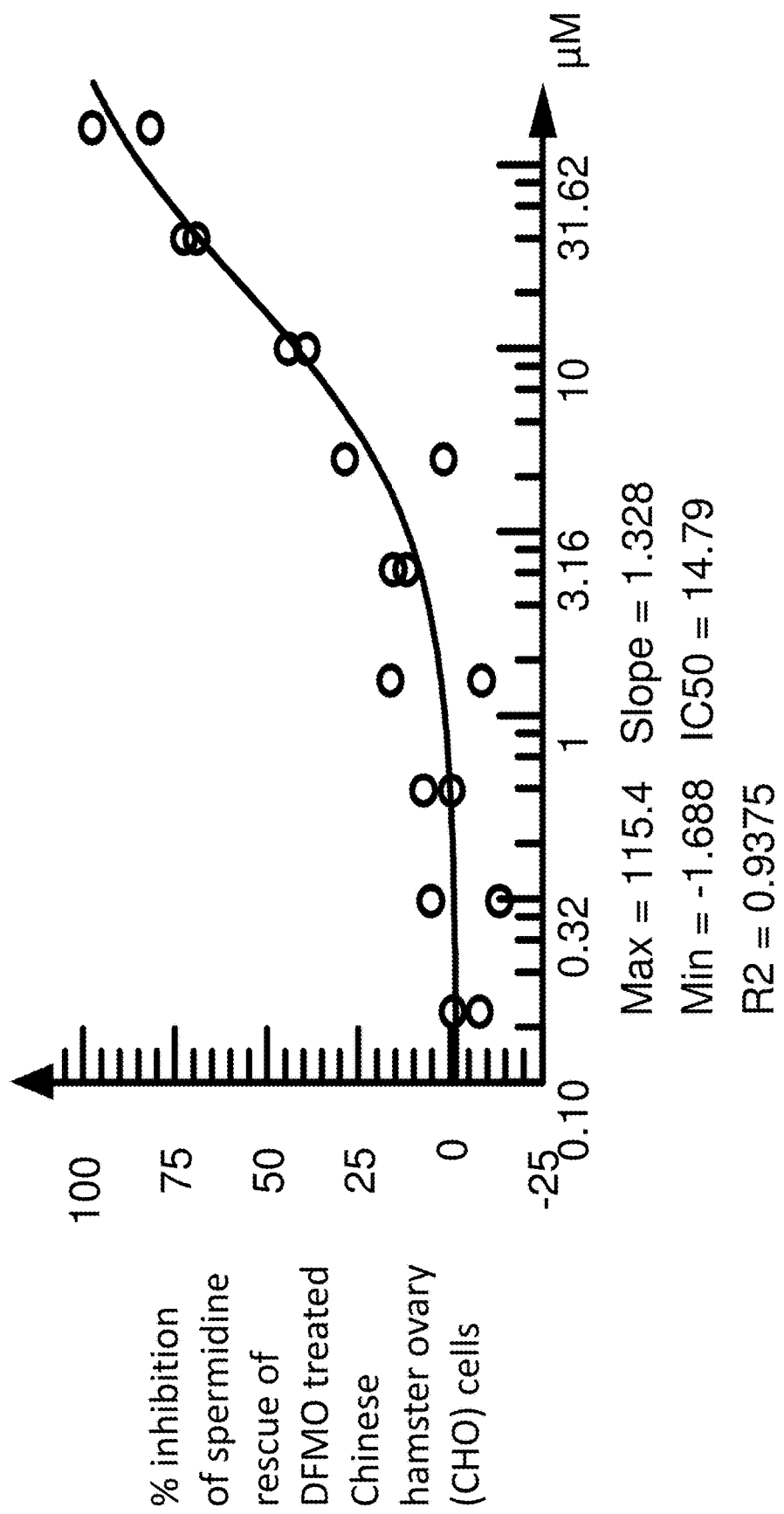
FIG. 18: is an example according to various embodiments illustrating a DFMO rescue experiment in CHO cells, in which the x-axis is concentration of the tested compound, which was the compound illustrated in structure (4-6) in Table 4A, in micromolar (μM) and the y-axis is % inhibition of spermidine rescue of DFMO treated Chinese hamster ovary (CHO) cells, where 100% represents the viability of the DFMO only control and the 0% represents the viability of DFMO+ spermidine treated cells.
Figure 19:
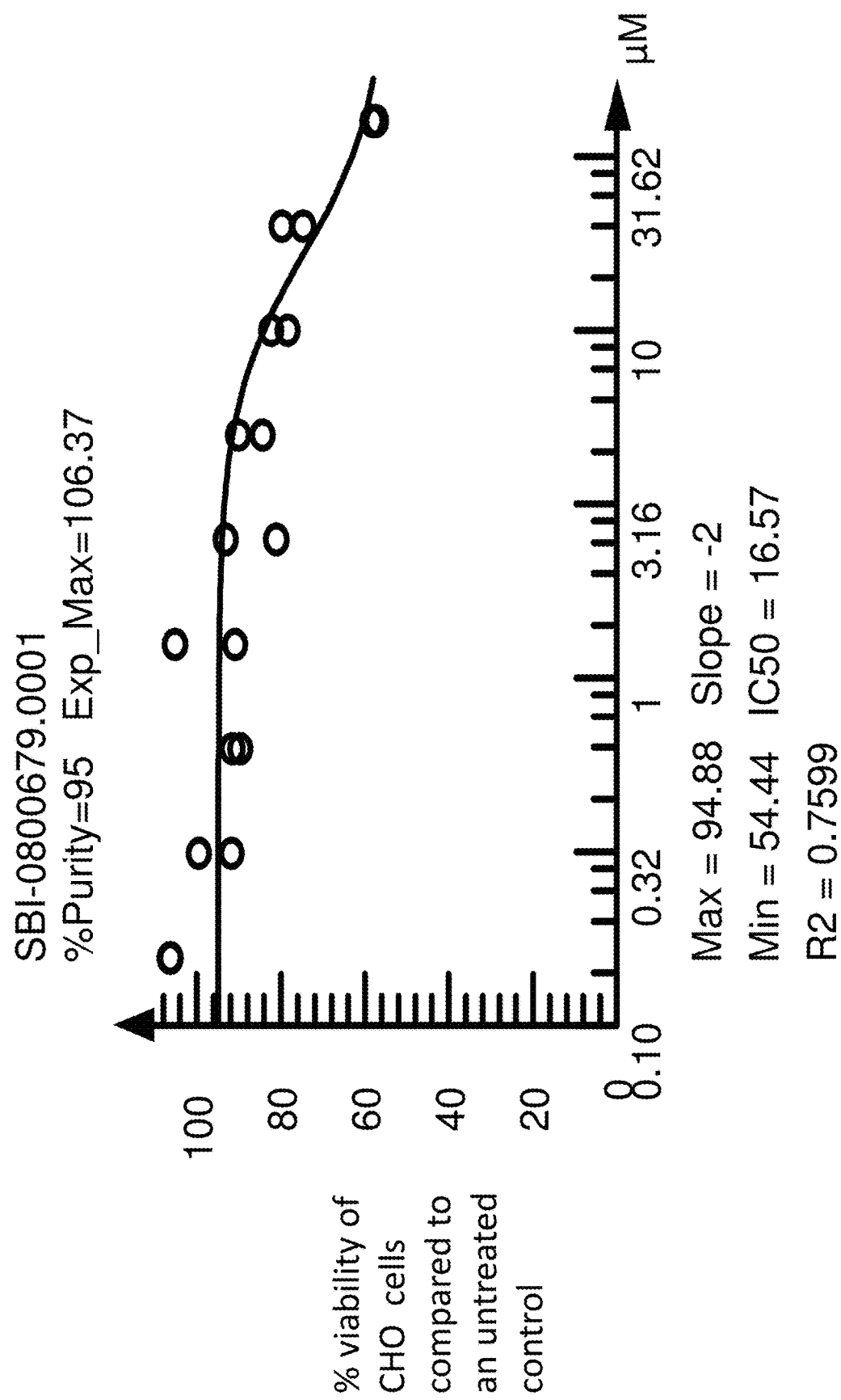
FIG. 19: is an example according to various embodiments illustrating a cytotoxicity screen in CHO cells, in which the x-axis is concentration of the tested compound, which was the compound illustrated in structure (4-6) in Table 4A, in micromolar (μM) and the y-axis is % viability of CHO cells compared to an untreated control.
Figure 20:
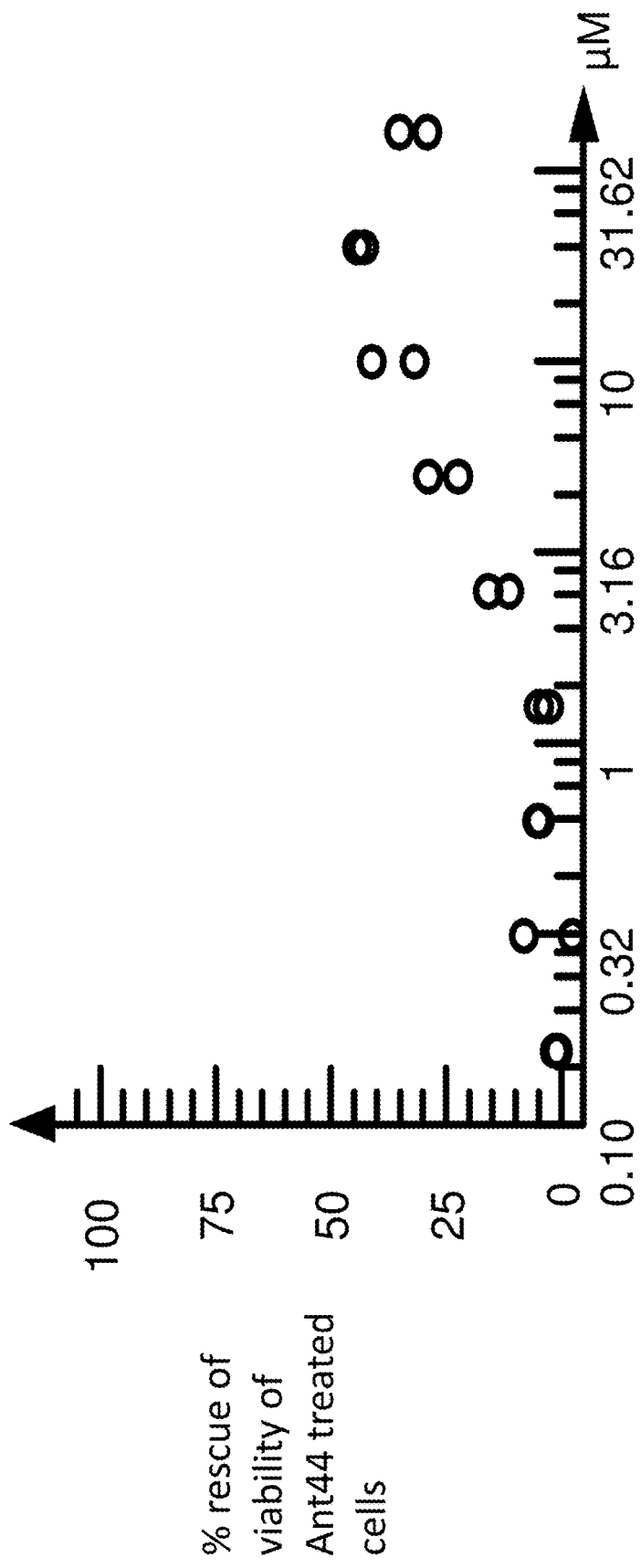
FIG. 20: is an example according to various embodiments illustrating an Ant44 rescue experiment in CHO cells, in which the x-axis is concentration of the tested compound, which was the compound illustrated in structure (4-6) in Table 4A, in micromolar (µM) and the y-axis is % rescue of viability of Ant44 treated cells, where 0% represents the viability of the Ant44 control and 100% represents the viability of untreated cells (i.e. complete rescue from Ant44 toxicity)

| Structure | SBI | DFMO/CHO IC$_{50}$ (µM) | CHO MTD EC$_{50}$ (µM) | Ant44 IC$_{50}$ (µM) | L3.6pl EC$_{50}$ (µM) | L3.6pl MTD (µM) |
|---|---|---|---|---|---|---|
| (4-1) | 0814418 | (21) See: FIG. 3 | N/A See: FIG. 4 | (19) See: FIG. 5 | (5) | (5-10) |
| (4-2) | 0814421 | (9.5) See: FIG. 6 | N/A See: FIG. 7 | N/A See: FIG. 8 | (>10) | (10) |
| (4-3) | 0800678 | (26) See: FIG. 9 | N/A See: FIG. 10 | (9.0) See: FIG. 11 | | |
| (4-4) | 0800683 | (20) See: FIG. 12 | (37) See: FIG. 13 | trace See: FIG. 14 | | |
| (4-5) | 0800687 | trace See: FIG. 15 | N/A See: FIG. 16 | N/A See: FIG. 17 | | |
| (4-6) | 0800679 | (15) See: FIG. 18 | (17) See: FIG. 19 | trace See: FIG. 20 | | |

Table 4B includes references to FIGS. 3-20.

FIG. 3 is an example according to various embodiments illustrating a DFMO rescue experiment in CHO cells, in which the x-axis is concentration of the tested compound, which was the compound illustrated in structure (4-1) in Table 4A, in micromolar (µM) and the y-axis is % inhibition of spermidine rescue of DFMO treated Chinese hamster ovary (CHO) cells, where 100% represents the viability of the DFMO only control and the 0% represents the viability of DFMO+ spermidine treated cells.

FIG. 4 is an example according to various embodiments illustrating a cytotoxicity screen in CHO cells, in which the x-axis is concentration of the tested compound, which was the compound illustrated in in structure (4-1) in Table 4A, in micromolar (µM) and the y-axis is % viability of CHO cells compared to an untreated control.

FIG. 5 is an example according to various embodiments illustrating an Ant44 rescue experiment in CHO cells, in which the x-axis is concentration of the tested compound, which was the compound illustrated in in structure (4-1) in Table 4A, in micromolar (µM) and the y-axis is % rescue of viability of Ant44 treated cells, where 0% represents the viability of the Ant44 control and 100% represents the viability of untreated cells (i.e. complete rescue from Ant44 toxicity).

FIG. 6 is an example according to various embodiments illustrating a DFMO rescue experiment in CHO cells, in which the x-axis is concentration of the tested compound, which was the compound illustrated in in structure (4-2) in Table 4A, in micromolar (µM) and the y-axis is % inhibition of spermidine rescue of DFMO treated Chinese hamster ovary (CHO) cells, where 100% represents the viability of the DFMO only control and the 0% represents the viability of DFMO+ spermidine treated cells.

FIG. 7 is an example according to various embodiments illustrating a cytotoxicity screen in CHO cells, in which the x-axis is concentration of the tested compound, which was the compound illustrated in structure (4-2) in Table 4A, in micromolar (µM) and the y-axis is % viability of CHO cells compared to an untreated control.

FIG. 8 is an example according to various embodiments illustrating an Ant44 rescue experiment in CHO cells, in which the x-axis is concentration of the tested compound, which was the compound illustrated in structure (4-2) in Table 4A, in micromolar (µM) and the y-axis is % rescue of viability of Ant44 treated cells, where 0% represents the viability of the Ant44 control and 100% represents the viability of untreated cells (i.e. complete rescue from Ant44 toxicity).

FIG. 9 is an example according to various embodiments illustrating a DFMO rescue experiment in CHO cells, in which the x-axis is concentration of the tested compound, which was the compound illustrated in structure (4-3) in Table 4A, in micromolar (µM) and the y-axis is % inhibition of spermidine rescue of DFMO treated Chinese hamster ovary (CHO) cells, where 100% represents the viability of the DFMO only control and the 0% represents the viability of DFMO+ spermidine treated cells.

FIG. 10 is an example according to various embodiments illustrating a cytotoxicity screen in CHO cells, in which the x-axis is concentration of the tested compound, which was the compound illustrated in structure (4-3) in Table 4A, in micromolar (µM) and the y-axis is % viability of CHO cells compared to an untreated control.

FIG. 11 is an example according to various embodiments illustrating an Ant44 rescue experiment in CHO cells, in which the x-axis is concentration of the tested compound, which was the compound illustrated in structure (4-3) in Table 4A, in micromolar (µM) and the y-axis is % rescue of viability of Ant44 treated cells, where 0% represents the viability of the Ant44 control and 100% represents the viability of untreated cells (i.e. complete rescue from Ant44 toxicity).

FIG. 12 is an example according to various embodiments illustrating a DFMO rescue experiment in CHO cells, in which the x-axis is concentration of the tested compound, which was the compound illustrated in structure (4-4) in Table 4A, in micromolar (µM) and the y-axis is % inhibition of spermidine rescue of DFMO treated Chinese hamster ovary (CHO) cells, where 100% represents the viability of the DFMO only control and the 0% represents the viability of DFMO+ spermidine treated cells.

FIG. 13 is an example according to various embodiments illustrating a cytotoxicity screen in CHO cells, in which the x-axis is concentration of the tested compound, which was the compound illustrated in structure (4-4) in Table 4A, in micromolar (µM) and the y-axis is % viability of CHO cells compared to an untreated control.

FIG. 14 is an example according to various embodiments illustrating an Ant44 rescue experiment in CHO cells, in which the x-axis is concentration of the tested compound, which was the compound illustrated in structure (4-4) in Table 4A, in micromolar (µM) and the y-axis is % rescue of viability of Ant44 treated cells, where 0% represents the viability of the Ant44 control and 100% represents the viability of untreated cells (i.e. complete rescue from Ant44 toxicity).

FIG. 15 is an example according to various embodiments illustrating a DFMO rescue experiment in CHO cells, in which the x-axis is concentration of the tested compound, which was the compound illustrated in structure (4-5) in Table 4A, in micromolar (µM) and the y-axis is % inhibition of spermidine rescue of DFMO treated Chinese hamster ovary (CHO) cells, where 100% represents the viability of the DFMO only control and the 0% represents the viability of DFMO+ spermidine treated cells.

FIG. 16 is an example according to various embodiments illustrating a cytotoxicity screen in CHO cells, in which the x-axis is concentration of the tested compound, which was the compound illustrated in structure (4-5) in Table 4A, in micromolar (µM) and the y-axis is % viability of CHO cells compared to an untreated control.

FIG. 17 is an example according to various embodiments illustrating an Ant44 rescue experiment in CHO cells, in which the x-axis is concentration of the tested compound, which was the compound illustrated in structure (4-5) in Table 4A, in micromolar (µM) and the y-axis is % rescue of viability of Ant44 treated cells, where 0% represents the viability of the Ant44 control and 100% represents the viability of untreated cells (i.e. complete rescue from Ant44 toxicity).

FIG. 18 is an example according to various embodiments illustrating a DFMO rescue experiment in CHO cells, in which the x-axis is concentration of the tested compound, which was the compound illustrated in structure (4-6) in Table 4A, in micromolar (µM) and the y-axis is % inhibition of spermidine rescue of DFMO treated Chinese hamster ovary (CHO) cells, where 100% represents the viability of the DFMO only control and the 0% represents the viability of DFMO+ spermidine treated cells.

FIG. 19 is an example according to various embodiments illustrating a cytotoxicity screen in CHO cells, in which the x-axis is concentration of the tested compound, which was the compound illustrated in structure (4-6) in Table 4A, in micromolar (µM) and the y-axis is % viability of CHO cells compared to an untreated control.

FIG. 20 is an example according to various embodiments illustrating an Ant44 rescue experiment in CHO cells, in which the x-axis is concentration of the tested compound, which was the compound illustrated in structure (4-6) in Table 4A, in micromolar (µM) and the y-axis is % rescue of viability of Ant44 treated cells, where 0% represents the viability of the Ant44 control and 100% represents the viability of untreated cells (i.e. complete rescue from Ant44 toxicity).

Table 5A provides structures of the compounds represented in Table 5B. Examples shown in Table 5B demonstrate interesting SAR in the Ant44 assay. In a comparison between SBI-0814419 and SBI-0801308 where the structural difference is a 2-furyl versus a 2-methoxyphenyl, the Ant44 uptake inhibition activity favors the latter. Expansion of the piperazine ring to a diazapane along with replacement of 2-pyridyl with 2-pyrimidinyl gives SBI-0800691, which showed robust Ant44 uptake inhibition activity.

TABLE 5A

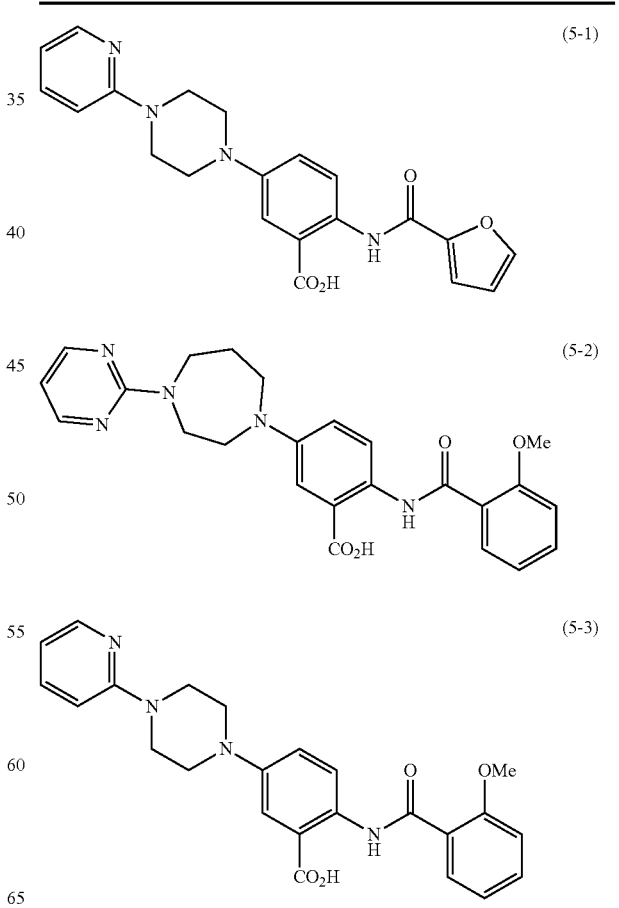

TABLE 5B

Featured samples in Ant44 blockade assay.

Figure 21:
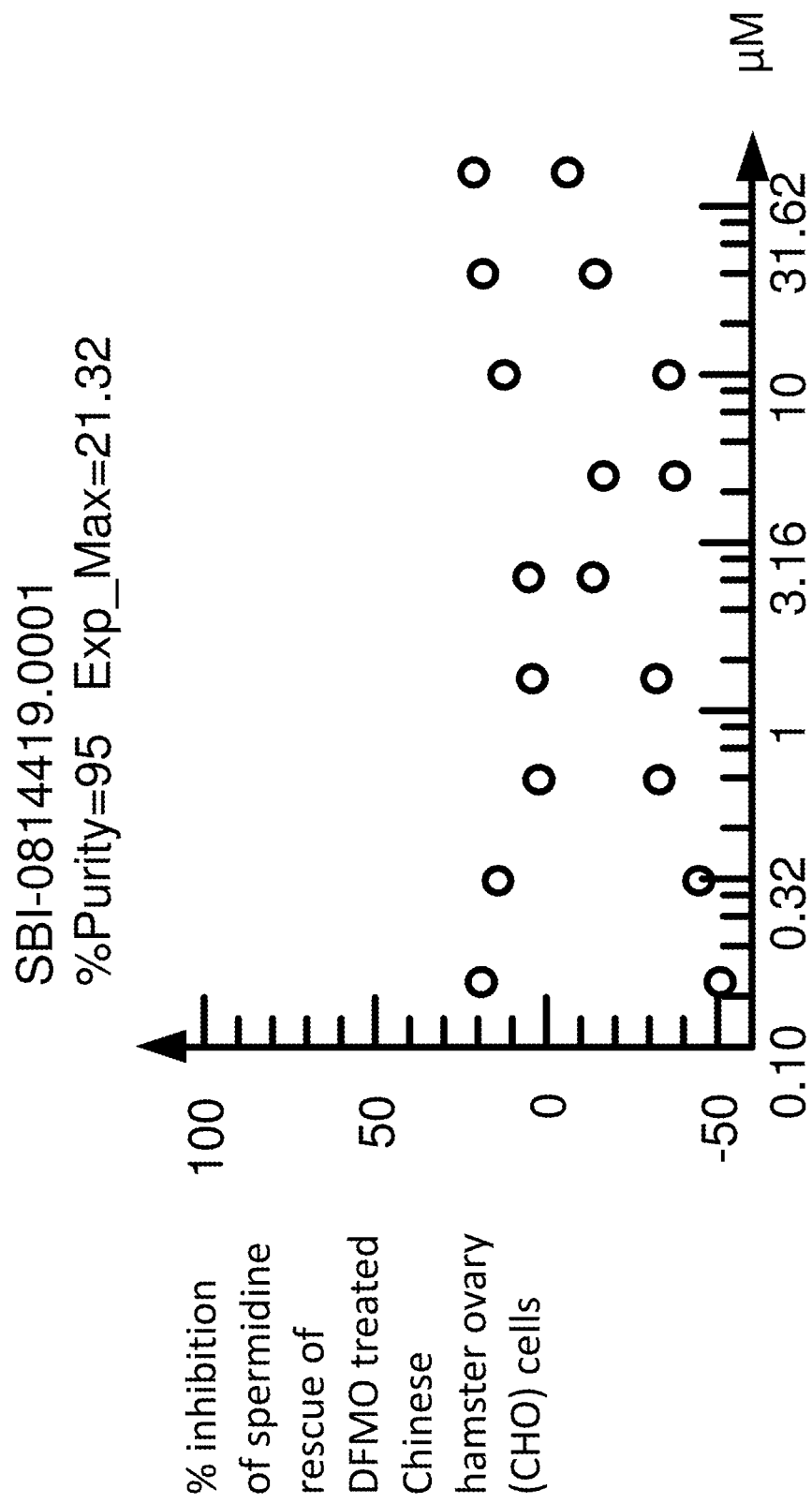
FIG. 21: is an example according to various embodiments illustrating a DFMO rescue experiment in CHO cells, in which the x-axis is concentration of the tested compound, which was the compound illustrated in structure (5-1) as shown in Table 5A, in micromolar (µM) and the y-axis is % inhibition of spermidine rescue of DFMO treated Chinese hamster ovary (CHO) cells, where 100% represents the viability of the DFMO only control and the 0% represents the viability of DFMO+ spermidine treated cells.
Figure 22:
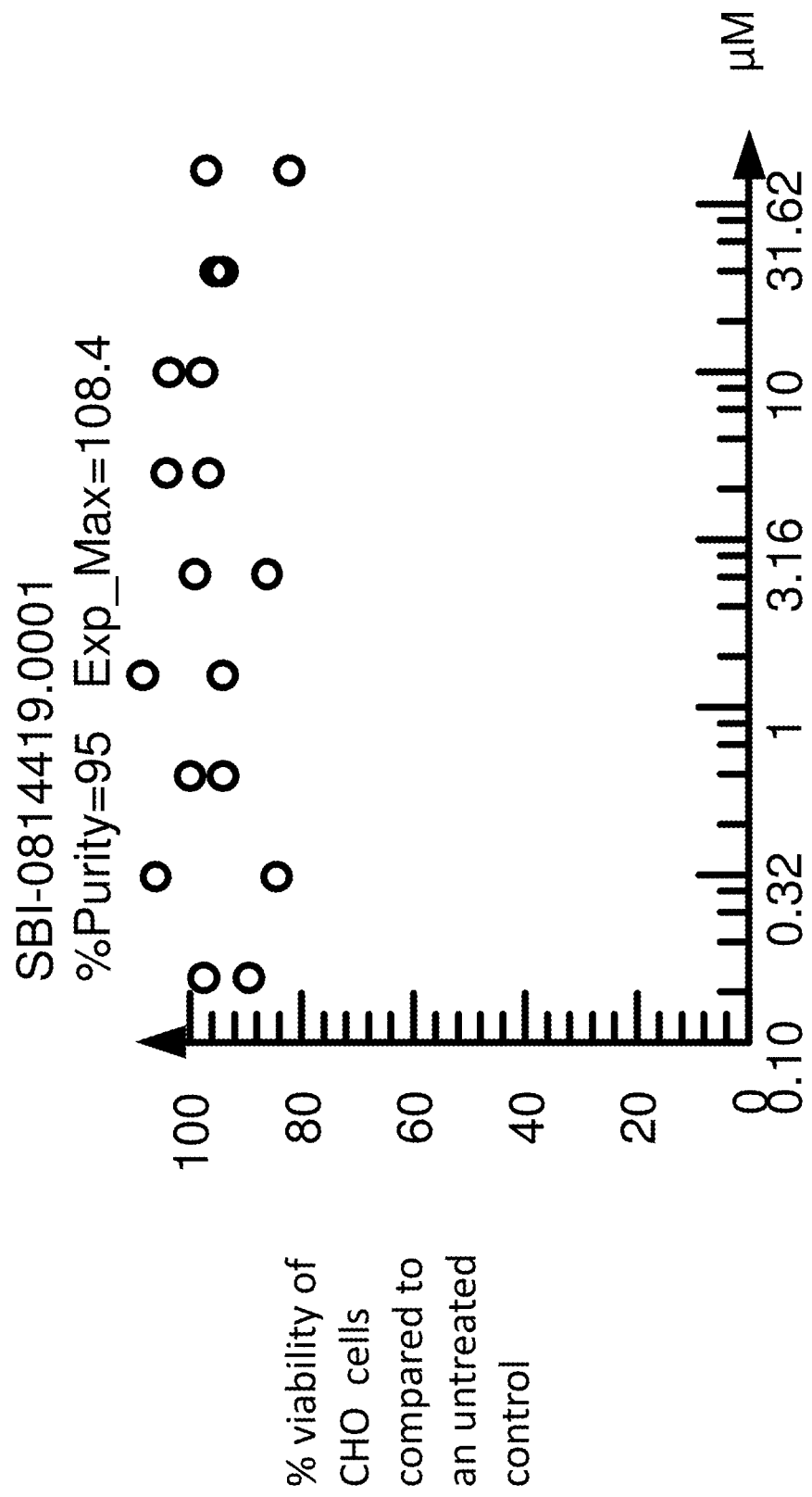
FIG. 22: is an example according to various embodiments illustrating a cytotoxicity screen in CHO cells, in which the x-axis is concentration of the tested compound, which was the compound illustrated in structure (5-1) as shown in Table 5A, in micromolar (µM) and the y-axis is % viability of CHO cells compared to an untreated control.
Figure 23:
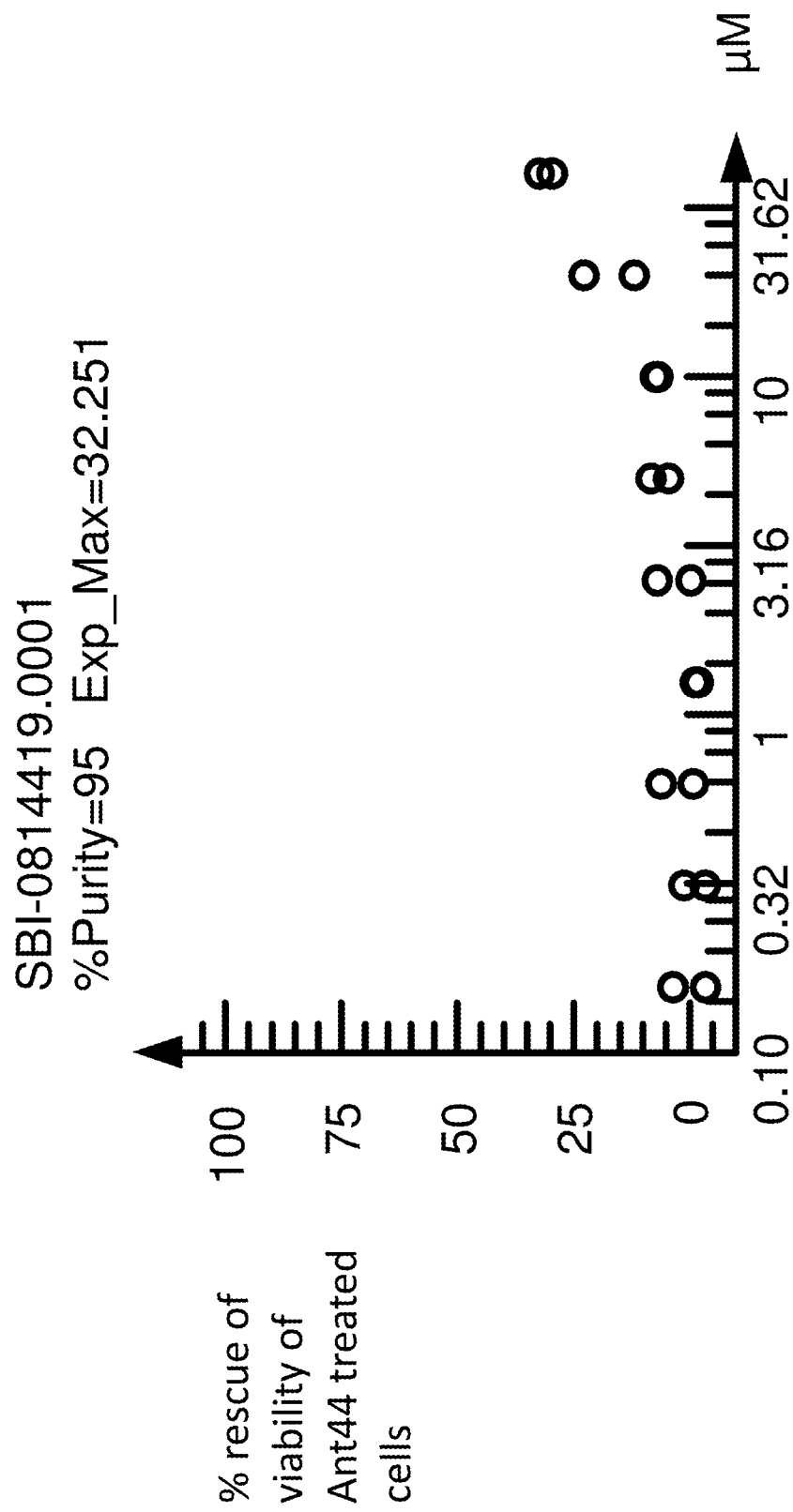
FIG. 23: is an example according to various embodiments illustrating an Ant44 rescue experiment in CHO cells, in which the x-axis is concentration of the tested compound, which was the compound illustrated in structure (5-1) as shown in Table 5A, in micromolar (µM) and the y-axis is % rescue of viability of Ant44 treated cells, where 0% represents the viability of the Ant44 control and 100% represents the viability of untreated cells (i.e. complete rescue from Ant44 toxicity)
Figure 24:
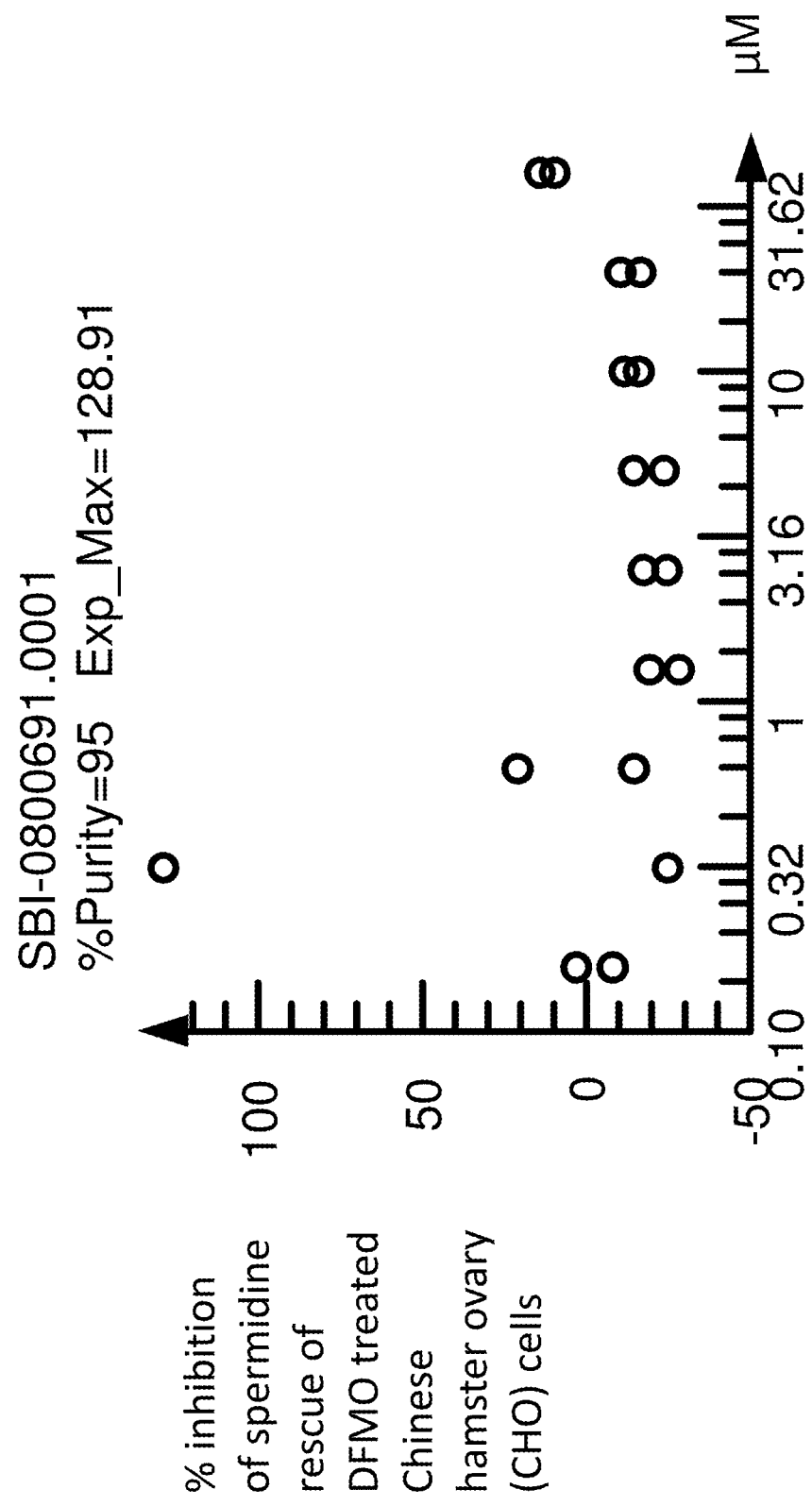
FIG. 24: is an example according to various embodiments illustrating a DFMO rescue experiment in CHO cells, in which the x-axis is concentration of the tested compound, which was the compound illustrated in structure (5-2) as shown in Table 5A, in micromolar (µM) and the y-axis is % inhibition of spermidine rescue of DFMO treated Chinese hamster ovary (CHO) cells, where 100% represents the viability of the DFMO only control and the 0% represents the viability of DFMO+ spermidine treated cells.
Figure 25:
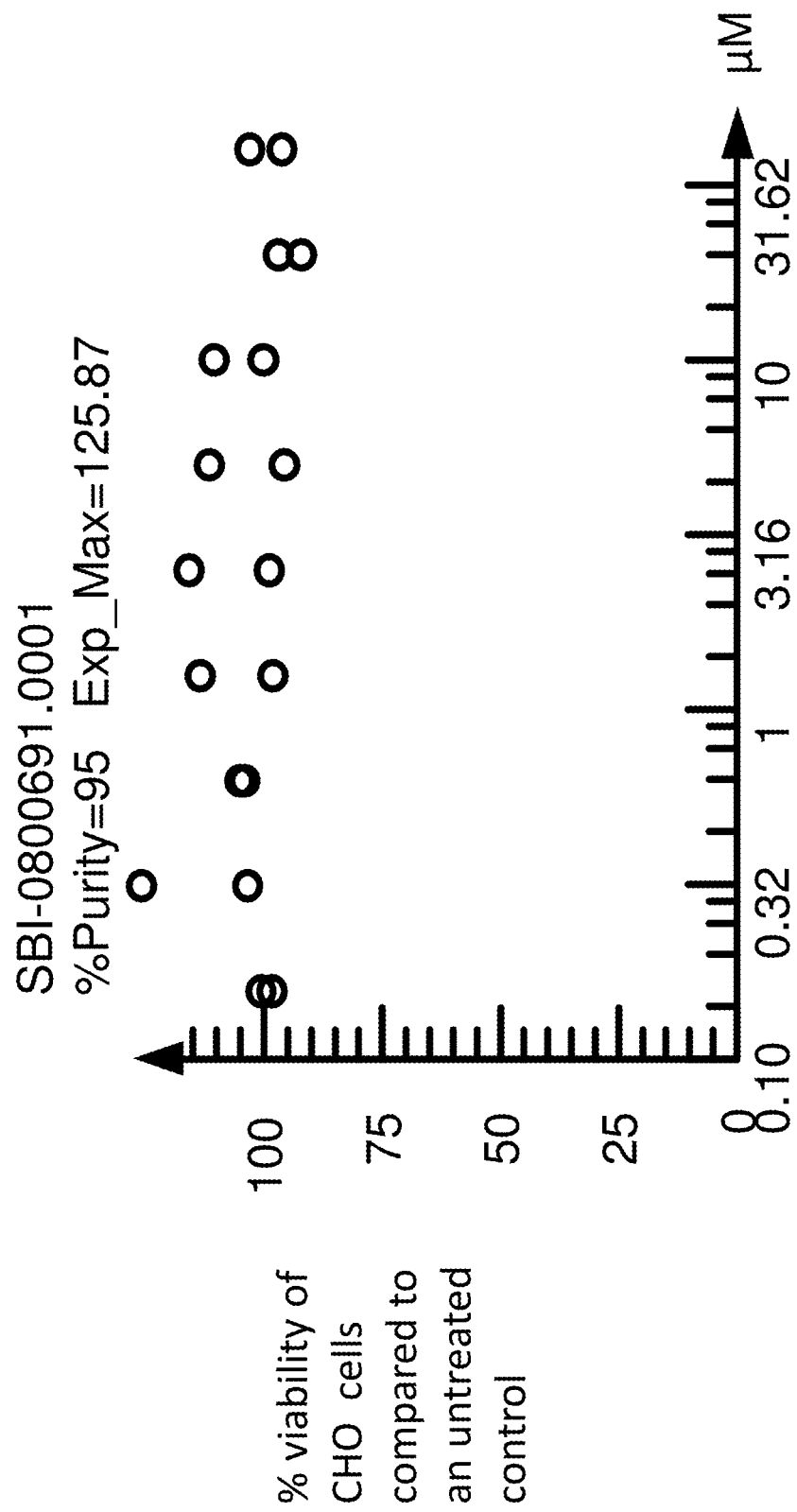
FIG. 25: is an example according to various embodiments illustrating a cytotoxicity screen in CHO cells, in which the x-axis is concentration of the tested compound, which was the compound illustrated in structure (5-2) as shown in Table 5A, in micromolar (µM) and the y-axis is % viability of CHO cells compared to an untreated control.
Figure 26:
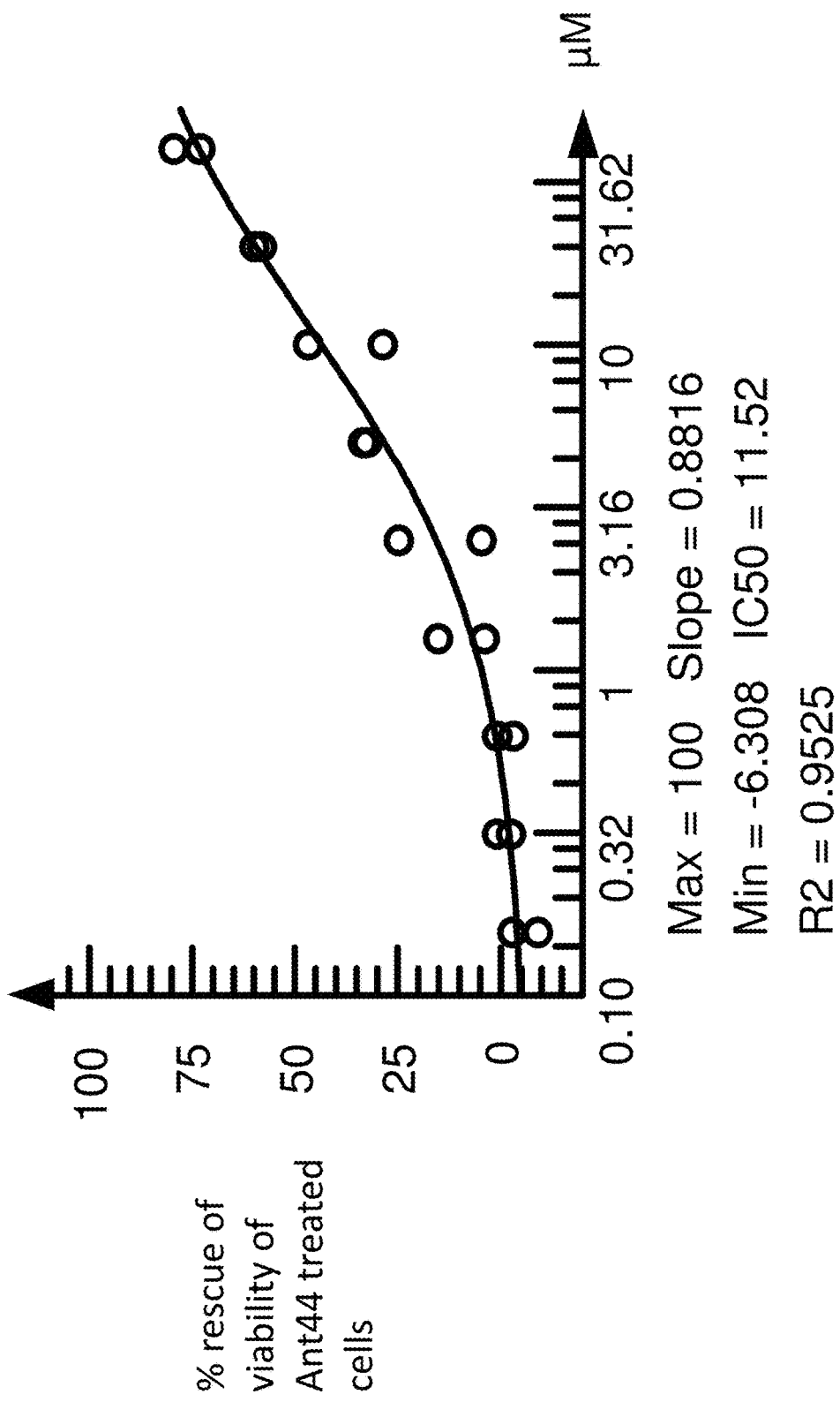
FIG. 26: is an example according to various embodiments illustrating an Ant44 rescue experiment in CHO cells, in which the x-axis is concentration of the tested compound, which was the compound illustrated in structure (5-2) as shown in Table 5A, in micromolar (µM) and the y-axis is % rescue of viability of Ant44 treated cells, where 0% represents the viability of the Ant44 control and 100% represents the viability of untreated cells (i.e. complete rescue from Ant44 toxicity)
Figure 27:
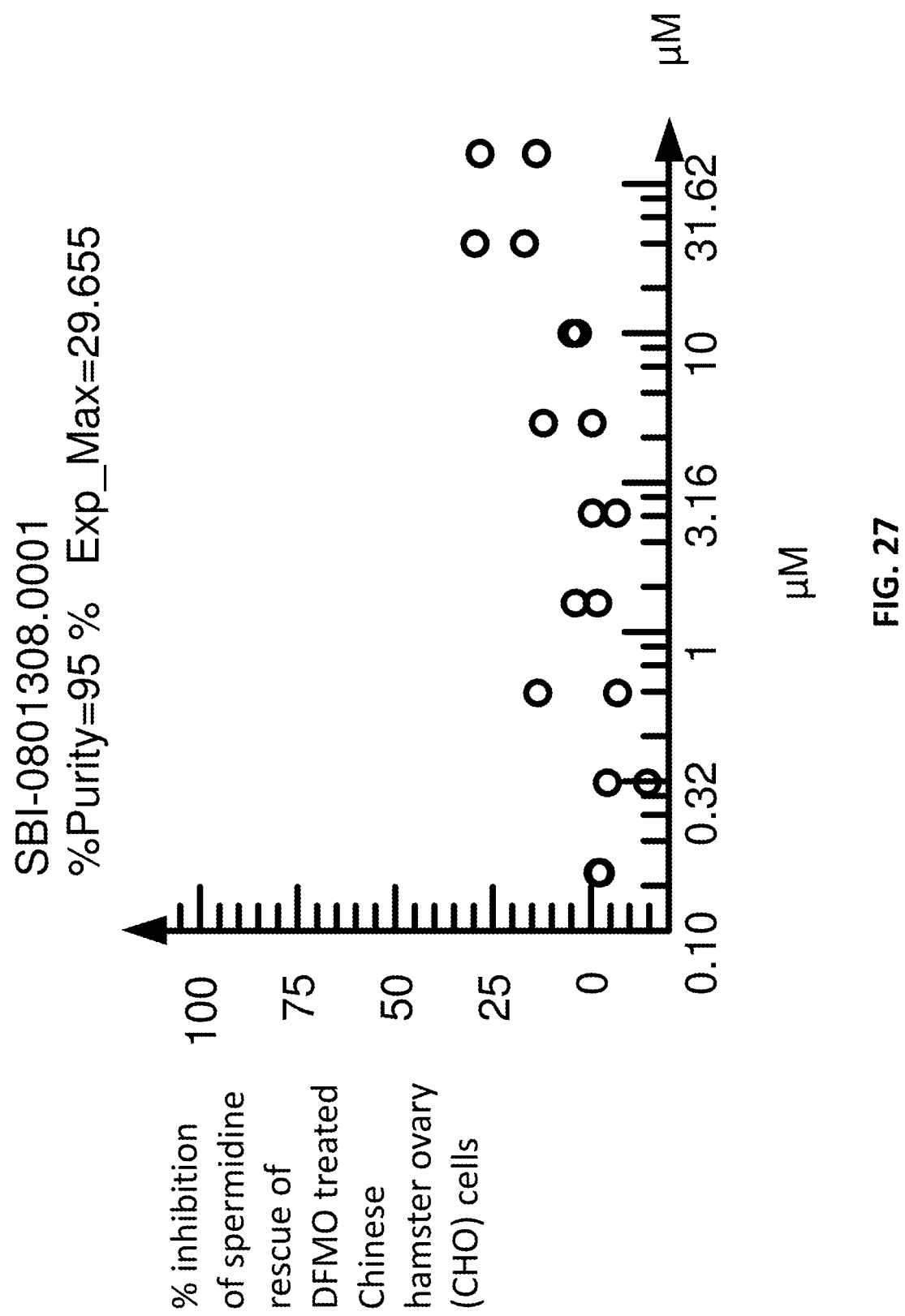
FIG. 27: is an example according to various embodiments illustrating a DFMO rescue experiment in CHO cells, in which the x-axis is concentration of the tested compound, which was the compound illustrated in structure (5-3) as shown in Table 5A, in micromolar (µM) and the y-axis is % inhibition of spermidine rescue of DFMO treated Chinese hamster ovary (CHO) cells, where 100% represents the viability of the DFMO only control and the 0% represents the viability of DFMO+ spermidine treated cells.
Figure 28:
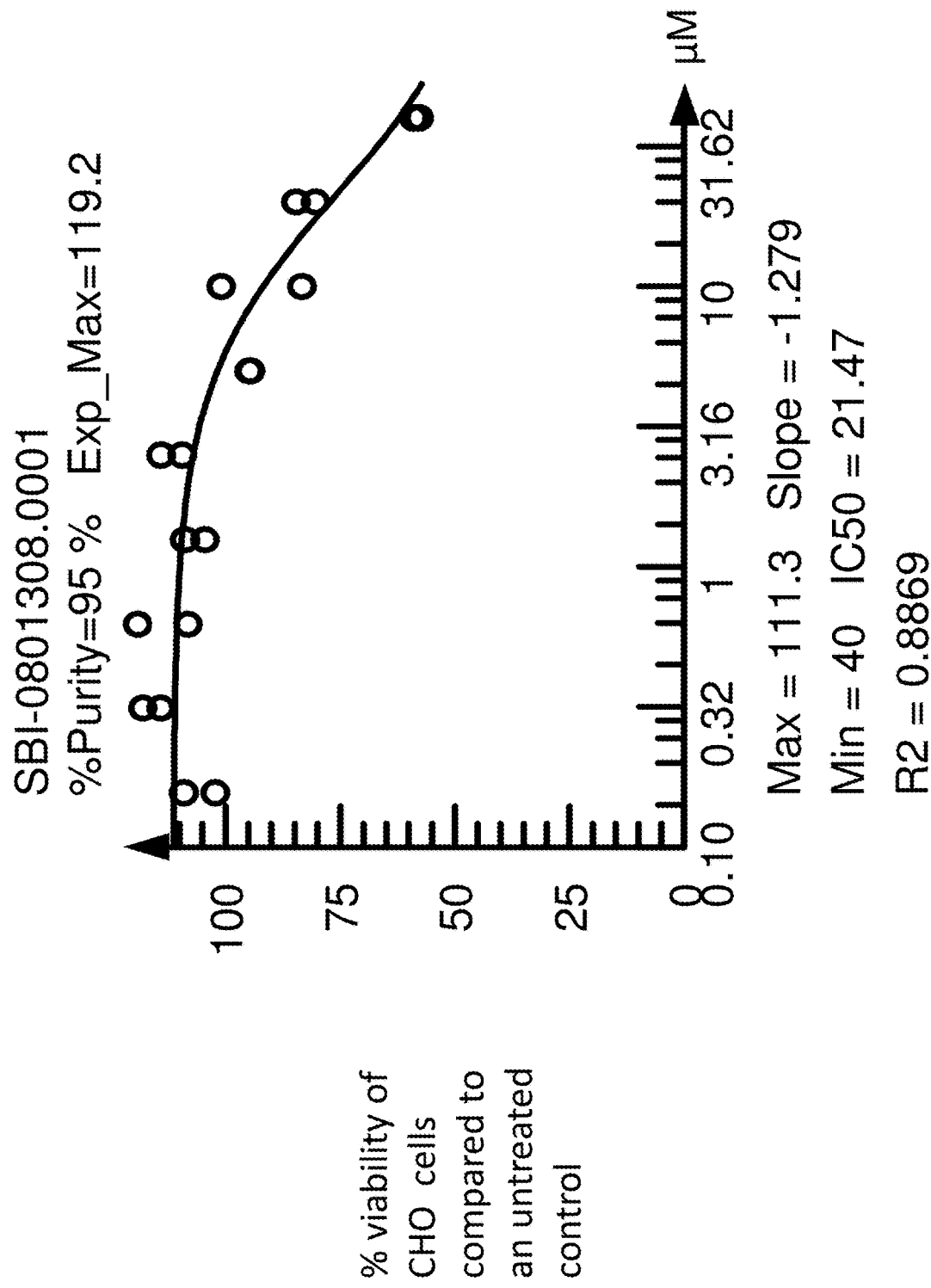
FIG. 28: is an example according to various embodiments illustrating a cytotoxicity screen in CHO cells, in which the x-axis is concentration of the tested compound, which was the compound illustrated in structure (5-3) as shown in Table 5A, in micromolar (µM) and the y-axis is % viability of CHO cells compared to an untreated control.
Figure 29:
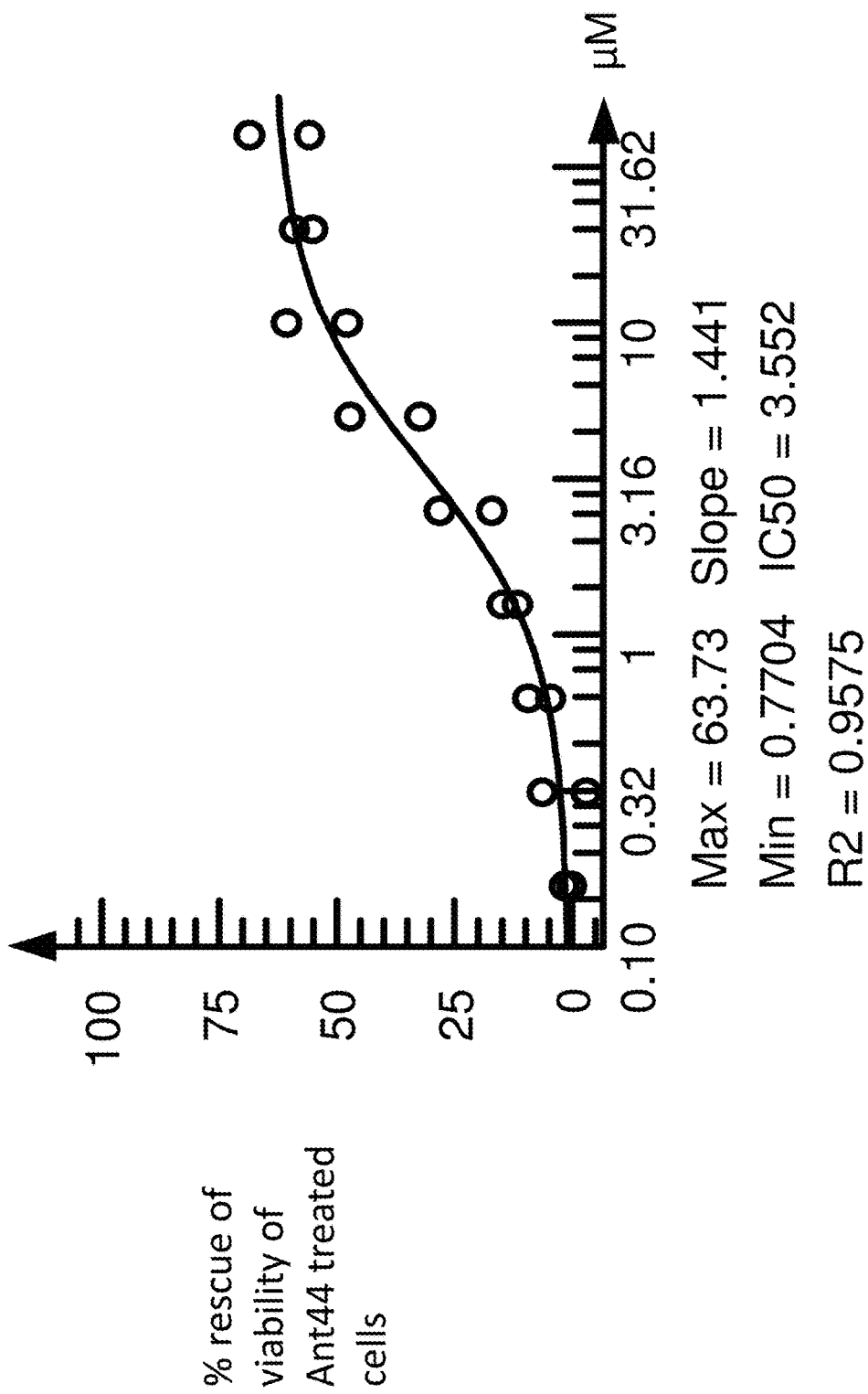
FIG. 29: is an example according to various embodiments illustrating an Ant44 rescue experiment in CHO cells, in which the x-axis is concentration of the tested compound, which was the compound illustrated in structure (5-3) as shown in Table 5A, in micromolar (µM) and the y-axis is % rescue of viability of Ant44 treated cells, where 0% represents the viability of the Ant44 control and 100% represents the viability of untreated cells (i.e. complete rescue from Ant44 toxicity).

| Structure | SBI # | DFMO/CHO $IC_{50}$ (uM) | CHO MTD $EC_{50}$ (uM) | Ant44 $IC_{50}$ (uM) | L3.6pl $EC_{50}$ (uM) | L3.6pl MTD (uM) |
|---|---|---|---|---|---|---|
| (5-1) | 0814419 | N/A See: FIG. 21 | N/A See: FIG. 22 | trace See: FIG. 23 | (10) | (>10) |
| (5-2) | 0800691 | trace See: FIG. 24 | N/A See: FIG. 25 | (12) See: FIG. 26 | | |
| (5-3) | 0801308 | trace See: FIG. 27 | (22) See: FIG. 28 | (3.6) See: FIG. 29 | | |

Table 5 includes references to FIGS. 21-29.

FIG. 21 is an example according to various embodiments illustrating a DFMO rescue experiment in CHO cells, in which the x-axis is concentration of the tested compound, which was the compound illustrated in structure (5-1) as shown in Table 5A, in micromolar (µM) and the y-axis is % inhibition of spermidine rescue of DFMO treated Chinese hamster ovary (CHO) cells, where 100% represents the viability of the DFMO only control and the 0% represents the viability of DFMO+ spermidine treated cells.

FIG. 22 is an example according to various embodiments illustrating a cytotoxicity screen in CHO cells, in which the x-axis is concentration of the tested compound, which was the compound illustrated in structure (5-1) as shown in Table 5A, in micromolar (µM) and the y-axis is % viability of CHO cells compared to an untreated control.

FIG. 23 is an example according to various embodiments illustrating an Ant44 rescue experiment in CHO cells, in which the x-axis is concentration of the tested compound, which was the compound illustrated in structure (5-1) as shown in Table 5A, in micromolar (µM) and the y-axis is % rescue of viability of Ant44 treated cells, where 0% represents the viability of the Ant44 control and 100% represents the viability of untreated cells (i.e. complete rescue from Ant44 toxicity).

FIG. 24 is an example according to various embodiments illustrating a DFMO rescue experiment in CHO cells, in which the x-axis is concentration of the tested compound, which was the compound illustrated in structure (5-2) as shown in Table 5A, in micromolar (µM) and the y-axis is % inhibition of spermidine rescue of DFMO treated Chinese hamster ovary (CHO) cells, where 100% represents the viability of the DFMO only control and the 0% represents the viability of DFMO+ spermidine treated cells.

FIG. 25 is an example according to various embodiments illustrating a cytotoxicity screen in CHO cells, in which the x-axis is concentration of the tested compound, which was the compound illustrated in structure (5-2) as shown in Table 5A, in micromolar (µM) and the y-axis is % viability of CHO cells compared to an untreated control.

FIG. 26 is an example according to various embodiments illustrating an Ant44 rescue experiment in CHO cells, in which the x-axis is concentration of the tested compound, which was the compound illustrated in structure (5-2) as shown in Table 5A, in micromolar (µM) and the y-axis is % rescue of viability of Ant44 treated cells, where 0% represents the viability of the Ant44 control and 100% represents the viability of untreated cells (i.e. complete rescue from Ant44 toxicity).

FIG. 27 is an example according to various embodiments illustrating a DFMO rescue experiment in CHO cells, in which the x-axis is concentration of the tested compound, which was the compound illustrated in structure (5-3) as shown in Table 5A, in micromolar (µM) and the y-axis is % inhibition of spermidine rescue of DFMO treated Chinese hamster ovary (CHO) cells, where 100% represents the viability of the DFMO only control and the 0% represents the viability of DFMO+ spermidine treated cells.

FIG. 28 is an example according to various embodiments illustrating a cytotoxicity screen in CHO cells, in which the x-axis is concentration of the tested compound, which was the compound illustrated in structure (5-3) as shown in Table 5A, in micromolar (µM) and the y-axis is % viability of CHO cells compared to an untreated control.

FIG. 29 is an example according to various embodiments illustrating an Ant44 rescue experiment in CHO cells, in which the x-axis is concentration of the tested compound, which was the compound illustrated in structure (5-3) as shown in Table 5A, in micromolar (µM) and the y-axis is % rescue of viability of Ant44 treated cells, where 0% represents the viability of the Ant44 control and 100% represents the viability of untreated cells (i.e. complete rescue from Ant44 toxicity).

ADME data was obtained in vitro on a representative example, SBI-0800678, (compound 4-3 in Table 4A) and is summarized in Table 6. The sample was found to be poorly soluble in PBS and have good microsomal and plasma stability.

TABLE 6

ADME results for SBI-0800678

| Solubility (µg/mL) | | Microsomal Stability % remaining at 1 hour | | Plasma Stability % remaining at 3 hours | |
|---|---|---|---|---|---|
| pH 5.0 | 0.3 | Human | 52.0 | Human | 88.0 |
| pH 6.2 | 0.1 | Mouse | 60.4 | Mouse | 83.1 |
| pH 7.4 | >0.1 | Rat | 58.0 | Rat | 55.3 |

In summary, the vast majority of compounds displaying activity in the DFMO assay had similar potency in the general toxicity assay. Given that cytotoxic compounds typically generate a false positive result in the DFMO assay, one must examine the dose response data carefully to identify truly active compounds. The examples in Table 4 indicate there is hope that future work could be done to further separate inhibition of spermidine rescue from cytotoxicity. While fewer compounds were found to be active in the Ant44 assay, the SAR is encouraging that more potent and efficacious compounds could be prepared. Table 7 provides a comprehensive SAR $IC_{50}$ data for a variety of compounds, according to Formula (7-1)

TABLE 7

Formula (7-1)

| SBI- | R1 | R2 | R3 | DFMO assay | Ant44assay | Cytotox |
|---|---|---|---|---|---|---|
| 0800660 | 4-OMe—Ph | 3-CN | cHexyl | 23 | >40 | 17 |
| 0800692 | CO$_2$Et | 2-CO$_2$H | 4-OMe—Ph | >40 | >40 | 34 |
| 0800690 | CH$_2$CONEt$_2$ | 2-CO$_2$H | 4-OMe—Ph | >40 | >40 | 28 |
| 0800689 | CH$_2$CONH(CH$_2$)$_2$OMe | 2-CO$_2$H | 4-OMe—Ph | >40 | ND | >40 |
| 0800685 | cHexyl | 2-CO$_2$H | 4-OMe—Ph | >40 | ND | >40 |
| 0800684 | 3-Cl—Ph | 2-CO$_2$H | 4-OMe—Ph | 17 | ND | 20 |
| 0800683 | 2-OEt—Ph | 2-CO$_2$H | 4-OMe—Ph | 20 | >40 | 37 |
| 0800682 | 2-Cl—Ph | 2-CO$_2$H | 4-OMe—Ph | 27 | >40 | 28 |
| 0800681 | 2-F—Ph | 2-CO$_2$H | 4-OMe—Ph | 33 | >40 | 25 |
| 0800680 | 4-OMe—Ph | 2-CO$_2$H | 4-OMe—Ph | >40 | >40 | >40 |
| 0800679 | Ph | 2-CO$_2$H | 4-OMe—Ph | 15 | >40 | 17 |
| 0800678 | 2-OMe—Ph | 2-CO$_2$H | 4-OMe—Ph | 26 | 9 | >40 |
| 0800677 | cHexyl | 2-CO$_2$H | 4-F—Ph | >40 | ND | >40 |
| 0800676 | 2,3-di-Me—Ph | 2-CO$_2$H | 2-OMe—Ph | 23 | 2 | 28 |
| 0800673 | 2,3-di-Me—Ph | 2-CO$_2$H | 3-Cl—Ph | 8 | ND | 10 |
| 0800672 | 2,3-di-Me—Ph | 2-CO$_2$H | 2-Cl—Ph | 22 | ND | 26 |
| 0800675 | 2-Cl—Ph | 2-CO$_2$H | CH$_2$-(4-Me—Ph) | 32 | 16 | >40 |
| 0800674 | 4-Ac—Ph | 2-CO$_2$H | 4-OMe—Ph | 21 | >40 | 20 |
| 0800671 | 3-Me—Ph | 2-CO$_2$H | 4-OMe—Ph | 16 | >40 | 22 |
| 0800670 | 2-OMe—Ph | 2-CO$_2$H | 2-Cl—Ph | 26 | 16 | 36 |
| 0800668 | 2-Me-5-Cl—Ph | 3-CO$_2$H | 2-Me—Ph | >40 | >40 | >40 |
| 0800667 | 2,5-di-Me—Ph | 3-CO$_2$H | 4-Cl—Ph | >40 | ND | >40 |
| 0800666 | 2-OMe—Ph | 3-CO$_2$H | 2-thienyl | 27 | >40 | >40 |
| 0800665 | 2-F—Ph | 3-CO$_2$H | 4-Cl—Ph | >40 | ND | >40 |
| 0800664 | 2-OMe—Ph | 3-CO$_2$H | Ph | >40 | ND | >40 |
| 0800669 | 2-Me-5-Cl—Ph | 3-CO$_2$H | 4-Me—Ph | 5 | >40 | 12 |
| 0754480 | 2-Me-5-Cl—Ph | 2-CO$_2$H | CH$_2$-(4-OMe—Ph) | 25 | 32 | 24 |
| 0800662 | 2-Me-5-Cl—Ph | 3-CO$_2$H | 4-OMe—Ph | 5 | >40 | 14 |
| 0754479 | 2-Me-5-Cl—Ph | 2-CO$_2$H | 4-OMe—Ph | 8 | >40 | 13 |
| 0351221 | 2-Me-5-Cl—Ph | 2-CO$_2$H | 4-OMe—Ph | 21 | 2 | 19 |
| 0801324 | 2-Me-5-Cl—Ph | 2-CO$_2$H | 2,4-di-OMe—Ph | >40 | >40 | >40 |
| 0814425 | 2-Me—Bz | H | t-Bu | 2 | >40 | 2 |
| 0814419 | 2-pyridyl | 2-CO$_2$H | 2-furan | >40 | >40 | >40 |
| 0814416 | (CH$_2$)$_3$—Ph | 2-CO$_2$H | 2-OMe—Ph | >40 | >40 | >40 |
| 0814415 | (CH$_2$)$_2$—Ph | 2-CO$_2$H | 2-OMe—Ph | >40 | >40 | >40 |
| 0814414 | Bn | 2-CO$_2$H | 2-OMe—Ph | >40 | >40 | >40 |
| 0814424 | CO—(2-pyridyl) | 2-CO$_2$H | 2-OMe—Ph | >40 | >40 | >40 |
| 0814421 | CH$_2$—(2-pyridyl) | 2-CO$_2$H | 2-OMe—Ph | 10 | >40 | >40 |
| 0801308 | 2-pyridyl | 2-CO$_2$H | 2-OMe—Ph | >40 | 4 | 21 |
| 0814417 | 2-pyridyl | H | 2-OMe—Ph | >40 | >40 | 14 |
| 0801722 | 2-Me-5-Cl—Ph | 2-CO$_2$Me | 4-OMe—Ph | >40 | >40 | >40 |
| 0801723 | 2-Me-5-Cl—Ph | 2-CO$_2$Me | 2,4-di-OMe—Ph | >40 | >40 | >40 |
| 0801724 | 2-Me-5-Cl—Ph | 2-CO$_2$Me | 2-OMe—Ph | >40 | >40 | >40 |
| 0814423 | (structure: 2-pyridyl-piperazine-CH$_2$-phenyl(CO$_2$H)-NHC(O)-(2-OMe-phenyl)) | | | >40 | >40 | >40 |
| 0814422 | (structure: 2-pyridyl-piperazine-CH$_2$-phenyl(CO$_2$Me)-NHC(O)-(2-OMe-phenyl)) | | | >20 | >20 | >20 |

TABLE 7-continued
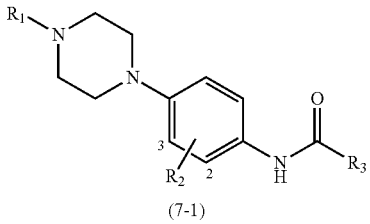
| | Formula (7-1) | | | SAR IC$_{50}$ μM ND = no data | | |
|---|---|---|---|---|---|---|
| SBI- | R1 | R2 | R3 | DFMO assay | Ant44assay | Cytotox |
| 0814418 | 4-phenylpiperidine | | 2-OMe benzamide (with CO$_2$H at R2) | 21 | 18 | >40 |
| 0814420 | 4-phenoxypiperidine | | 2-OMe benzamide (with CO$_2$H at R2) | 19 | 32 | >40 |
| 0800691 | 1-(pyrimidin-2-yl)-1,4-diazepane | | 4-OMe benzamide (with CO$_2$H at R2) | >40 | 12 | >40 |
| 0801326 | 4-(5-chloro-2-methylphenyl)piperazine | | 4-OMe phenylsulfonamide (with CO$_2$H at R2) | >40 | >40 | >40 |

TABLE 7-continued
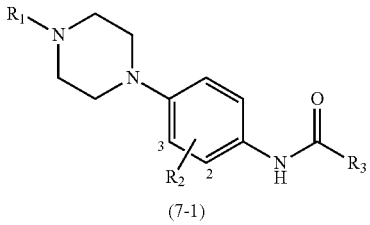
(7-1)
| Formula (7-1) | | | SAR IC$_{50}$ μM ND = no data | | |
|---|---|---|---|---|---|
| SBI- | R1 | R2 | R3 | DFMO assay | Ant44assay | Cytotox |
| 0372958 | 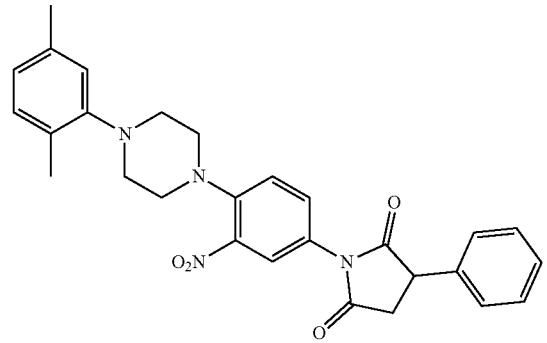 | | | 27 | ND | 32 |
| 0800661 | 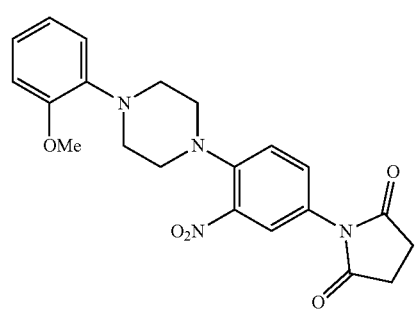 | | | 30 | >40 | 27 |
| 0800663 | 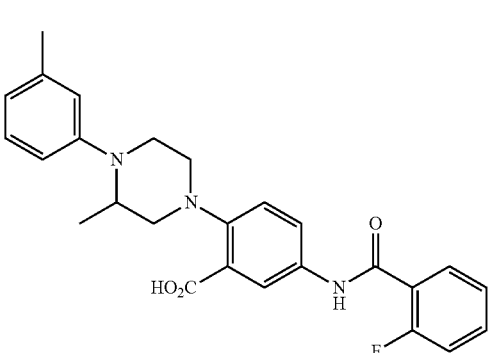 | | | >40 | ND | >40 |
| 0800687 | 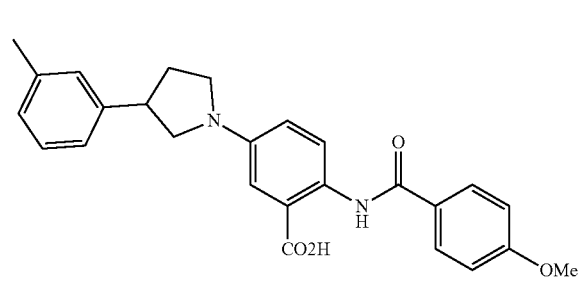 | | | >40 | >40 | >40 |

TABLE 7-continued

| | Formula (7-1) | | | SAR IC$_{50}$ μM ND = no data | | |
|---|---|---|---|---|---|---|
| SBI- | R1 | R2 | R3 | DFMO assay | Ant44assay | Cytotox |
| 0800693 | | | | >40 | >40 | 22 |
| 800694 | | | | >40 | ND | >40 |

From this data, a general pharmacophore was established.

Preferred compounds had either R$_6$ or R$_7$=COOH, R$_3$=OMe or OPh, n=1, R$_8$=OMe, OEt, OH, Me, or CH$_2$OH, R$_{11}$=Cl, OMe or H and R$_1$, R$_2$, R$_4$, R$_5$, R$_6$ (when R$_7$=COOH),R$_7$ (when R$_6$=COOH), R$_9$, R$_{10}$ and R$_{12}$-R$_{14}$=H, and X=Y=C.

Other preferred compounds had R$_6$=COOH, R$_3$=OMe or OPh, n=1, R$_8$=R$_{12}$=lone pair, R$_{11}$=H, and R$_1$, R$_2$, R$_4$, R$_5$, R$_7$, R$_9$, R$_{10}$, R$_{13}$, and R$_{14}$=H and X=Y=N.

It should be noted that one can consider the methyl ester of the carboxylic acid at R6 as a possible pro-drug design, where the ester would be cleaved in vivo by esterases to generate the active drug.

The following compounds were identified.

DFMO targets

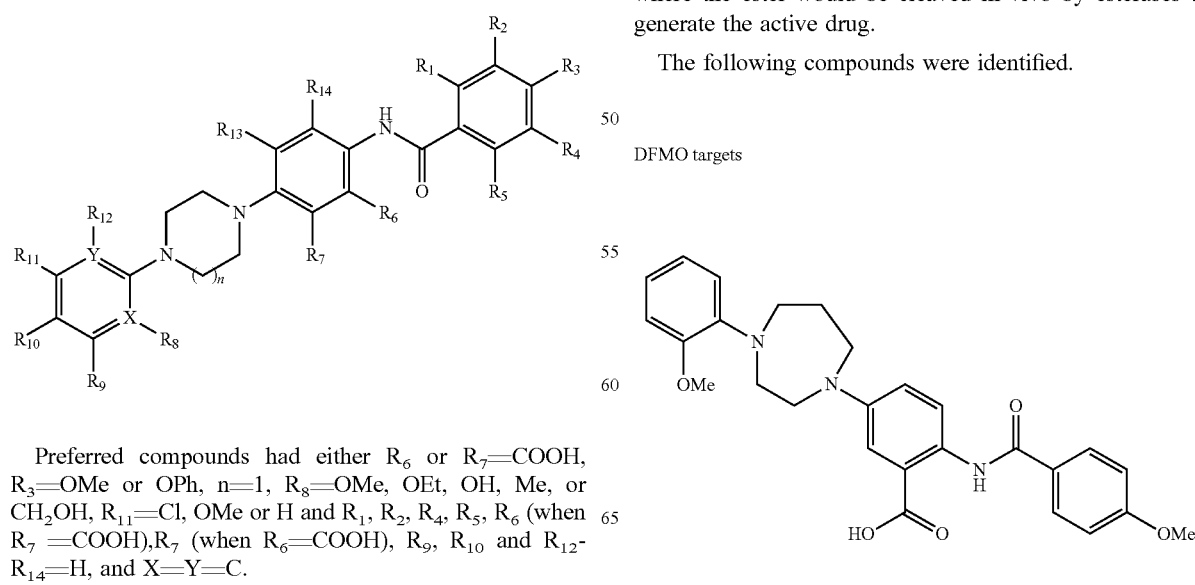

73
-continued
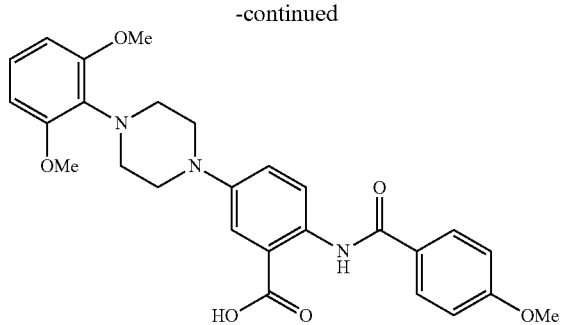
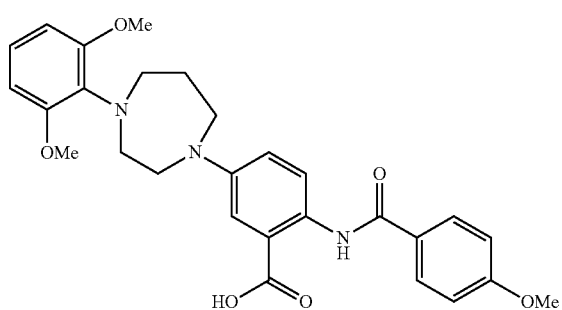
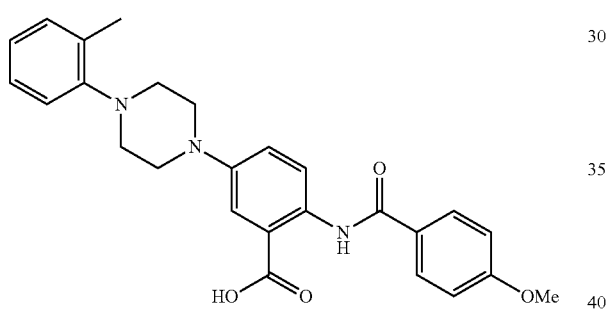
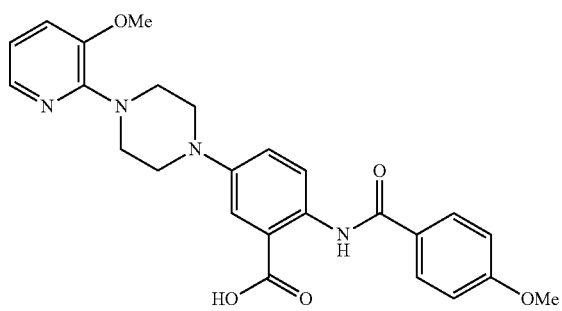
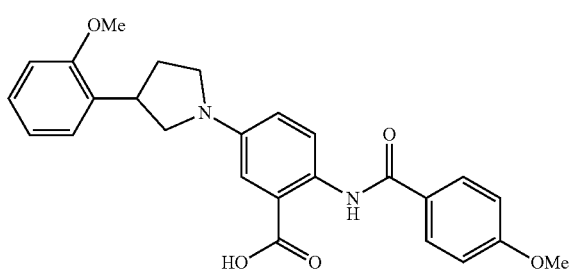
74
-continued
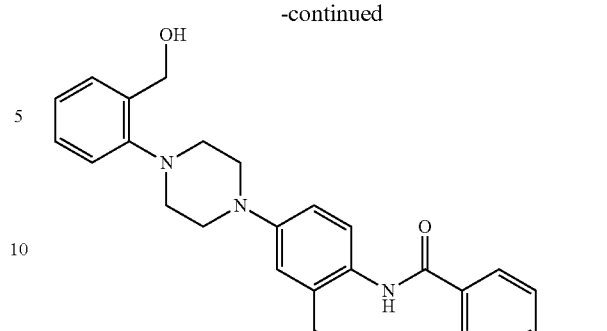
new Ant44 targets
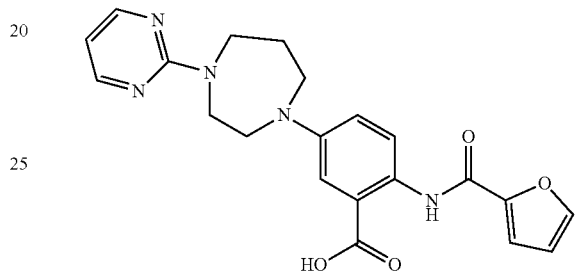
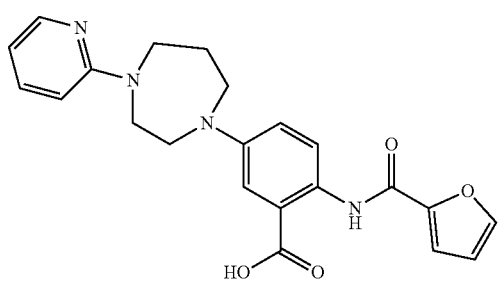
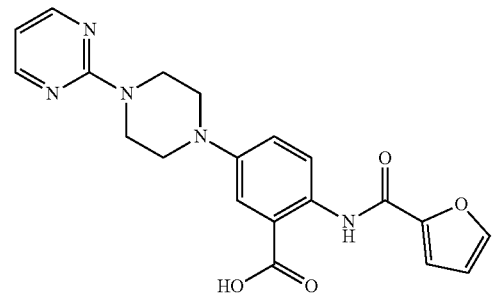
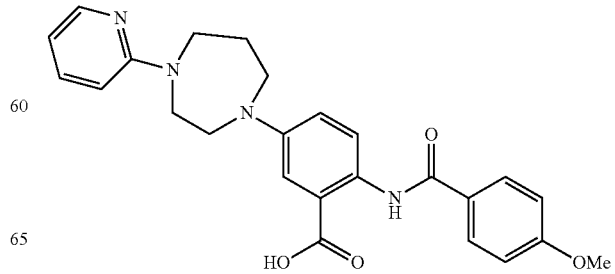

-continued

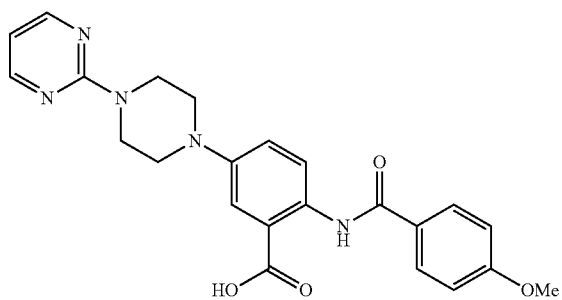

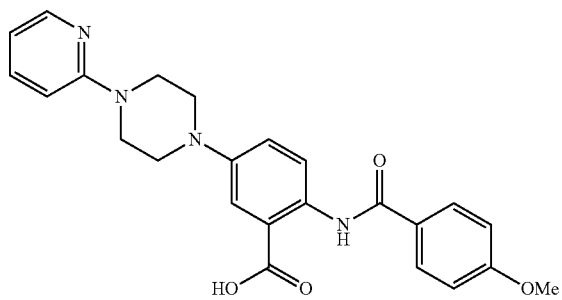

Example 4

The following reaction pathway was employed.

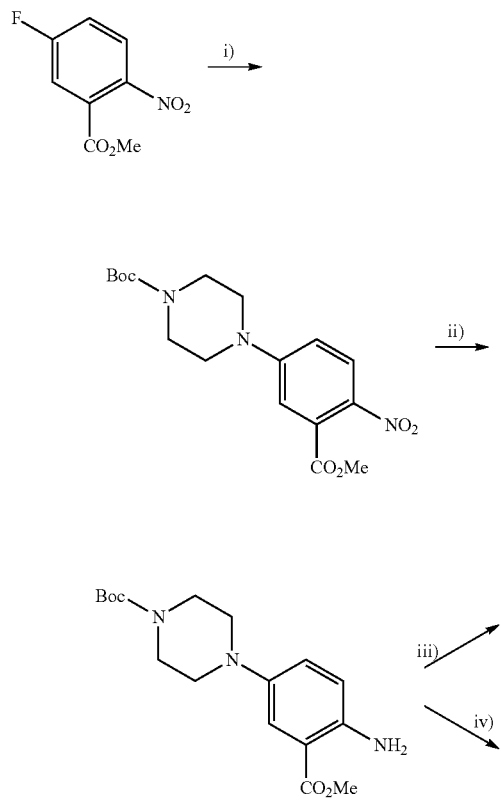

-continued

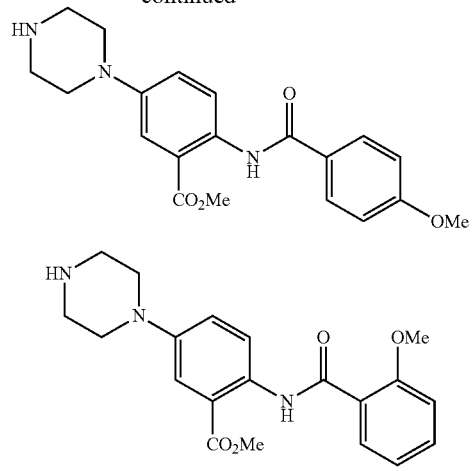

Conditions: i) 1-Boc-piperazine, Et₃N, 1,4-dioxane, reflux; ii) Zn, HOAc; iii) 4-methoxybenzoyl chloride, Et₃N, DMAP, 1,4-dioxane then TFA; iv) 2-methoxybenzoyl chloride, Et₃N, DMAP, 1,4-dioxane then TFA.

PRM0208-32-1. tert-butyl 4-(3-(methoxycarbonyl)-4-nitrophenyl)piperazine-1-carboxylate was synthesized. A solution of methyl 5-fluoro-2-nitrobenzoate (1.09 g, 5.48 mmol), tert-butyl piperazine-1-carboxylate (1.02 g, 5.48 mmol), and triethylamine (0.78 mL, 5.6 mmol) in dioxane (30 mL) was stirred at reflux overnight. The solvent was removed in vacuo and the residue partitioned with ethyl acetate and water. The organic phase was evaporated to an oil which was used without further purification. Yield=1.96 g. (98%).

Example 5

PRM0208-32-3. tert-butyl 4-(4-amino-3-(methoxycarbonyl)phenyl)piperazine-1-carboxylate was synthesized. A solution of tert-butyl 4-(3-(methoxycarbonyl)-4-nitrophenyl)piperazine-1-carboxylate (1.6 g, 4.38 mmol) in acetic acid (30 mL) was treated with powdered zinc (1.0 g, 15.3 mmol) portionwise over 10 minutes to control the exothermic reaction. The mixture was let stir overnight, filtered, and evaporated to provide an oil which was partitioned with ethyl acetate and aqueous potassium carbonate. The organic phase was evaporated and the crude product purified on silica gel eluting with 50% ethyl acetate in hexanes. Yield=1.1 g. (75%).

Example 6

PRM0208-34-1, PRM0208-34-2. methyl 2-(4-methoxybenzamido)-5-(piperazin-1-yl)benzoate was synthesized. A solution of tert-butyl 4-(4-amino-3-(methoxycarbonyl)phenyl)piperazine-1-carboxylate (410 mg, 1.22 mmol), 4-methoxybenzoyl chloride (0.19 mL, 1.38 mmol), triethylamine (0.21 mL, 1.51 mmol), and catalytic DMAP in dioxane (10 mL) was stirred for 30-60 minutes at which time LCMS indicated the limiting reagent was consumed. The solvent was removed in vacuo and the residue was purified on silica gel eluting with 20-50% ethyl acetate in hexanes. Yield=400 mg. (70%). The Boc protecting group was removed with 20% trifluoroacetic acid in dichloromethane at ambient temperature over 2.5 hours. The solvent was removed in vacuo and the residue partitioned with ethyl acetate and aqueous sodium bicarbonate. The precipitated product was collected by filtration and was used without further purification. Yield=300 mg. (95%).

Example 7

PRM0208-59-1, PRM0208-59-2. methyl 2-(2-methoxybenzamido)-5-(piperazin-1-yl)benzoate was synthesized. A solution of tert-butyl 4-(4-amino-3-(methoxycarbonyl)phenyl)piperazine-1-carboxylate (290 mg, 0.86 mmol), 2-methoxybenzoyl chloride (0.12 mL, 0.88 mmol), triethylamine (0.14 mL, 1.0 mmol), and catalytic DMAP in dioxane (10 mL) was stirred overnight. The solvent was removed in vacuo and the residue was purified on silica gel eluting with 30-60% ethyl acetate in hexanes. Yield=362 mg. (89%). The Boc protecting group was removed with 20% trifluoroacetic acid in dichloromethane at ambient temperature over 2.5 hours. The solvent was removed in vacuo and the residue partitioned with ethyl acetate and aqueous potassium carbonate. The organic phase was evaporated to provide a yellow solid which was used without further purification. Yield=270 mg. (95%).

Example 8

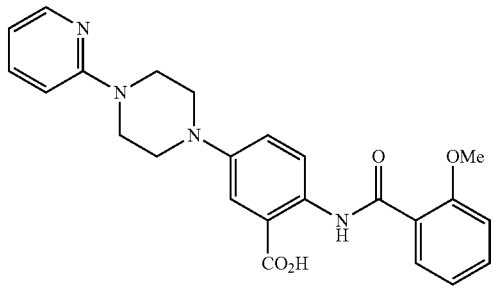 [SMILES: COc1ccccc1C(=O)Nc1ccc(N2CCN(c3ccccn3)CC2)cc1C(=O)O]

SBI-0801308 (SP0210-84B) methyl 2-(2-methoxybenzamido)-5-(4-(pyridin-2-yl)piperazin-1-yl)benzoate, as shown in the Formula above, was synthesized. A solution of crude methyl 2-amino-5-(4-(pyridin-2-yl)piperazin-1-yl)benzoate (25 mg, 0.08 mmol) and triethylamine (0.022 mL, 0.16 mmol) in dry dichloromethane (2 mL) was treated with O-anisoyl chloride (0.014 mL, 0.096 mmol) and was stirred at room temperature overnight. The reaction was partitioned between water and dichloromethane then the volatile organics were evaporated in vacuo to afford crude methyl 2-(2-methoxybenzamido)-5-(4-(pyridin-2-yl)piperazin-1-yl)benzoate (22 mg, 62%). H NMR (500 MHz, Chloroform-d) δ 11.99 (s, 1H), 8.81 (d, J=9.3 Hz, 1H), 8.21 (dd, J=11.1, 5.9 Hz, 2H), 7.61 (d, J=3.2 Hz, 1H), 7.50 (dt, J=21.8, 7.0 Hz, 2H), 7.25 (d, J=9.2 Hz, 1H), 7.09 (dd, J=8.7, 5.6 Hz, 1H), 7.04 (t, J=5.7 Hz, 1H), 6.77-6.62 (m, 2H), 4.09 (d, J=4.1 Hz, 3H), 3.94 (d, J=3.9 Hz, 3H), 3.73 (d, J=5.2 Hz, 4H), 3.31 (d, J=5.2 Hz, 4H). LRMS (ESI+ve): Calculated for $C_{25}H_{26}N_4O_4$, [M+H]=447.2, observed [M+H]=447.35.

Example 9

2-(2-methoxybenzamido)-5-(4-(pyridin-2-yl)piperazin-1-yl)benzoic acid was synthesized. Crude methyl 2-(2-methoxybenzamido)-5-(4-(pyridin-2-yl)piperazin-1-yl)benzoate (max 22 mg, 0.049 mmol) and LiGH (11.8 mg, 0.49 mmol) were charged into vial followed by addition of methanol (1 mL) and water (4 mL) and mix heated at 60° C. overnight. LCMS analysis of aliquot indicated only partial conversion to product. The reaction mix was cooled to room temperature and volatiles evaporated in vacuo overnight. The residue was resuspended in 1,4-dioxane (1 mL) and water (4 mL) and heated at 90° C. LCMS analysis of aliquot indicated complete conversion to product. The reaction mixture was neutralized with dil. HCl solution. The precipitate formed was collected by filtration, washed exhaustively with water and dried to afford 2-(2-methoxybenzamido)-5-(4-(pyridin-2-yl)piperazin-1-yl)benzoic acid as a yellow solid (15 mg, 70%). $^1$H NMR (400 MHz, Methanol-$d_4$) δ 8.70 (d, J=9.2 Hz, 1H), 8.11-8.01 (m, 2H), 7.97 (d, J=6.4 Hz, 1H), 7.70 (d, J=2.9 Hz, 1H), 7.54 (t, J=7.9 Hz, 1H), 7.45 (d, J=9.3 Hz, 1H), 7.30 (dd, J=9.3, 2.8 Hz, 1H), 7.18 (d, J=8.4 Hz, 1H), 7.08 (t, J=7.6 Hz, 1H), 7.02 (t, J=6.7 Hz, 1H), 4.05 (s, 3H), 3.89 (t, J=5.2 Hz, 4H), 3.44 (t, J=5.2 Hz, 4H). LRMS (ESI+ve): Calculated for $C_{24}H_{24}N_4O_4$, [M+H]=433.19, observed [M+H]=433.34. HRMS (ESI+ve): Calculated for $C_{24}H_{24}N_4O_4$, =432.1798, observed=432.1805.

Example 10

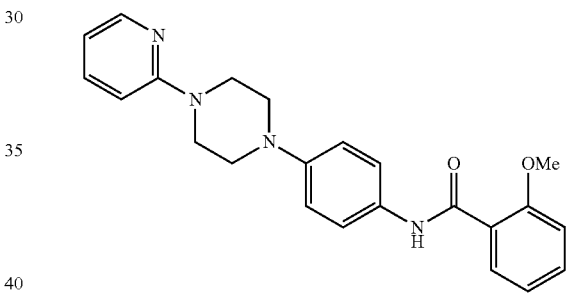

SBI-0814417 PRM0208-064-2. 2-methoxy-N-(4-(4-(pyridin-2-yl)piperazin-1-yl)phenyl)benzamide, as shown in the Formula above, was synthesized. A solution of 4-(4-(pyridin-2-yl)piperazin-1-yl)aniline (30 mg, 0.12 mmol), triethylamine (0.018 mL, 0.13 mmol), 2-methoxybenzoyl chloride (0.017 mL, 0.13 mmol) and a catalytic amount of DMAP in dichloromethane (1 mL) was stirred 1 hour at which time LCMS indicated the reaction was complete. Methanol (0.3 mL) was added to convert unreacted acid chloride to ester to simplify purification. The solvent was removed in vacuo and the residue partitioned with ethyl acetate and aqueous sodium bicarbonate. The organic phase was evaporated and the crude product purified on silica gel eluting with 5% methanol in dichloromethane (34 mg, 74%). $^1$H NMR (500 MHz, Chloroform-d) δ 9.70 (s, 1H), 8.32 (dd, J=7.9, 1.8 Hz, 1H), 8.25 (dd, J=5.0, 1.8 Hz, 1H), 7.67-7.57 (m, 2H), 7.52 (dddd, J=12.1, 8.3, 7.1, 1.9 Hz, 2H), 7.20-7.11 (m, 1H), 7.05 (d, J=8.3 Hz, 1H), 7.01 (d, J=8.9 Hz, 2H), 6.73 (d, J=8.6 Hz, 1H), 6.68 (dd, J=7.1, 4.9 Hz, 1H), 4.07 (s, 3H), 3.77-3.70 (m, 4H), 3.34-3.26 (m, 4H). HRMS (ESI+ve): Calculated for $C_{23}H_{24}N_4O_2$, =388.1899, observed=388.1922.

Example 11

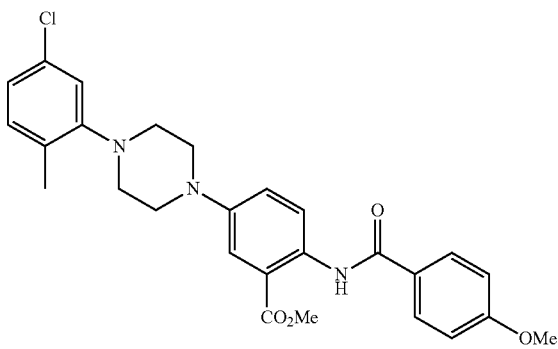 [SMILES: COC(=O)c1cc(N2CCN(c3cc(Cl)ccc3C)CC2)ccc1NC(=O)c1ccc(OC)cc1]

SBI-0801722 PRM0208-041-2. methyl 5-(4-(5-chloro-2-methylphenyl)piperazin-1-yl)-2-(4-methoxybenzamido)benzoate, as shown in the Formula above, was synthesized. A solution of methyl 2-amino-5-(4-(5-chloro-2-methylphenyl)piperazin-1-yl)benzoate (64 mg, 0.18 mmol), triethylamine (0.03 mL, 0.22 mmol), 4-methoxybenzoyl chloride (0.028 mL, 0.2 mmol) and a catalytic amount of DMAP in dichloromethane (1 mL) was stirred overnight. The reaction was diluted with dichloromethane, washed with water, and evaporated to a residue which was purified on silica gel eluting with 5-20% ethyl acetate in hexanes (73 mg, 82%). $^1$H NMR (500 MHz, Chloroform-d) δ 11.73 (s, 1H), 8.87 (d, J=9.0 Hz, 1H), 8.07-8.00 (m, 2H), 7.67 (d, J=2.8 Hz, 1H), 7.33-7.29 (m, 1H), 7.14 (d, J=8.1 Hz, 1H), 7.08-6.98 (m, 4H), 4.00 (d, J=1.3 Hz, 3H), 3.91 (d, J=1.4 Hz, 3H), 3.35 (dd, J=5.7, 3.7 Hz, 4H), 3.10 (t, J=4.8 Hz, 4H), 2.32 (s, 3H). LRMS (ESI+ve): Calculated for $C_{27}H_{28}ClN_3O_4$, [M+H]=494.18, observed [M+H]=494.04.

Example 12

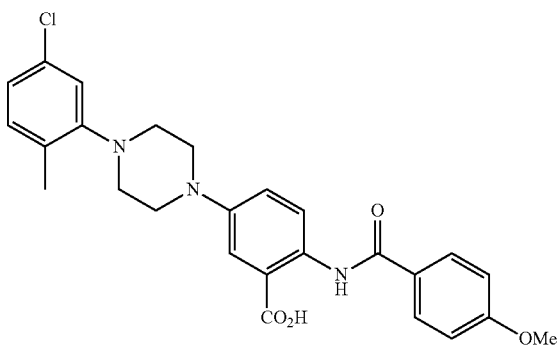 [SMILES: COc1ccc(C(=O)Nc2ccc(N3CCN(c4cc(Cl)ccc4C)CC3)cc2C(=O)O)cc1]

SBI-0754479 PRM0208-041-3. 5-(4-(5-chloro-2-methylphenyl)piperazin-1-yl)-2-(4-methoxybenzamido)benzoic acid, as shown in the Formula above, was synthesized. A solution of methyl 5-(4-(5-chloro-2-methylphenyl)piperazin-1-yl)-2-(4-methoxybenzamido)benzoate (70 mg, 0.14 mmol) in dioxane (1.5 mL) was stirred with 0.5 M aqueous lithium hydroxide solution (0.5 mL, 0.25 mmol) 3 hours. The reaction was concentrated then partitioned with ethyl acetate and aqueous ammonium chloride. The organic phase was evaporated and the crude product purified on silica gel eluting with 0-10% methanol in dichloromethane (30 mg, 44%). $^1$H NMR (500 MHz, Chloroform-d) δ 11.58 (s, 1H), 8.89 (d, J=9.1 Hz, 1H), 8.00 (d, J=8.2 Hz, 2H), 7.79-7.72 (m, 1H), 7.35 (d, J=9.2 Hz, 1H), 7.14 (d, J=8.0 Hz, 1H), 7.09-6.96 (m, 4H), 3.89 (s, 3H), 3.37 (s, 4H), 3.11 (s, 4H), 2.32 (d, J=2.4 Hz, 3H). LRMS (ESI+ve): Calculated for $C_{26}H_{26}ClN_3O_4$, [M+H]=480.17, observed [M+H]=480.24.

Example 13

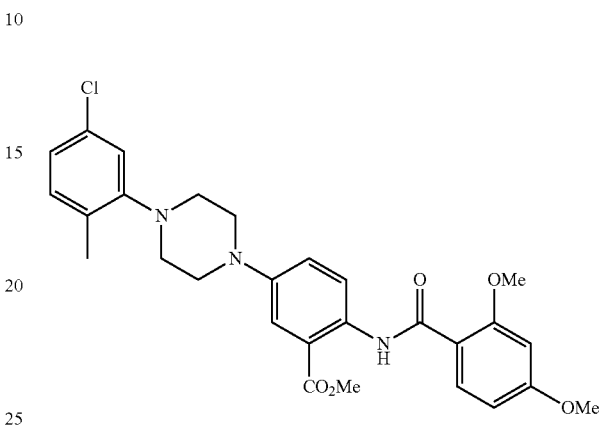

SBI-0801723 PRM0208-042-1. methyl 5-(4-(5-chloro-2-methylphenyl)piperazin-1-yl)-2-(2,4-dimethoxybenzamido)benzoate, as shown in the Formula above, was synthesized. A solution of methyl 2-amino-5-(4-(5-chloro-2-methylphenyl)piperazin-1-yl)benzoate (65 mg, 0.18 mmol), triethylamine (0.03 mL, 0.22 mmol), 2,4-dimethoxybenzoyl chloride (0.04 mL, 0.2 mmol) and a catalytic amount of DMAP in dichloromethane (1 mL) was stirred overnight. The reaction was diluted with dichloromethane, washed with water, and evaporated to a residue which was purified on silica gel eluting with 5-20% ethyl acetate in hexanes (60 mg, 63%). $^1$H NMR (400 MHz, Chloroform-d) δ 11.95 (s, 1H), 8.86 (d, J=9.2 Hz, 1H), 8.23 (d, J=8.8 Hz, 1H), 7.25 (m, 2H), 7.14 (d, J=8.0 Hz, 1H), 7.05 (d, J=2.1 Hz, 1H), 7.01 (dd, J=8.0, 2.1 Hz, 1H), 6.64 (dd, J=8.8, 2.4 Hz, 1H), 6.56 (d, J=2.3 Hz, 1H), 4.10 (s, 3H), 3.96 (s, 3H), 3.90 (s, 3H), 3.36 (s, 4H), 3.11 (s, 4H), 2.32 (s, 3H). LRMS (ESI+ve): Calculated for $C_{28}H_{30}ClN_3O_5$, [M+H]=524.20, observed [M+H]=524.31.

Example 14

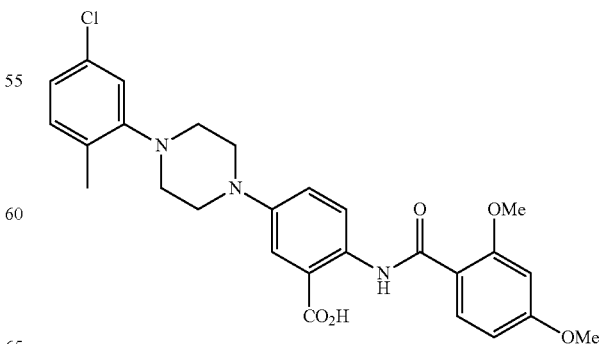

SBI-0801324 PRM0208-042-2. 5-(4-(5-chloro-2-methylphenyl)piperazin-1-yl)-2-(2,4-dimethoxybenzamido)benzoic acid, as shown in the Formula above, was synthesized. A soltion of methyl 5-(4-(5-chloro-2-methylphenyl)piperazin-1-yl)-2-(2,4-dimethoxybenzamido)benzoate (58 mg, 0.11 mmol) in dioxane (1.5 mL) was stirred with 0.5 M aqueous lithium hydroxide solution (0.5 mL, 0. 25 mmol) overnight. The reaction was concentrated then partitioned with ethyl acetate and aqueous ammonium chloride. The organic phase was evaporated and the crude product purified on silica gel eluting with 0-10% methanol in dichloromethane (40 mg, 71%). $^1$H NMR (500 MHz, DMSO-$d_6$) δ 12.2 (s, 1H), 8.69-8.63 (m, 1H), 7.95 (d, J=8.3 Hz, 1H), 7.56 (d, J=3.9 Hz, 1H), 7.23 (m, 2H), 7.08-7.00 (m, 2H), 6.68 (d, J=13.3 Hz, 2H), 3.99 (s, 3H), 3.85 (s, 3H), 3.28 (d, J=5.6 Hz, 4H), 3.02 (d, J=5.6 Hz, 4H), 2.26 (s, 3H). LRMS (ESI+ve): Calculated for $C_{27}H_{28}ClN_3O_5$, [M+H]=510.18, observed [M+H]=510.28.

Example 15

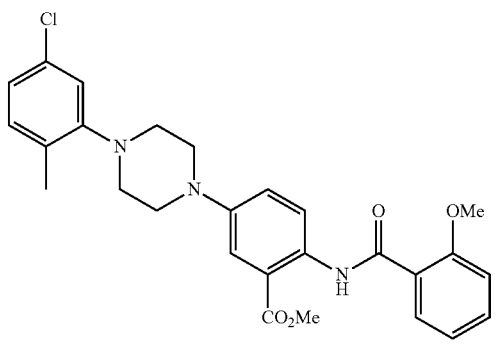 [SMILES: COC(=O)c1cc(N2CCN(c3cc(Cl)ccc3C)CC2)ccc1NC(=O)c1ccccc1OC]

SBI-0801724 PRM0208-042-3. methyl 5-(4-(5-chloro-2-methylphenyl)piperazin-1-yl)-2-(2-methoxybenzamido) benzoate, as shown in the Formula above, was synthesized. A solution of methyl 2-amino-5-(4-(5-chloro-2-methylphenyl)piperazin-1-yl)benzoate (65 mg, 0.18 mmol), triethylamine (0.03 mL, 0.22 mmol), 2-methoxybenzoyl chloride (0.02 mL, 0.22 mmol) and a catalytic amount of DMAP in dichloromethane (1 mL) was stirred overnight. The reaction was diluted with dichloromethane, washed with water, and evaporated to a residue which was purified on silica gel eluting with 5-20% ethyl acetate in hexanes (75 mg, 84%). $^1$H NMR (400 MHz, Chloroform-d) δ 12.02 (s, 1H), 8.87 (d, J=9.2 Hz, 1H), 8.23 (dd, J=7.8, 1.8 Hz, 1H), 7.66 (s, 1H), 7.50 (t, J=7.7 Hz, 1H), 7.12 (q, J=7.7 Hz, 2H), 7.08-6.95 (m, 4H), 4.11 (d, J=1.2 Hz, 3H), 3.96 (d, J=1.2 Hz, 3H), 3.36 (d, J=5.0 Hz, 4H), 3.11 (s, 4H), 2.32 (s, 3H). LRMS (ESI+ve): Calculated for $C_{27}H_{28}ClN_3O_4$, [M+H]=494.19, observed [M+H]=494.07.

Example 16

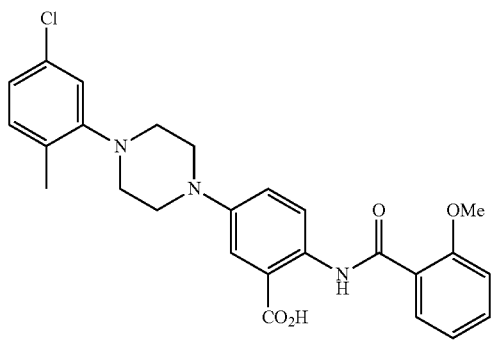 [SMILES: COc1ccccc1C(=O)Nc1ccc(N2CCN(c3cc(Cl)ccc3C)CC2)cc1C(=O)O]

SBI-0351221 PRM0208-042-4. 5-(4-(5-chloro-2-methylphenyl)piperazin-1-yl)-2-(2-methoxybenzamido)benzoic acid, as shown in the Formula above, was synthesized. A solution of methyl 5-(4-(5-chloro-2-methylphenyl)piperazin-1-yl)-2-(2-methoxybenzamido)benzoate (72 mg, 0.15 mmol) in dioxane (1.5 mL) was stirred with 0.5 M aqueous lithium hydroxide solution (0.5 mL, 0. 25 mmol) overnight. The reaction was concentrated then partitioned with ethyl acetate and aqueous ammonium chloride. The organic phase was evaporated and the crude product purified on silica gel eluting with 0-10% methanol in dichloromethane (40 mg, 57%). $^1$H NMR (500 MHz, Chloroform-d) δ 11.86 (s, 1H), 8.86 (d, J=9.6 Hz, 1H), 8.25 (d, J=7.8 Hz, 1H), 7.71 (s, 1H), 7.56-7.46 (m, 1H), 7.32 (d, J=9.5 Hz, 1H), 7.18-7.09 (m, 2H), 7.09-6.97 (m, 3H), 4.03 (d, J=3.0 Hz, 3H), 3.37 (d, J=5.3 Hz, 4H), 3.11 (d, J=5.4 Hz, 4H), 2.32 (t, J=2.3 Hz, 3H). LRMS (ESI+ve): Calculated for $C_{26}H_{26}ClN_3O_4$, [M+H]=480.17, observed [M+H]=480.26.

Example 17

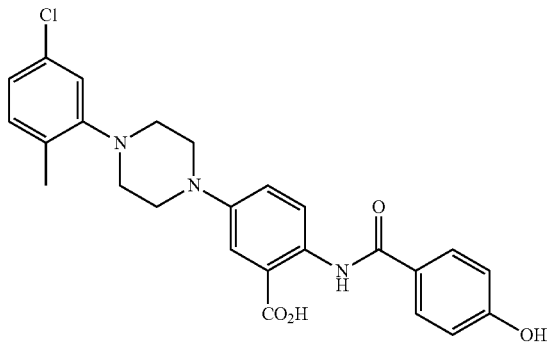 [SMILES: Cc1ccc(Cl)cc1N1CCN(c2ccc(NC(=O)c3ccc(O)cc3)c(C(=O)O)c2)CC1]

SBI-0801325 PRM0208-047-2. 5-(4-(5-chloro-2-methylphenyl)piperazin-1-yl)-2-(4-hydroxybenzamido)benzoic acid, as shown in the Formula above, was synthesized. A solution of methyl 2-amino-5-(4-(5-chloro-2-methylphenyl) piperazin-1-yl)benzoate (120 mg, 0.33 mmol), triethylamine (0.05 mL, 0.36 mmol), 4-hydroxybenzoyl chloride (80 mg, 0.51 mmol) and a catalytic amount of DMAP in dichloromethane (1 mL) was stirred overnight. The reaction was diluted with dichloromethane, washed with water, and evaporated to a residue which was purified on silica gel eluting with 0-5% methanol in dichloromethane. Yield=68 mg. (42%). The ester (23 mg, 0.048 mmol) in dioxane (2 mL) was hydrolyzed with 0.5 M aqueous lithium hydroxide solution (0.3 mL, 0.25 mmol) overnight. The reaction was concentrated then partitioned with ethyl acetate and aqueous ammonium chloride. The organic phase was evaporated and the crude product purified on silica gel eluting with 0-10% methanol in dichloromethane (4 mg, 18%). $^1$H NMR (500 MHz, Chloroform-d) δ 11.81 (s, 1H), 8.77 (d, J=9.2 Hz, 1H), 7.87 (d, J=8.3 Hz, 2H), 7.71 (d, J=3.0 Hz, 1H), 7.26 (dd, J=9.4, 3.0 Hz, 1H), 7.10 (d, J=8.0 Hz, 1H), 7.01 (d, J=2.2 Hz, 1H), 6.97 (dd, J=8.1, 2.0 Hz, 1H), 6.88 (d, J=8.3 Hz, 2H), 3.32 (t, J=4.7 Hz, 4H), 3.06 (t, J=4.8 Hz, 4H), 2.28 (s, 3H). LRMS (ESI+ve): Calculated for $C_{25}H_{24}ClN_3O_4$, [M+H]=466.15, observed [M+H]=466.24.

Example 18

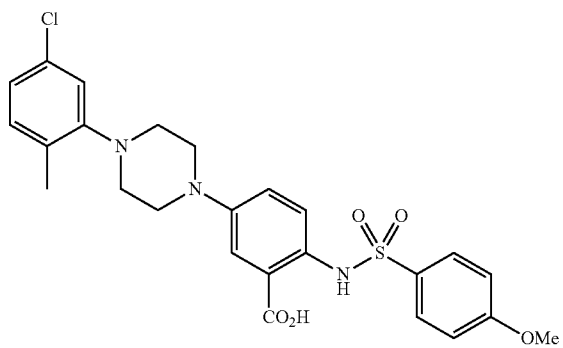 [SMILES: COc1ccc(S(=O)(=O)Nc2ccc(N3CCN(c4cc(Cl)ccc4C)CC3)cc2C(=O)O)cc1]

SBI-0801326 PRM0208-050-2. 5-(4-(5-chloro-2-methylphenyl)piperazin-1-yl)-2-(4-methoxyphenylsulfonamido)benzoic acid, as shown in the Formula above, was synthesized. A solution of methyl 2-amino-5-(4-(5-chloro-2-methylphenyl)piperazin-1-yl)benzoate (66 mg, 0.18 mmol), pyridine (0.03 mL, 0.37 mmol), and 4-methoxybenzene-1-sulfonyl chloride (42 mg, 0.2 mmol) in dichloromethane (1 mL) was stirred overnight. The reaction was concentrated, partitioned with ethyl acetate and water, evaporated and purified on silica gel eluting with dichloromethane. Yield=86 mg. (88%). The ester (84 mg, 0.16 mmol) in dioxane (5 mL) was hydrolyzed with 0.5 M aqueous lithium hydroxide solution (0.73 mL, 0.37 mmol) overnight. The reaction was concentrated then partitioned with ethyl acetate and aqueous ammonium chloride. The organic phase was evaporated and the crude product purified on silica gel eluting with 0-10% methanol in dichloromethane (8 mg, 10%). $^1$H NMR (500 MHz, Chloroform-d) δ 7.69 (d, J=8.9 Hz, 2H), 7.58 (d, J=3.0 Hz, 1H), 7.49 (d, J=8.9 Hz, 1H), 7.08 (d, J=8.6 Hz, 1H), 6.99 (dd, J=9.0, 2.9 Hz, 1H), 6.97-6.93 (m, 2H), 6.79 (d, J=8.9 Hz, 2H), 3.74 (s, 3H), 3.21 (dd, J=6.2, 3.5 Hz, 4H), 2.97 (t, J=4.9 Hz, 4H), 2.85 (s, 2H), 2.23 (s, 3H). LRMS (ESI+ve): Calculated for $C_{25}H_{26}ClN_3O_5S$, [M+H]=516.13, observed [M+H]=516.26.

Example 19

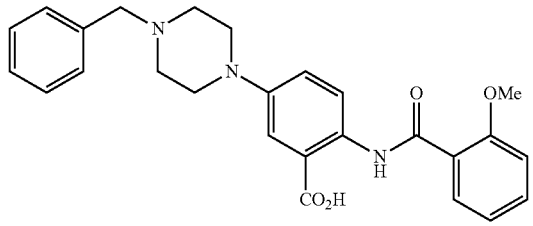 [SMILES: COc1ccccc1C(=O)Nc1ccc(N2CCN(Cc3ccccc3)CC2)cc1C(=O)O]

SBI-0801414 PRM0208-059-3. 5-(4-benzylpiperazin-1-yl)-2-(2-methoxybenzamido)benzoic acid, as shown in the Formula above, was synthesized. A solution of methyl 2-(2-methoxybenzamido)-5-(piperazin-1-yl)benzoate (35 mg, 0.094 mmol) in acetonitrile (1 mL) was treated with potassium carbonate (15 mg, 0.11 mmol) and benzyl chloride (0.014 mL, 0.12 mmol) then stirred at 60° C. overnight. The reaction was concentrated then partitioned with ethyl acetate and water. The organic phase was evaporated and the crude product purified on silica gel eluting with 40% ethyl acetate in hexanes. Yield=32 mg. (74%). The ester (35 mg, 0.076 mmol) in dioxane (1 mL) was hydrolyzed with 0.5 M aqueous lithium hydroxide solution (0.38 mL, 0.19 mmol) overnight. The reaction was concentrated then partitioned with ethyl acetate and aqueous ammonium chloride. The organic phase was evaporated and the crude product purified on silica gel eluting with 60% ethyl acetate in hexanes (29 mg, 85%). $^1$H NMR (500 MHz, Chloroform-d) δ 12.02 (s, 1H), 8.73 (d, J=9.1 Hz, 1H), 8.11 (d, J=7.8 Hz, 1H), 7.62 (d, J=3.0 Hz, 1H), 7.45 (d, J=7.1 Hz, 3H), 7.36 (dt, J=12.0, 7.0 Hz, 3H), 7.14 (dd, J=9.2, 2.9 Hz, 1H), 7.06 (t, J=7.6 Hz, 1H), 6.99 (d, J=8.3 Hz, 1H), 3.99 (s, 3H), 3.85 (s, 2H), 3.32 (d, J=4.7 Hz, 4H), 2.87 (s, 4H). HRMS (ESI+ve): Calculated for $C_{26}H_{27}N_3O_4$, =445.2002, observed=445.2009.

Example 20

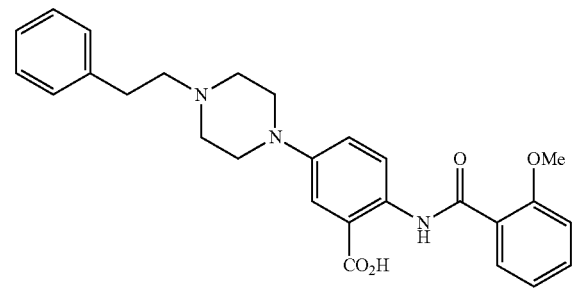 [SMILES: COc1ccccc1C(=O)Nc1ccc(N2CCN(CCc3ccccc3)CC2)cc1C(=O)O]

SBI-0801415 PRM0208-059-4. 2-(2-methoxybenzamido)-5-(4-phenethylpiperazin-1-yl)benzoic acid, as shown in the Formula above, was synthesized. A solution of methyl 2-(2-methoxybenzamido)-5-(piperazin-1-yl)benzoate (35 mg, 0.094 mmol) in acetonitrile (1 mL) was treated with potassium carbonate (15 mg, 0.11 mmol) and (2-bromoethyl)benzene (0.015 mL, 0.11 mmol) then stirred at 60° C. overnight. The reaction was concentrated then partitioned with ethyl acetate and water. The organic phase was evaporated and the crude product purified on silica gel eluting with 40% ethyl acetate in hexanes. Yield=18 mg. (40%). The ester (18 mg, 0.038 mmol) in dioxane (0.5 mL) was hydrolyzed with 0.5 M aqueous lithium hydroxide solution (0.19 mL, 0.095 mmol) overnight. The reaction was concentrated then partitioned with ethyl acetate and aqueous ammonium chloride. The organic phase was evaporated and the crude product purified on silica gel eluting with 60% ethyl acetate in hexanes (12 mg, 69%). $^1$H NMR (500 MHz, Methanol-d$_4$) δ 8.54 (d, J=9.0 Hz, 1H), 7.91 (d, J=8.6 Hz, 1H), 7.66 (d, J=3.0 Hz, 1H), 7.50 (t, J=8.9 Hz, 1H), 7.29 (dt, J=15.0, 7.5 Hz, 4H), 7.22 (d, J=7.2 Hz, 1H), 7.15 (d, J=8.4 Hz, 1H), 7.11-7.02 (m, 2H), 4.02 (s, 3H), 3.3 (m, 4H), 2.95-2.88 (m, 2H), 2.83 (s, 4H), 2.76 (d, J=9.0 Hz, 2H). LRMS (ESI+ve): Calculated for $C_{27}H_{31}N_3O_4$, [M+H]=460.53, observed [M+H]=460.58.

Example 21

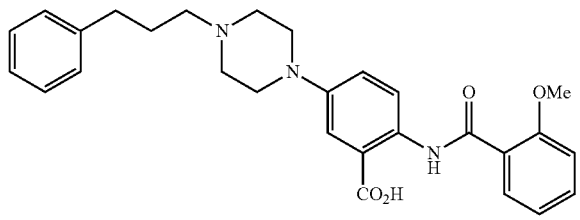 [SMILES: COc1ccccc1C(=O)Nc1ccc(N2CCN(CCCc3ccccc3)CC2)cc1C(=O)O]

SBI-0801416 PRM0208-059-5. 2-(2-methoxybenzamido)-5-(4-(3-phenylpropyl)piperazin-1-yl)benzoic acid, as shown in the Formula above, was synthesized. A solution of methyl 2-(2-methoxybenzamido)-5-(piperazin-1-yl)benzoate (35 mg, 0.094 mmol) in acetonitrile (1 mL) was treated with potassium carbonate (15 mg, 0.11 mmol) and (3-bromopropyl)benzene (0.016 mL, 0.11 mmol) then stirred at 60° C. overnight. The reaction was concentrated then partitioned with ethyl acetate and water. The organic phase was evaporated and the crude product purified on silica gel eluting with 40% ethyl acetate in hexanes (42 mg, 91%). $^1$H NMR (500 MHz, Chloroform-d) δ 11.97 (s, 1H), 8.82 (d, J=9.3 Hz, 1H), 8.23 (d, J=7.8 Hz, 1H), 7.57 (d, J=3.0 Hz, 1H), 7.49 (t, J=7.8 Hz, 1H), 7.35-7.29 (m, 2H), 7.26-7.17 (m, 4H), 7.10 (t, J=7.6 Hz, 1H), 7.04 (d, J=8.1 Hz, 1H), 4.10 (d, J=1.9 Hz, 3H), 3.94 (d, J=2.0 Hz, 3H), 3.28-3.17 (m, 4H), 2.70 (t, J=7.8 Hz, 2H), 2.64 (t, J=4.8 Hz, 4H), 2.47 (t, J=7.6 Hz, 2H), 1.90 (p, J=7.7 Hz, 2H). The ester (42 mg, 0.086 mmol) in dioxane (1 mL) was hydrolyzed with 0.5 M aqueous lithium hydroxide solution (0.43 mL, 0.22 mmol) overnight. The reaction was concentrated then partitioned with ethyl acetate and aqueous ammonium chloride. The organic phase was evaporated and the crude product purified on silica gel eluting with 60% ethyl acetate in hexanes (35 mg, 86%). $^1$H NMR (500 MHz, Chloroform-d) δ 12.14 (s, 1H), 8.70 (d, J=9.1 Hz, 1H), 8.08 (d, J=7.7 Hz, 1H), 7.63 (d, J=3.0 Hz, 1H), 7.47-7.40 (m, 1H), 7.28 (m, 2H), 7.18 (d, J=7.5 Hz, 3H), 7.13 (dd, J=9.1, 3.1 Hz, 1H), 7.09-7.01 (m, 1H), 6.98 (d, J=8.3 Hz, 1H), 3.97 (s, 3H), 3.38 (p, J=1.6 Hz, 4H), 2.88 (m, 4H), 2.68 (t, J=7.5 Hz, 2H), 2.57 (m, 2H), 2.02 (t, J=7.9 Hz, 2H). HRMS (ESI+ve): Calculated for $C_{28}H_{31}N_3O_4$, =473.2315, observed=473.2340.

Example 22

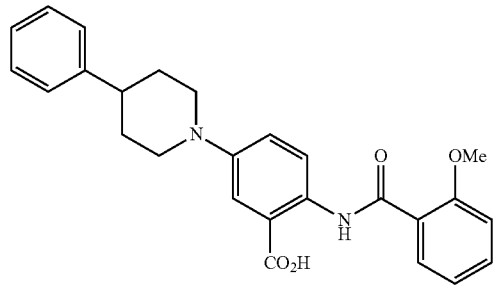

SBI-0801418 PRM0208-065-4. 2-(2-methoxybenzamido)-5-(4-phenylpiperidin-1-yl)benzoic acid, as shown in the Formula above, was synthesized. A solution of methyl 2-amino-5-(4-phenylpiperidin-1-yl)benzoate (40 mg, 0.13 mmol), triethylamine (0.02 mL, 0.14 mmol), 2-methoxybenzoyl chloride (0.02 mL, 0.15 mmol) and a catalytic amount of DMAP in dichloromethane (2 mL) was stirred overnight. The reaction was concentrated then partitioned with ethyl acetate and water. The organic phase was washed with aqueous potassium carbonate, evaporated, purified on silica gel eluting with 30% ethyl acetate in hexanes (54 mg, 94%). $^1$H NMR (500 MHz, Chloroform-d) δ 11.98 (s, 1H), 8.83 (d, J=9.2 Hz, 1H), 8.23 (dd, J=7.8, 1.7 Hz, 1H), 7.64 (d, J=3.0 Hz, 1H), 7.50 (td, J=7.8, 1.8 Hz, 1H), 7.36 (t, J=7.5 Hz, 2H), 7.30 (m, 2H), 7.28-7.23 (m, 2H), 7.11 (t, J=7.5 Hz, 1H), 7.05 (d, J=8.3 Hz, 1H), 4.11 (s, 3H), 3.95 (s, 3H), 3.86-3.77 (m, 2H), 2.86 (td, J=12.0, 2.9 Hz, 2H), 2.68 (tt, J=11.8, 4.1 Hz, 1H), 2.05-1.88 (m, 4H). The ester (54 mg, 0.12 mmol) in dioxane (6 mL) was hydrolyzed with 0.5 M aqueous lithium hydroxide solution (0.6 mL, 0.3 mmol) and water (0.5 mL) overnight. The reaction was concentrated then partitioned with ethyl acetate and aqueous ammonium chloride. The organic phase was evaporated and the crude product purified on silica gel eluting with 0-5% methanol in dichloromethane (45 mg, 86%). $^1$H NMR (500 MHz, Chloroform-d) δ 11.87 (s, 1H), 8.84 (d, J=9.2 Hz, 1H), 8.25 (dd, J=7.8, 1.7 Hz, 1H), 7.75 (d, J=3.0 Hz, 1H), 7.50 (td, J=7.8, 1.8 Hz, 1H), 7.38-7.31 (m, 3H), 7.30 (m, 2H), 7.27-7.23 (m, 1H), 7.12 (t, J=7.5 Hz, 1H), 7.00 (d, J=8.4 Hz, 1H), 4.00 (s, 3H), 3.83 (dd, J=12.5, 3.4 Hz, 2H), 2.88 (td, J=11.9, 3.3 Hz, 2H), 2.69 (tt, J=11.5, 4.3 Hz, 1H), 2.00 (qd, J=12.6, 3.6 Hz, 4H). HRMS (ESI+ve): Calculated for $C_{26}H_{26}N_2O_4$, =430.1893, observed=430.1932.

Example 23

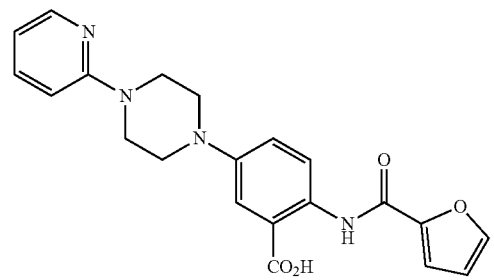 [SMILES: O=C(Nc1ccc(N2CCN(c3ccccn3)CC2)cc1C(=O)O)c1ccco1]

SBI-0801419 PRM0208-071-1. 2-(furan-2-carboxamido)-5-(4-(pyridin-2-yl)piperazin-1-yl)benzoic acid, as shown in the Formula above, was synthesized. A solution of furan-2-carboxylic acid (16.8 mg, 0.15 mmol), triethylamine (0.044 mL, 0.32 mmol), and HATU (58 mg, 0.15 mmol) in acetonitrile (1.5 mL) was stirred 20 minutes before methyl 2-amino-5-(4-(pyridin-2-yl)piperazin-1-yl)benzoate (32 mg, 0.10 mmol) was added. After stirring overnight, the reaction was concentrated, the residue partitioned with ethyl acetate and aqueous sodium bicarbonate, then the organic phase was evaporated. The residue was then dissolved in dichloromethane and captured on a 1 g. SCX-2 SPE column. The column was flushed with dichloromethane and ethyl acetate prior to eluting the desired product with 10% triethylamine in ethyl acetate. The solvent was evaporated to a residue which was used without further purification (33 mg, 79%). $^1$H NMR (500 MHz, Chloroform-d) δ 11.77 (s, 1H), 8.80 (d, J=9.1 Hz, 1H), 8.25 (dd, J=5.0, 1.8 Hz, 1H), 7.66 (d, J=2.9 Hz, 1H), 7.62 (d, J=1.5 Hz, 1H), 7.54 (ddd, J=8.7, 7.2, 1.9 Hz, 1H), 7.27 (d, J=3.1 Hz, 1H), 7.25 (d, J=3.6 Hz, 1H), 6.74 (d, J=8.6 Hz, 1H), 6.69 (dd, J=7.1, 4.9 Hz, 1H), 6.57 (dd, J=3.4, 1.7 Hz, 1H), 4.01 (s, 3H), 3.81-3.68 (m, 4H), 3.40-3.29 (m, 4H). The ester (33 mg, 0.08 mmol) in dioxane (3 mL) was hydrolyzed with 0.5 M aqueous lithium hydroxide solution (0.35 mL, 0.18 mmol) and water (0.3 mL) overnight. The reaction was concentrated then partitioned with ethyl acetate, acetonitrile, and aqueous ammonium chloride. The organic phase was evaporated and the crude product purified on reverse phase HPLC (20 mg, 63%). $^1$H NMR (500 MHz, DMSO-d$_6$) δ 11.84 (s, 1H), 8.55 (d, J=9.2 Hz, 1H), 8.12 (d, J=5.2 Hz, 1H), 7.96 (d, J=1.6 Hz, 1H), 7.68 (s, 1H), 7.58 (d, J=3.0 Hz, 1H), 7.38 (dd, J=9.2, 3.0 Hz, 1H), 7.23 (d, J=3.5 Hz, 1H), 7.03 (s, 1H), 6.73 (dd, J=3.5, 1.7 Hz, 2jH), 3.70 (t, J=5.0 Hz, 4H), 3.28 (d, J=5.2 Hz, 4H). HRMS (ESI+ve): Calculated for $C_{21}H_{20}N_4O_4$, =392.1485, observed=392.1492.

Example 24

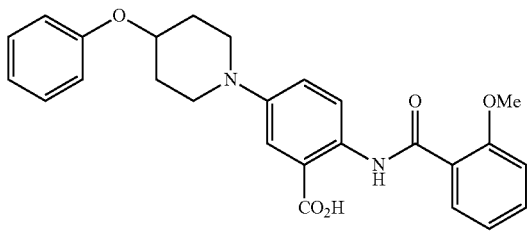 [SMILES: COc1ccccc1C(=O)Nc1ccc(N2CCC(Oc3ccccc3)CC2)cc1C(=O)O]

SBI-0801420 PRM0208-073-5. 2-(2-methoxybenzamido)-5-(4-phenoxypiperidin-1-yl)benzoic acid, as shown in the Formula above, was synthesized. A solution of methyl 2-amino-5-(4-phenoxypiperidin-1-yl)benzoate (57 mg, 0.18 mmol), triethylamine (0.05 mL, 0.36 mmol), 2-methoxybenzoyl chloride (0.025 mL, 0.18 mmol), and a catalytic amount of DMAP in dichloromethane (2 mL) was stirred overnight. The reaction was diluted with dichloromethane, washed with water, and evaporated to a residue which was purified on silica gel eluting with 20% ethyl acetate in hexanes (32 mg, 40%). $^1$H NMR (500 MHz, Chloroform-d) δ 11.98 (s, 1H), 8.82 (d, J=9.2 Hz, 1H), 8.23 (dt, J=7.8, 1.4 Hz, 1H), 7.62 (d, J=2.9 Hz, 1H), 7.51-7.46 (m, 1H), 7.31 (d, J=7.9 Hz, 2H), 7.24 (dd, J=9.2, 3.0 Hz, 1H), 7.11 (t, J=7.5 Hz, 2H), 7.05 (d, J=8.3 Hz, 1H), 7.01-6.91 (m, 3H), 4.51 (tt, J=7.4, 3.7 Hz, 1H), 4.11 (d, J=1.0 Hz, 3H), 3.94 (d, J=1.0 Hz, 3H), 3.52 (ddd, J=11.6, 7.3, 3.6 Hz, 2H), 3.14 (ddd, J=12.0, 8.0, 3.5 Hz, 2H), 2.15 (ddd, J=11.4, 7.9, 3.7 Hz, 2H), 2.00 (dtd, J=12.0, 7.6, 3.6 Hz, 2H). The ester (32 mg, 0.069 mmol) in dioxane (2 mL) was hydrolyzed with 0.5 M aqueous lithium hydroxide solution (0.2 mL, 0.1 mmol) overnight. The reaction was concentrated then partitioned with ethyl acetate and aqueous ammonium chloride. The organic phase was evaporated and the crude product purified on silica gel eluting with 0-3% methanol in dichloromethane (8 mg, 26%). $^1$H NMR (500 MHz, DMSO-d$_6$) δ 12.23 (s, 1H), 8.64 (d, J=9.2 Hz, 1H), 7.99-7.92 (m, 1H), 7.58-7.50 (m, 2H), 7.29 (dd, J=8.6, 7.3 Hz, 2H), 7.25 (dd, J=9.2, 2.9 Hz, 1H), 7.20 (d, J=8.4 Hz, 1H), 7.09 (t, J=7.5 Hz, 1H), 6.99 (d, J=8.1 Hz, 2H), 6.93 (t, J=7.3 Hz, 1H), 4.57 (dt, J=8.3, 4.3 Hz, 1H), 3.98 (s, 3H), 3.58-3.45 (m, 2H), 3.05 (ddd, J=12.5, 9.1, 3.2 Hz, 2H), 2.12-2.00 (m, 2H), 1.75 (dtd, J=12.6, 8.7, 3.6 Hz, 2H). HRMS (ESI+ve): Calculated for $C_{26}H_{26}N_2O_5$, =446.1842, observed=446.1876.

Example 25

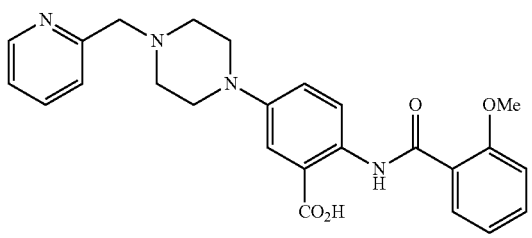 [SMILES: COc1ccccc1C(=O)Nc1ccc(N2CCN(Cc3ccccn3)CC2)cc1C(=O)O]

SBI-08014421 PRM0208-075-2. 2-(2-methoxybenzamido)-5-(4-(pyridin-2-ylmethyl)piperazin-1-yl)benzoic acid, as shown in the Formula above, was synthesized. A solution of methyl 2-(2-methoxybenzamido)-5-(piperazin-1-yl)benzoate (32 mg, 0.087 mmol) in acetonitrile (2 mL) was treated with potassium carbonate (30 mg, 0.22 mmol) and 2-(bromomethyl)pyridine hydrobromide (23 mg, 0.091 mmol) then stirred at 60° C. overnight. The reaction was concentrated then partitioned with ethyl acetate and water. The organic phase was evaporated and the crude product was used without further purification (36 mg, 90%). $^1$H NMR (500 MHz, Chloroform-d) δ 11.96 (s, 1H), 8.78 (d, J=9.3 Hz, 1H), 8.58 (d, J=4.8 Hz, 1H), 8.19 (dd, J=7.8, 1.9 Hz, 1H), 7.70 (td, J=7.6, 1.8 Hz, 1H), 7.56 (d, J=3.0 Hz, 1H), 7.48 (dq, J=7.4, 3.7, 2.9 Hz, 2H), 7.20 (ddd, J=12.2, 8.3, 4.0 Hz, 2H), 7.09 (t, J=7.6 Hz, 1H), 7.03 (d, J=8.3 Hz, 1H), 4.08 (s, 3H), 3.92 (s, 3H), 3.75 (s, 2H), 3.24 (t, J=4.9 Hz, 4H), 2.71 (t, J=4.8 Hz, 4H). The ester (36 mg, 0.078 mmol) in dioxane (1.2 mL) was hydrolyzed with 0.5 M aqueous lithium hydroxide solution (0.33 mL, 0.17 mmol) overnight. The reaction was concentrated then partitioned with ethyl acetate and aqueous ammonium chloride. The organic phase was evaporated and the crude product purified on reverse phase HPLC (13.5 mg, 39%). $^1$H NMR (500 MHz, Chloroform-d) δ 12.03 (s, 1H), 8.75 (d, J=9.2 Hz, 1H), 8.59 (d, J=4.9 Hz, 1H), 8.12 (d, J=7.8 Hz, 1H), 8.06 (s, 1H), 7.74 (t, J=7.7 Hz, 1H), 7.62 (d, J=2.8 Hz, 1H), 7.55 (d, J=7.8 Hz, 1H), 7.46 (t, J=7.9 Hz, 1H), 7.27 (d, J=8.1 Hz, 1H), 7.16 (dd, J=9.2, 2.9 Hz, 1H), 7.06 (t, J=7.6 Hz, 1H), 6.99 (d, J=8.3 Hz, 1H), 3.99 (s, 3H), 3.96 (s, 2H), 3.30 (t, J=4.9 Hz, 4H), 2.94 (t, J=4.7 Hz, 4H). HRMS (ESI+ve): Calculated for $C_{25}H_{26}N_4O_4$, =446.1954, observed=446.1956.

Example 26

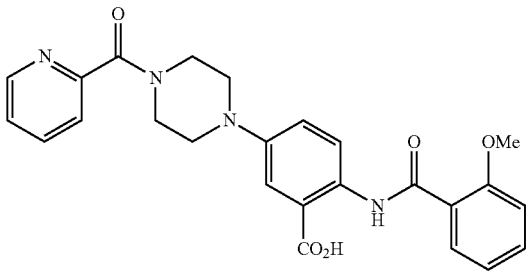 [SMILES: COc1ccccc1C(=O)Nc1ccc(N2CCN(C(=O)c3ccccn3)CC2)cc1C(=O)O]

SBI-08014424 PRM0208-092-2. 2-(2-methoxybenzamido)-5-(4-picolinoylpiperazin-1-yl)benzoic acid, as shown in the Formula above, was synthesized. A solution of picolinic acid (22 mg, 0.18 mmol), triethylamine (0.05 mL, 0.36 mmol), and HATU (68 mg, 0.18 mmol) in acetonitrile (2 mL) was stirred 30 minutes prior to addition of methyl 2-amino-5-(4-(pyridin-2-yl)piperazin-1-yl)benzoate (50 mg, 0.14 mmol). After stirring overnight, the reaction was condensed and the residue partitioned with ethyl acetate and water. The organic phase was evaporated and the residue was purified on silica gel eluting with 0-5% methanol in dichloromethane (44 mg, 69%). $^1$H NMR (500 MHz, Chloroform-d) δ 12.01 (s, 1H), 8.85 (dd, J=9.1, 1.7 Hz, 1H), 8.64 (d, J=4.8 Hz, 1H), 8.22 (d, J=7.9 Hz, 1H), 7.85 (t, J=7.8 Hz, 1H), 7.73 (d, J=7.8 Hz, 1H), 7.60 (d, J=2.6 Hz, 1H), 7.50 (t, J=7.9 Hz, 1H), 7.39 (t, J=6.4 Hz, 1H), 7.25-7.18 (m, 1H), 7.11 (t, J=7.6 Hz, 1H), 7.05 (d, J=8.2 Hz, 1H), 4.11 (d, J=1.8 Hz, 3H), 4.02 (t, J=4.9 Hz, 2H), 3.94 (d, J=1.7 Hz, 3H), 3.84 (t, J=4.8 Hz, 2H), 3.32 (t, J=5.0 Hz, 2H), 3.22 (d, J=5.0 Hz, 2H). The ester (38 mg, 0.08 mmol) in dioxane (1.5 mL) was hydrolyzed with 0.5 M aqueous lithium hydroxide solution (0.27 mL, 0.14 mmol) overnight. The reaction was concentrated then partitioned with ethyl acetate and aqueous ammonium chloride. The organic phase was evaporated and the crude product purified on silica gel eluting with 0-3% methanol in dichloromethane (7 mg, 19%). $^1$H NMR (500 MHz, Chloroform-d) δ 12.02 (s, 1H), 8.81 (d, J=9.1 Hz, 1H), 8.71 (s, 1H), 8.18 (d, J=7.7 Hz, 1H), 7.88 (s, 1H), 7.71 (d, J=7.7 Hz, 1H), 7.62 (s, 1H), 7.53-7.36 (m, 2H), 7.19 (s, 1H), 7.09 (d, J=7.9 Hz, 1H), 7.03-6.92 (m, 1H), 3.99 (s, 5H), 3.73 (s, 2H), 3.28 (s, 2H), 3.19 (s, 2H). HRMS (ESI+ve): Calculated for $C_{25}H_{24}N_4O_5$, =460.1747, observed=460.1773.

Example 27

For reference, the following structures are noted:

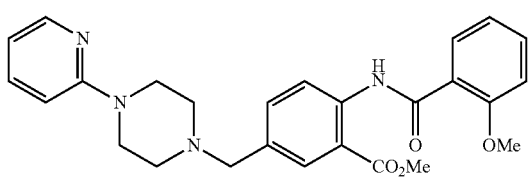

SBI-08014422 PRM0208-090-1

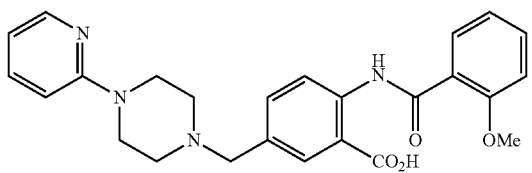

SBI-08014423 PRM0208-090-2

The following reaction pathway was employed.

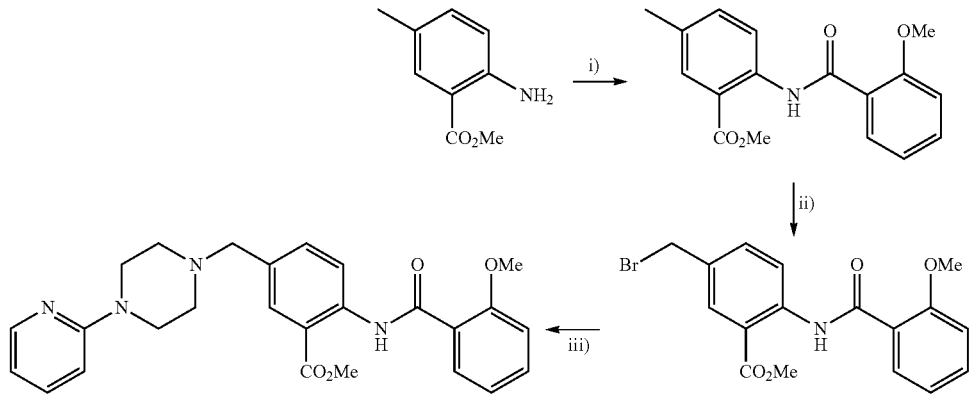

Reagents: i) 2-methoxy benzoylchloride, DMAP, Et$_3$N, DCM, ii) N-bromosuccinimide, AIBN, CCl$_4$; iii) 1-(pyridin-2-yl)piperazine, MeCN. 60° C., gave the methylester SBI-08014422 PRM0208-090-1, then LiOH, H$_2$O, dioxane gave the SBI-08014423 PRM0208-090-2 carboxylic acid form after acidification with aqueous NH$_4$Cl.

PRM0208-089-1. Methyl 2-(2-methoxybenzamido)-5-methylbenzoate was synthesized. A solution of methyl 2-amino-5-methylbenzoate (330 mg, 2.0 mmol), triethylamine (0.30 mL, 2.15 mmol), and 2-methoxybenzoyl chloride (0.27 mL, 2.0 mmol) and a catalytic amount of DMAP in dichloromethane (20 mL) was stirred overnight. The reaction was diluted with dichloromethane, washed with water and aqueous sodium bicarbonate, then evaporated to a residue which was purified on silica gel eluting with 15-30% ethyl acetate in hexanes (510 mg, 85%). $^1$H NMR (500 MHz, Chloroform-d) δ 12.11 (s, 1H), 8.84 (d, J=8.6 Hz, 1H), 8.22 (d, J=7.8 Hz, 1H), 7.85 (d, J=2.4 Hz, 1H), 7.53-7.45 (m, 1H), 7.40 (dd, J=8.7, 2.1 Hz, 1H), 7.10 (t, J=7.5 Hz, 1H), 7.04 (d, J=8.2 Hz, 1H), 4.10 (d, J=1.6 Hz, 3H), 3.95-3.90 (m, 3H), 2.37 (s, 3H). LRMS (ESI+ve): Calculated for C$_{17}$H$_{17}$NO$_4$, [M+H]=300.12, observed [M+H]=300.37.

Example 28

PRM0208-089-2. Methyl 5-(bromomethyl)-2-(2-methoxybenzamido)benzoate was synthesized. A mixture of methyl 2-(2-methoxybenzamido)-5-methylbenzoate (139 mg, 0.46 mmol), NBS (92 mg, 0.51 mmol), and a catalytic amount of AIBN in carbon tetrachloride (5 mL) was stirred at reflux 3 hours. The reaction was partitioned with dichloromethane and water, then the organic phase evaporated and purified on silica gel eluting with 15% ethyl acetate in hexanes (88 mg, 50%). $^1$H NMR (500 MHz, Chloroform-d) δ 8.97 (dd, J=8.9, 1.5 Hz, 1H), 8.21 (d, J=7.8 Hz, 1H), 8.10 (d, J=2.0 Hz, 1H), 7.65-7.58 (m, 1H), 7.52 (t, J=7.8 Hz, 1H), 7.15-7.09 (m, 1H), 7.06 (d, J=8.4 Hz, 1H), 4.53 (d, J=1.5 Hz, 2H), 4.10 (d, J=1.5 Hz, 4H), 3.96 (d, J=1.6 Hz, 3H). LRMS (ESI+ve): Calculated for C$_{17}$H$_{16}$BrNO$_4$, [M+H]=378.03, observed [M+H]=378.36.

Example 29

PRM0208-090-1. Methyl 2-(2-methoxybenzamido)-5-((4-(pyridin-2-yl)piperazin-1-yl)methyl)benzoate was synthesized. A solution of methyl 5-(bromomethyl)-2-(2-methoxybenzamido)benzoate (44 mg, 0.12 mmol) and 1-(pyridin-2-yl)piperazine (0.019 mL, 0.13 mmol) in acetonitrile (2 mL) was stirred at 60° C. 1 hour before the solvent was removed in vacuo. The residue was partitioned with ethyl acetate and saturated aqueous potassium carbonate, the organic phase condensed, and the residue purified on silica gel eluting with 0-5% methanol in dichloromethane (32 mg, 60%). $^1$H NMR (500 MHz, Chloroform-d) δ 12.18 (s, 1H), 8.91 (d, J=8.6 Hz, 1H), 8.21 (t, J=6.2 Hz, 2H), 8.02 (s, 1H), 7.63-7.56 (m, 1H), 7.54-7.45 (m, 2H), 7.11 (t, J=7.5 Hz, 1H), 7.06 (d, J=8.3 Hz, 1H), 6.67-6.61 (m, 2H), 4.11 (d, J=1.4 Hz, 3H), 3.95 (d, J=1.4 Hz, 3H), 3.58 (d, J=7.1 Hz, 6H), 2.59 (t, J=5.1 Hz, 4H). LRMS (ESI+ve): Calculated for C$_{26}$H$_{28}$N$_4$O$_4$, [M+H]=461.22, observed [M+H]=461.56.

Example 30

PRM0208-090-2. 2-(2-Methoxybenzamido)-5-((4-(pyridin-2-yl)piperazin-1-yl)methyl)benzoic acid was synthesized. A solution of methyl 2-(2-methoxybenzamido)-5-((4-(pyridin-2-yl)piperazin-1-yl)methyl)benzoate (28 mg, 0.061 mmol) in dioxane (1 mL) was hydrolyzed with 0.5 M aqueous lithium hydroxide solution (0.24 mL, 0.12 mmol) overnight. The reaction was concentrated then partitioned with ethyl acetate, acetonitrile, and aqueous ammonium chloride. The organic phase was evaporated and the crude product purified on silica gel eluting with 5% methanol in dichloromethane (11.5 mg, 42%). $^1$H NMR (500 MHz, Chloroform-d) δ 12.85 (s, 1H), 8.85 (d, J=8.4 Hz, 1H), 8.55 (s, 1H), 8.17 (dd, J=5.0, 1.9 Hz, 1H), 8.05 (d, J=7.6 Hz, 1H), 7.50 (td, J=7.0, 3.5 Hz, 1H), 7.43 (t, J=7.8 Hz, 1H), 7.31 (d, J=8.5 Hz, 1H), 7.03 (t, J=7.5 Hz, 1H), 6.93 (d, J=8.3 Hz, 1H), 6.73-6.61 (m, 2H), 3.88 (d, J=6.2 Hz, 5H), 2.99 (s, 4H), 2.48 (s, 4H). HRMS (ESI+ve): Calculated for C$_{25}$H$_{26}$N$_4$O$_4$, =446.1954, observed=446.1976.

Example 31

The following reaction pathway was employed.

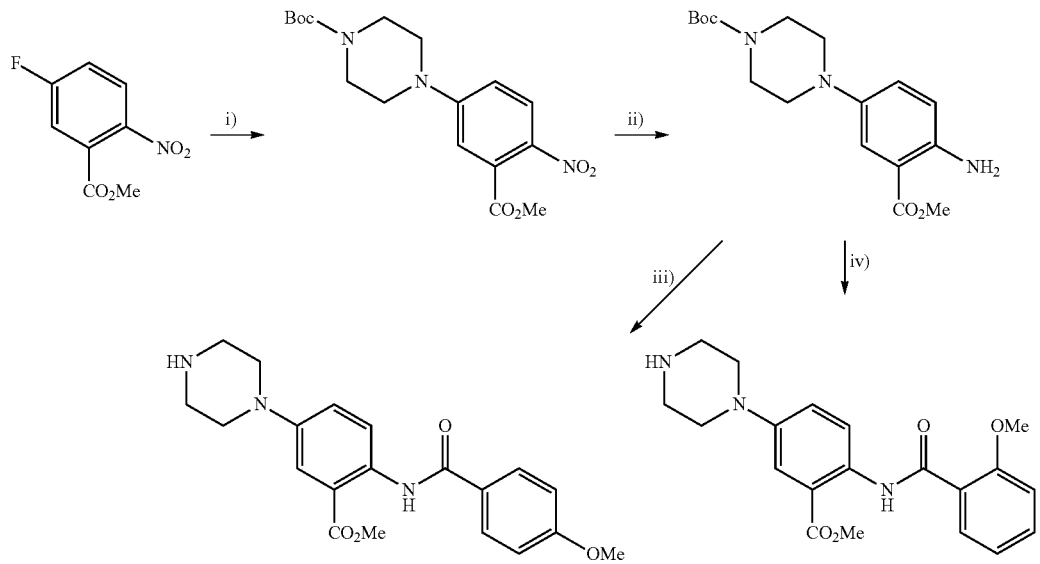

Reagents: i) 1-Boc-piperazine, Et$_3$N, 1,4-dioxane, reflux; ii) Zn, HOAc; iii) 4-methoxybenzoyl chloride, Et$_3$N, DMPA, 1,4-dioxane then TFA; iv) 2-methyoxybenzoyl chlroide, Et$_3$N, DMAP, 1,4-dioxane then TFA.

PRM0208-32-1. Tert-butyl 4-(3-(methoxycarbonyl)-4-nitrophenyl)piperazine-1-carboxylate was synthesized. A solution of methyl 5-fluoro-2-nitrobenzoate (1.09 g, 5.48 mmol), tert-butyl piperazine-1-carboxylate (1.02 g, 5.48 mmol), and triethylamine (0.78 mL, 5.6 mmol) in dioxane (30 mL) was stirred at reflux overnight. The solvent was removed in vacuo and the residue partitioned with ethyl acetate and water. The organic phase was evaporated to an oil which was used without further purification (1.96 g, 98%). $^1$H NMR (500 MHz, Chloroform-d) δ 8.05 (d, J=9.9 Hz, 1H), 6.90-6.82 (m, 2H), 3.95 (s, 3H), 3.62 (dd, J=6.6, 4.0 Hz, 4H), 3.45

(dd, J=6.5, 4.1 Hz, 4H), 1.51 (s, 9H). LRMS (ESI+ve): Calculated for C₁₇H₂₃N₃O₆, [M+H]=366.17, observed [M+H]=366.31.

Example 32

PRM0208-32-3. Tert-butyl 4-(4-amino-3-(methoxycarbonyl)phenyl)piperazine-1-carboxylate was synthesized. A solution of tert-butyl 4-(3-(methoxycarbonyl)-4-nitrophenyl)piperazine-1-carboxylate (1.6 g, 4.38 mmol) in acetic acid (30 mL) was treated with powdered zinc (1.0 g, 15.3 mmol) portionwise over 10 minutes to control the exothermic reaction. The mixture was let stir overnight, filtered, and evaporated to provide an oil which was partitioned with ethyl acetate and aqueous potassium carbonate. The organic phase was evaporated and the crude product purified on silica gel eluting with 50% ethyl acetate in hexanes (1.1 g, 75%). ¹H NMR (500 MHz, Chloroform-d) δ 7.57-7.44 (m, 1H), 7.14 (s, 1H), 6.68 (d, J=8.8 Hz, 1H), 3.89 (s, 3H), 3.65 (s, 4H), 3.02 (s, 4H), 1.50 (s, 9H). LRMS (ESI+ve): Calculated for C₁₇H₂₅N₃O₄, [M+H]=336.19, observed [M+H]=336.21.

Example 33

PRM0208-34-1, PRM0208-34-2. Methyl 2-(4-methoxybenzamido)-5-(piperazin-1-yl)benzoate was synthesized. A solution of tert-butyl 4-(4-amino-3-(methoxycarbonyl)phenyl)piperazine-1-carboxylate (410 mg, 1.22 mmol), 4-methoxybenzoyl chloride (0.19 mL, 1.38 mmol), triethylamine (0.21 mL, 1.51 mmol), and catalytic DMAP in dioxane (10 mL) was stirred for 30-60 minutes at which time LCMS indicated the limiting reagent was consumed. The solvent was removed in vacuo and the residue was purified on silica gel eluting with 20-50% ethyl acetate in hexanes. Yield=400 mg. (70%). ¹H NMR (500 MHz, Chloroform-d) δ 11.73 (s, 1H), 8.86 (d, J=9.2 Hz, 1H), 8.02 (d, J=8.8 Hz, 2H), 7.65 (s, 1H), 7.26 (d, J=10.0 Hz, 1H), 7.03 (d, J=8.9 Hz, 2H), 3.98 (s, 3H), 3.90 (s, 3H), 3.64 (t, J=5.1 Hz, 4H), 3.15 (t, J=5.0 Hz, 4H), 1.51 (s, 9H). LRMS (ESI+ve): Calculated for C₂₅H₃₁N₃O₆, [M+H]=470.23, observed [M+H]=470.07. The Boc protecting group was removed with 20% trifluoroacetic acid in dichloromethane at ambient temperature over 2.5 hours. The solvent was removed in vacuo and the residue partitioned with ethyl acetate and aqueous sodium bicarbonate. The precipitated product was collected by filtration and was used without further purification (300 mg, 95%). ¹H NMR (500 MHz, DMSO-d₆) δ 11.17 (s, 1H), 8.36 (d, J=9.1 Hz, 1H), 7.91 (d, J=8.6 Hz, 2H), 7.44 (d, J=3.0 Hz, 1H), 7.30 (dd, J=9.1, 3.1 Hz, 1H), 7.12 (d, J=8.6 Hz, 2H), 3.87 (s, 3H), 3.85 (s, 3H), 3.04 (t, J=4.9 Hz, 4H), 2.84 (t, J=4.9 Hz, 4H). LRMS (ESI+ve): Calculated for C₂₀H₂₃N₃O₄, [M+H]=370.18, observed [M+H]=370.57.

Example 34

PRM0208-59-1, PRM0208-59-2. Methyl 2-(2-methoxybenzamido)-5-(piperazin-1-yl)benzoate was synthesized. A solution of tert-butyl 4-(4-amino-3-(methoxycarbonyl)phenyl)piperazine-1-carboxylate (290 mg, 0.86 mmol), 2-methoxybenzoyl chloride (0.12 mL, 0.88 mmol), triethylamine (0.14 mL, 1.0 mmol), and catalytic DMAP in dioxane (10 mL) was stirred overnight. The solvent was removed in vacuo and the residue was purified on silica gel eluting with 30-60% ethyl acetate in hexanes (362 mg, 89%). ¹H NMR (500 MHz, Chloroform-d) δ 12.00 (s, 1H), 8.84 (d, J=9.2 Hz, 1H), 8.22 (dd, J=7.8, 1.8 Hz, 1H), 7.59 (s, 1H), 7.53-7.46 (m, 1H), 7.21 (d, J=9.7 Hz, 1H), 7.11 (t, J=7.6 Hz, 1H), 7.05 (d, J=8.4 Hz, 1H), 4.11 (s, 3H), 3.94 (s, 3H), 3.64 (d, J=5.0 Hz, 4H), 3.19-3.09 (m, 4H), 1.51 (s, 9H). LRMS (ESI+ve): Calculated for C₂₅H₃₁N₃O₆, [M+H]=470.23, observed [M+H]=470.03. The Boc protecting group was removed with 20% trifluoroacetic acid in dichloromethane at ambient temperature over 2.5 hours. The solvent was removed in vacuo and the residue partitioned with ethyl acetate and aqueous potassium carbonate. The organic phase was evaporated to provide a yellow solid which was used without further purification (270 mg, 95%). ¹H NMR (500 MHz, Chloroform-d) δ 12.00 (s, 1H), 8.82 (d, J=9.2 Hz, 1H), 8.21 (dd, J=7.8, 2.0 Hz, 1H), 7.56 (d, J=3.0 Hz, 1H), 7.49 (ddd, J=8.6, 7.2, 1.7 Hz, 1H), 7.17 (dd, J=9.3, 3.0 Hz, 1H), 7.10 (td, J=7.6, 1.0 Hz, 1H), 7.06-7.00 (m, 1H), 4.66 (s, 1H), 4.09 (d, J=1.2 Hz, 3H), 3.93 (d, J=1.9 Hz, 3H), 3.28-3.21 (m, 4H), 3.22-3.13 (m, 4H). LRMS (ESI+ve): Calculated for C₂₀H₂₃N₃O₄, [M+H]=370.18, observed [M+H]=370.27.

Example 35

The following reaction pathway was employed.

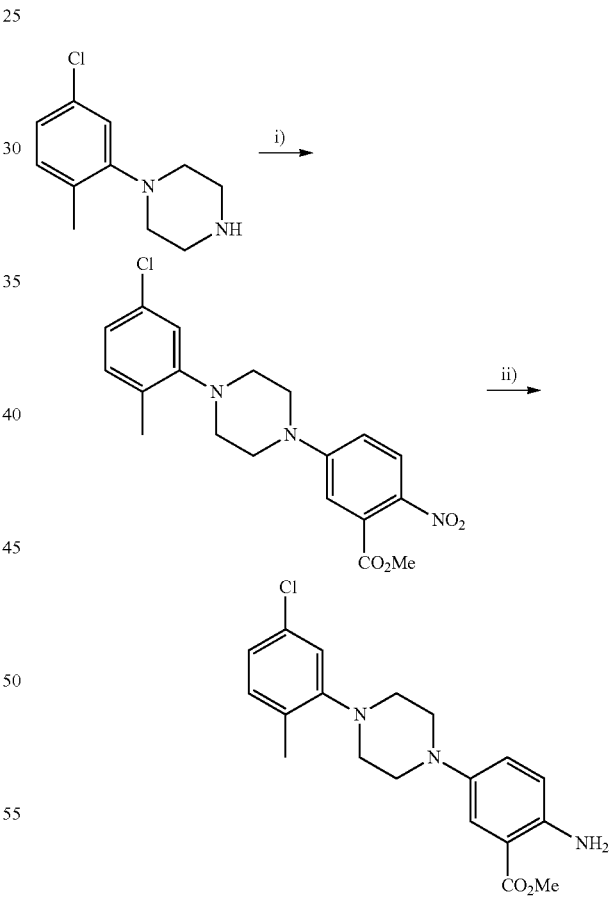

Reagents: i) methyl 2-nitro-5-fluoro benzoate, Et₃N, 1,4-dioxane, reflux; ii) Zn, HOAc.

PRM0208-48-1. Methyl 5-(4-(5-chloro-2-methylphenyl)piperazin-1-yl)-2-nitrobenzoate was synthesized. A solution of 1-(5-chloro-2-methylphenyl)piperazine (1.19 g, 5.65 mmol), methyl 5-fluoro-2-nitrobenzoate (1.12 g, 5.65 mmol), and triethylamine (1.6 mL, 11.5 mmol) in dioxane (100 mL) was stirred at reflux overnight. The solvent was removed in vacuo and the residue partitioned with ethyl acetate and aqueous sodium bicarbonate. The organic phase was evaporated to a residue which was used without further purification (2.0 g, 91%). $^1$H NMR (500 MHz, Chloroform-d) δ 8.07 (d, J=9.9 Hz, 1H), 7.15 (d, J=8.1 Hz, 1H), 7.03 (dd, J=8.0, 2.1 Hz, 1H), 7.00 (d, J=2.2 Hz, 1H), 6.93 (dq, J=5.5, 2.9 Hz, 2H), 3.96 (s, 3H), 3.62-3.56 (m, 4H), 3.09-3.02 (m, 4H), 2.32 (s, 3H). LRMS (ESI+ve): Calculated for $C_{19}H_{20}ClN_3O_4$, [M+H]=390.12, observed [M+H]=390.01.

Example 36

PRM0208-48-2. Methyl 2-amino-5-(4-(5-chloro-2-methylphenyl)piperazin-1-yl)benzoate was synthesized. A solution of methyl 5-(4-(5-chloro-2-methylphenyl)piperazin-1-yl)-2-nitrobenzoate (2.0 g, 5.13 mmol) in acetic acid (80 mL) was treated with powdered zinc (2.1 g, 32 mmol) portionwise over 10 minutes to control the exothermic reaction. The mixture stirred for 1 hour, filtered, and evaporated to provide an oil which was partitioned with ethyl acetate and aqueous sodium bicarbonate. The organic phase was evaporated to a brown oil which was used without further purification (1.74 g, 86%). $^1$H NMR (500 MHz, Chloroform-d) δ 7.50 (d, J=2.9 Hz, 1H), 7.13 (t, J=7.2 Hz, 2H), 7.04 (d, J=2.2 Hz, 1H), 7.02-6.97 (m, 1H), 6.70 (dd, J=8.8, 1.7 Hz, 1H), 5.50 (s, 2H), 3.91 (d, J=1.8 Hz, 3H), 3.21 (t, J=4.5 Hz, 4H), 3.09 (d, J=4.6 Hz, 4H), 2.31 (d, J=1.6 Hz, 3H). LRMS (ESI+ve): Calculated for $C_{19}H_{22}ClN_3O_2$, [M+H]=360.15, observed [M+H]=360.46.

Example 37

The following reaction pathway was employed.

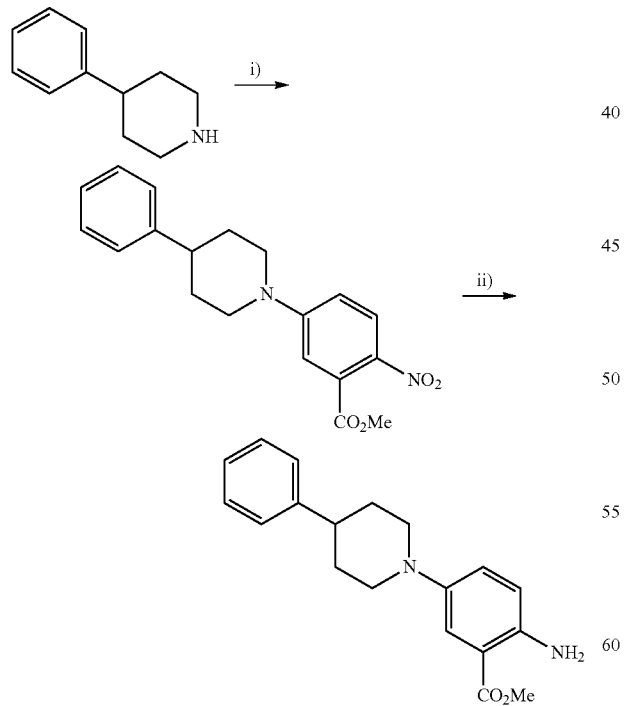

Reagents: i) methyl 2-nitro-5-fluoro benzoate, K$_2$CO$_3$, MeCN, reflux; ii) Zn, HOAc PRM0208-65-1. Methyl 2-nitro-5-(4-phenylpiperidin-1-yl)benzoate was synthesized. A solution of 4-phenylpiperidine (196 mg, 1.21 mmol), methyl 5-fluoro-2-nitrobenzoate (242 mg, 1.21 mmol), and potassium carbonate (170 mg, 1.23 mmol) in acetonitrile (12 mL) was stirred at reflux overnight. The solvent was removed in vacuo and the residue was triturated with dichloromethane. The insolubles were filtered and the solvent evaporated to provide a yellow solid which was used without further purification (410 mg, 99%). $^1$H NMR (500 MHz, Chloroform-d) δ 8.09-8.03 (m, 1H), 7.39-7.32 (m, 2H), 7.31-7.21 (m, 3H), 6.91 (d, J=10.5 Hz, 2H), 4.16-4.07 (m, 2H), 3.96 (d, J=2.1 Hz, 3H), 3.18-3.07 (m, 2H), 2.83 (tt, J=12.2, 3.5 Hz, 1H), 2.07-1.96 (m, 2H), 1.82 (qd, J=12.8, 3.8 Hz, 2H). LRMS (ESI+ve): Calculated for $C_{15}H_{20}N_2O_4$, [M+H]=341.15, observed [M+H]=341.45.

Example 38

PRM0208-65-2. Methyl 2-amino-5-(4-phenylpiperidin-1-yl)benzoate was synthesized. A solution of methyl 2-nitro-5-(4-phenylpiperidin-1-yl)benzoate (410 mg, 1.2 mmol) in acetic acid (10 mL) was treated with powdered zinc (400 mg, 6.1 mmol) portionwise over 10 minutes to control the exothermic reaction. The mixture stirred for 2 hours, filtered, and evaporated to provide an oil which was partitioned with ethyl acetate and aqueous potassium carbonate. The organic phase was evaporated to a residue which was used without further purification (369 mg, 98%). $^1$H NMR (500 MHz, Chloroform-d) δ 7.50 (d, J=2.9 Hz, 1H), 7.35 (dd, J=7.9, 7.1 Hz, 2H), 7.30 (dd, J=7.4, 1.6 Hz, 2H), 7.27-7.21 (m, 1H), 7.14 (dd, J=8.8, 2.9 Hz, 1H), 6.68 (d, J=8.9 Hz, 1H), 5.45 (s, 2H), 3.90 (s, 3H), 3.59 (d, J=11.9 Hz, 2H), 2.75 (td, J=11.5, 3.9 Hz, 2H), 2.63 (tt, J=10.4, 5.0 Hz, 1H), 1.98 (dp, J=11.7, 4.3 Hz, 4H). LRMS (ESI+ve): Calculated for $C_{19}H_{22}N_2O_2$, [M+H]=311.18, observed [M+H]=311.48.

Example 39

The following reaction pathway was employed.

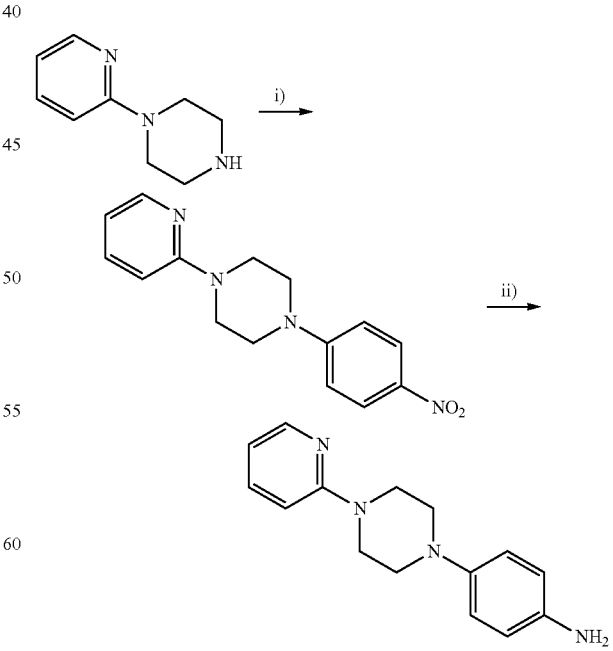

Reagents: i) 4-fluoro nitrobenzene, Et$_3$N, 1,4-dioxane, reflux; ii) Zn, HOAc

PRM0208-63-1a. 1-(4-Nitrophenyl)-4-(pyridin-2-yl)piperazine was synthesized. A solution of 1-(pyridin-2-yl)piperazine (900 mg, 6.8 mmol), 1-fluoro-4-nitrobenzene (960 mg, 6.8 mmol), and potassium carbonate (1.24 g, 6.8 mmol) in acetonitrile (30 mL) was stirred at reflux overnight. The solvent was removed in vacuo and the residue was triturated with 10% methanol in dichloromethane. The insolubles were filtered and the solvent evaporated to provide a yellow solid which was then triturated with hexanes. The product was collected by filtration (1.2 g, 76%). $^1$H NMR (500 MHz, Chloroform-d) δ 8.27-8.22 (m, 1H), 8.18 (d, J=9.4 Hz, 2H), 7.55 (ddd, J=8.8, 7.2, 2.1 Hz, 1H), 6.91-6.84 (m, 2H), 6.74-6.67 (m, 2H), 3.81-3.75 (m, 4H), 3.62 (td, J=5.1, 2.4 Hz, 4H). LRMS (ESI+ve): Calculated for $C_{15}H_{16}N_4O_2$, [M+H]=285.14, observed [M+H]=285.07.

Example 40

PRM0208-63-2. 4-(4-(Pyridin-2-yl)piperazin-1-yl)aniline was synthesized. A solution of 1-(4-nitrophenyl)-4-(pyridin-2-yl)piperazine (1.2 g, 1.2 mmol) in acetic acid (15 mL) was treated with powdered zinc (1.1 g, 16.8 mmol) portionwise over 10 minutes to control the exothermic reaction. The mixture stirred for 1 hour, filtered, and evaporated to provide an oil which was partitioned with ethyl acetate and aqueous potassium carbonate. The organic phase was evaporated to a residue which was used without further purification (1.05 g, 98%). $^1$H NMR (500 MHz, Chloroform-d) δ 8.24 (dd, J=4.9, 2.1 Hz, 1H), 7.55-7.49 (m, 1H), 6.92-6.85 (m, 2H), 6.69 (ddd, J=16.9, 12.6, 8.0 Hz, 4H), 3.71 (t, J=5.0 Hz, 4H), 3.48 (s, 2H), 3.17 (t, J=5.0 Hz, 4H). LRMS (ESI+ve): Calculated for $C_{15}H_{18}N_4$, [M+H]=255.16, observed [M+H]=255.14.

Example 41

The following reaction pathway was employed.

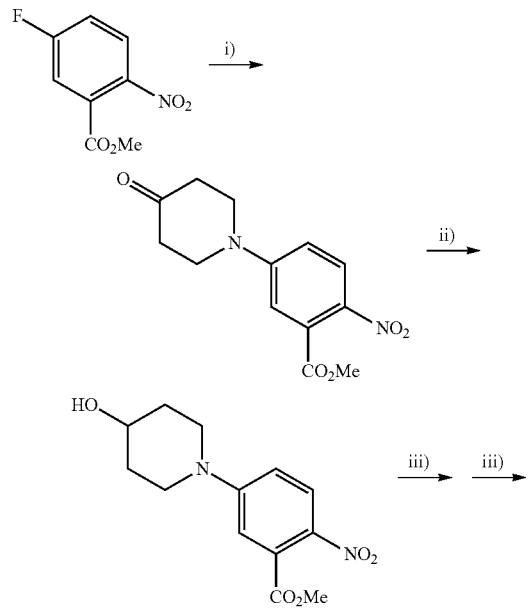

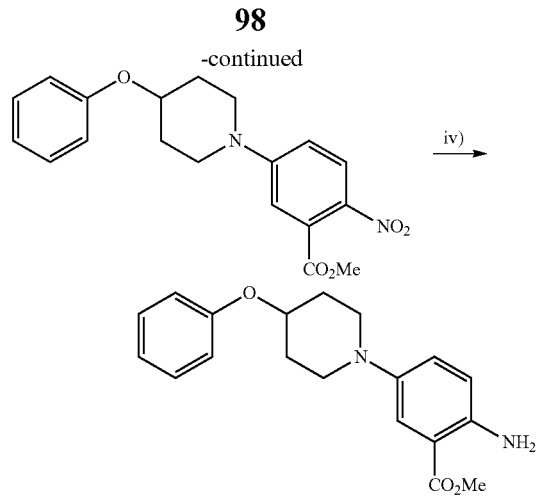

Reagents: i) 4-piperidinone hydrochloride, Et$_3$N, 1,4-dioxane, reflux; ii) NaBH$_4$, MeOH; iii) phenol, P(Ph)$_3$, DIAD; iv) Zn, HOAc PRM0208-072-1. Methyl 2-nitro-5-(4-oxopiperidin-1-yl)benzoate was synthesized. A solution of methyl 5-fluoro-2-nitrobenzoate (500 mg, 2.5 mmol), piperidin-4-one hydrochloride (400 mg, 2.6 mmol), and triethylamine (0.8 mL, 5.7 mmol) in acetonitrile (15 mL) was stirred at reflux overnight. The solvent was removed in vacuo and the residue partitioned with ethyl acetate and water. The organic phase was evaporated to a yellow solid which was used without further purification (647 mg, 93%). $^1$H NMR (500 MHz, Chloroform-d) δ 8.12-8.07 (m, 1H), 6.91 (d, J=2.9 Hz, 1H), 6.89 (s, 1H), 3.96 (s, 3H), 3.84 (t, J=6.2 Hz, 4H), 2.66 (t, J=6.2 Hz, 4H). LRMS (ESI+ve): Calculated for $C_{13}H_{14}N_2O_5$, [M+H]=279.10, observed [M+H]=279.31.

Example 42

PRM0208-073-1. Methyl 5-(4-hydroxypiperidin-1-yl)-2-nitrobenzoate was synthesized. A solution of methyl 2-nitro-5-(4-oxopiperidin-1-yl)benzoate (106 mg, 0.38 mmol) in methanol (2 mL) was treated with sodium borohydride (38 mg, 1 mmol) and was stirred overnight. Excess reducing agent was quenched with the addition of acetone (1 mL) before the solvents were removed in vacuo. The residue was partitioned with ethyl acetate and aqueous sodium bicarbonate and the organic phase evaporated to provide a yellow oil (105 mg, 99%). $^1$H NMR (500 MHz, Chloroform-d) δ 8.06-8.01 (m, 1H), 6.87 (d, J=2.9 Hz, 1H), 6.85 (d, J=2.5 Hz, 1H), 4.03 (tt, J=7.8, 3.8 Hz, 1H), 3.95 (s, 3H), 3.79 (ddd, J=13.3, 6.8, 3.9 Hz, 2H), 3.29 (ddd, J=13.0, 8.7, 3.5 Hz, 2H), 2.01 (ddd, J=13.4, 7.0, 3.6 Hz, 2H), 1.67 (dtd, J=12.6, 8.3, 3.8 Hz, 2H), 1.60 (s, 2H). LRMS (ESI+ve): Calculated for $C_{13}H_{16}N_2O_5$, [M+H]=281.11, observed [M+H]=281.38.

Example 43

PRM0208-073-2a. Methyl 2-nitro-5-(4-phenoxypiperidin-1-yl)benzoate was synthesized. A solution of methyl 5-(4-hydroxypiperidin-1-yl)-2-nitrobenzoate (105 mg, 0.38 mmol), triphenylphosphine (100 mg, 0.38 mmol), and phenol (37 mg, 0.39 mmol) in DMF (6 mL) was treated with DIAD (0.75 mL, 0.38 mmol). The reaction stirred overnight then was evaporated to a residue which was purified on silica gel eluting with dichloromethane (114 mg, 84%). $^1$H NMR (500 MHz, Chloroform-d) δ 8.05-8.01 (m, 1H), 7.32 (dd, J=8.6, 7.3 Hz, 2H), 7.00 (td, J=7.3, 1.1 Hz, 1H), 6.97-6.93 (m, 2H), 6.90-6.84 (m, 2H), 4.62 (tt, J=6.5, 3.5 Hz, 1H), 3.94

(s, 3H), 3.71 (ddd, J=12.8, 8.6, 3.6 Hz, 2H), 3.49 (ddd, J=13.3, 6.7, 4.0 Hz, 2H), 2.06 (ddt, J=12.6, 8.1, 3.8 Hz, 2H), 1.97 (dtd, J=13.2, 6.4, 3.7 Hz, 2H). LRMS (ESI+ve): Calculated for $C_{19}H_{20}N_2O_5$, [M+H]=357.15, observed [M+H]=357.32.

Example 44

PRM0208-073-3. Methyl 2-amino-5-(4-phenoxypiperidin-1-yl)benzoate was synthesized. A solution of methyl 2-nitro-5-(4-phenoxypiperidin-1-yl)benzoate (114 mg, 0.32 mmol) in acetic acid (4 mL) was treated with powdered zinc (100 mg, 1.52 mmol) portionwise over 10 minutes to control the exothermic reaction. The mixture stirred for 30-60 minutes, filtered, and evaporated to provide an oil which was partitioned with ethyl acetate and aqueous potassium carbonate. The organic phase was evaporated to provide an orange oil which was used without further purification (88 mg, 84%). $^1$H NMR (500 MHz, Chloroform-d) δ 7.48 (d, J=2.8 Hz, 1H), 7.34-7.29 (m, 2H), 7.11 (dt, J=8.9, 1.9 Hz, 1H), 7.00-6.93 (m, 3H), 6.67 (dd, J=8.9, 1.1 Hz, 1H), 5.45 (s, 2H), 4.46 (tt, J=7.5, 3.7 Hz, 1H), 3.89 (d, J=1.2 Hz, 3H), 3.34 (ddd, J=11.3, 7.1, 3.6 Hz, 2H), 2.96 (ddd, J=11.9, 8.2, 3.4 Hz, 2H), 2.14 (dq, J=11.0, 3.6 Hz, 2H), 1.99 (dtd, J=12.0, 7.9, 3.5 Hz, 2H). LRMS (ESI+ve): Calculated for $C_{19}H_{22}N_2O_3$, [M+H]=327.17, observed [M+H]=327.48.

Example 45

The following reaction pathway was employed.

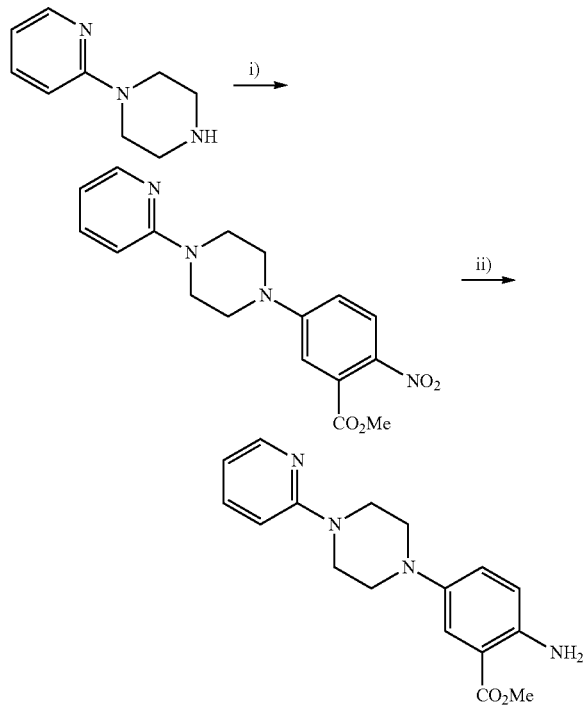

Reagents: i) methyl 2-nitro-5-fluoro benzoate, Et$_3$N, 1,4-dioxane, reflux; ii) Zn, HOAc Methyl 2-nitro-5-(4-(pyridin-2-yl)piperazin-1-yl)benzoate was synthesized. solution of 1-(pyridin-2-yl)piperazine (1 g, 6.1 mmol), methyl 5-fluoro-2-nitrobenzoate (1.28 g, 6.4 mmol), and triethylamine (1.71 mL, 12.3 mmol) in 1,4-dioxane (20 mL) was stirred at room temperature for 5 min. followed by heating at 95° C. overnight. LCMS of aliquot showed complete conversion of starting material. The solvent was evaporated in vacuo and residue partitioned between water and ethyl acetate. The water layer was discarded and organic layer evaporated in vacuo to afford methyl 2-nitro-5-(4-(pyridin-2-yl)piperazin-1-yl)benzoate as an orange solid (2.05 g, 98%). $^1$H NMR (500 MHz, Chloroform-d) δ 8.24 (dd, J=5.0, 2.1 Hz, 1H), 8.12-8.01 (m, 1H), 7.56 (t, J=7.8 Hz, 1H), 6.95-6.85 (m, 2H), 6.77-6.65 (m, 2H), 3.96 (d, J=1.7 Hz, 3H), 3.80-3.75 (m, 4H), 3.64-3.60 (m, 4H); LRMS (ESI+ve): Calculated for $C_{17}H_{18}N_4O_4$, [M+H]=343.14, observed [M+H]=343.25.

Example 46

Methyl 2-amino-5-(4-(pyridin-2-yl)piperazin-1-yl)benzoate was synthesized. A solution of crude methyl 2-nitro-5-(4-(pyridin-2-yl)piperazin-1-yl)benzoate (max 2.05 g, 6.1 mmol) in glacial acetic acid (30 mL) was treated with Zn dust (2.41 g, 36.8 mmol) at rate to avoid setting up an uncontrolled exothermic reaction. The reaction mixture was allowed to stir overnight and quenched by pouring slowly into aq. K$_2$CO$_3$ solution. After adjusting the final pH to ~12.0, the mixture was extracted with ethyl acetate and the solvent was evaporated in vacuo to afford crude methyl 2-amino-5-(4-(pyridin-2-yl)piperazin-1-yl)benzoate as a brown solid (1.6 g, 83%). $^1$H NMR (500 MHz, Chloroform-d) δ 8.34-8.18 (m, 1H), 7.59-7.43 (m, 2H), 7.19-7.03 (m, 1H), 6.78-6.59 (m, 3H), 5.08 (broad s, 2H), 3.90 (s, 3H), 3.76-3.66 (m, 4H), 3.18-3.12 (m, 4H); LRMS (ESI+ve): Calculated for $C_{17}H_{20}N_4O_2$, [M+H]=313.17, observed [M+H]=313.5.

Example 47

The compounds with the highest ECx value at the lowest concentration are the most potent PTI compounds.

For example, in the ANT44 assay an EC48=9 means that the PTI molecule at 9 μM was able to block 48% of the Ant44 entry into L3.6 pl human Pancreatic ductal adenocarcinoma cells after 72 h incubation time at 37° C. Another explanation, is that the PTI was able to disrupt 48% of the intracellular trafficking of Ant44 that leads to toxicity. Recall a polyamine transport inhibitor can work at any one (or more than one) of the different steps involved in the multi-step polyamine import and intracellular trafficking process. Blocking the entering spermidine from reaching its intended intracellular target is another way in which these compounds may function.

In another example in the DFMO spermidine (Spd) rescue assay an EC38=8 means that the PTI molecule at 8 μM was able to block 38% of the entry of spermidine into DFMO treated L3.6pl cells after 72 h incubation time at 37° C. Another explanation, is that the PTI was able to disrupt 48% of the intracellular trafficking of Spd that leads to cell rescue. By inhibiting spermidine's proper trafficking, these compounds inhibit spermidine from rescuing the cell from DFMO-induced poylamine depletion. Since both Ant44 and Spermidine are polyamine-based systems, cells likely use one mode of the polyamine transport (basal or obligate) in each assay.

As seen in Table 8A, 8B 9, there were some compounds that performed well in one assay and not the other, i.e., a high ECx value in one but not the other assay. There were also compounds which behaved as pan inhibitors, which blocked both modes of polyamine transport and gave similar high ECx values in both assays.

Table 8A lists structures referenced in Table 8B.

TABLE 8A

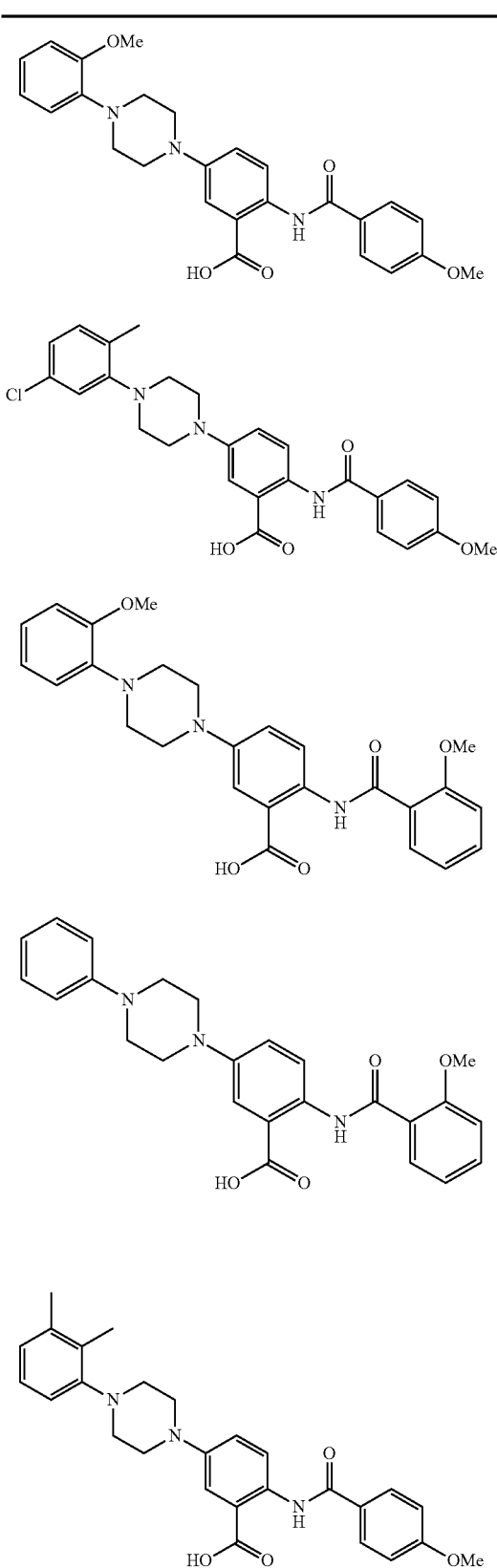

TABLE 8A-continued

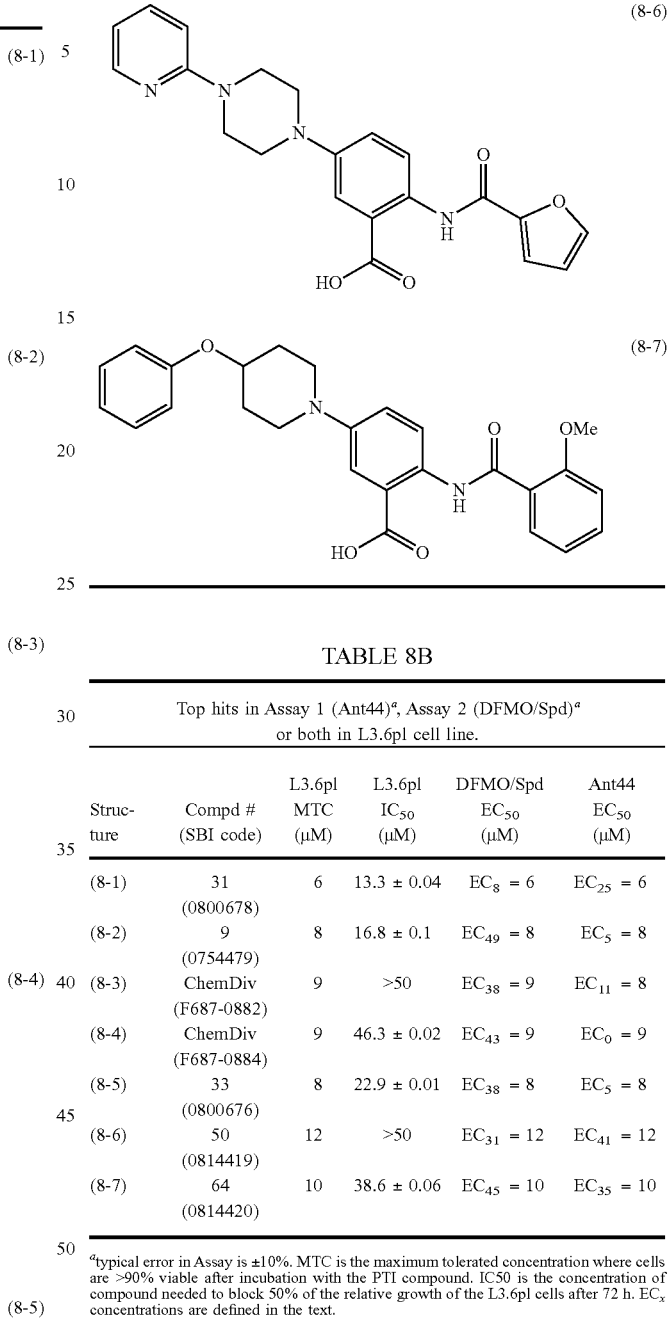

TABLE 8B

Top hits in Assay 1 (Ant44)[a], Assay 2 (DFMO/Spd)[a] or both in L3.6pl cell line.

| Structure | Compd # (SBI code) | L3.6pl MTC (µM) | L3.6pl IC$_{50}$ (µM) | DFMO/Spd EC$_{50}$ (µM) | Ant44 EC$_{50}$ (µM) |
|---|---|---|---|---|---|
| (8-1) | 31 (0800678) | 6 | 13.3 ± 0.04 | EC$_8$ = 6 | EC$_{25}$ = 6 |
| (8-2) | 9 (0754479) | 8 | 16.8 ± 0.1 | EC$_{49}$ = 8 | EC$_5$ = 8 |
| (8-3) | ChemDiv (F687-0882) | 9 | >50 | EC$_{38}$ = 9 | EC$_{11}$ = 8 |
| (8-4) | ChemDiv (F687-0884) | 9 | 46.3 ± 0.02 | EC$_{43}$ = 9 | EC$_0$ = 9 |
| (8-5) | 33 (0800676) | 8 | 22.9 ± 0.01 | EC$_{38}$ = 8 | EC$_5$ = 8 |
| (8-6) | 50 (0814419) | 12 | >50 | EC$_{31}$ = 12 | EC$_{41}$ = 12 |
| (8-7) | 64 (0814420) | 10 | 38.6 ± 0.06 | EC$_{45}$ = 10 | EC$_{35}$ = 10 |

[a]typical error in Assay is ±10%. MTC is the maximum tolerated concentration where cells are >90% viable after incubation with the PTI compound. IC50 is the concentration of compound needed to block 50% of the relative growth of the L3.6pl cells after 72 h. EC$_x$ concentrations are defined in the text.

Compounds 31, 54 and 60 worked in Assay 1. All listed compounds (except 31) worked well in Assay 2 (DEMO). Two compounds (#50, #64) performed in both assays and were deemed pan PTIs and are preferred. In terms of toxicity profiles, compounds ChemDiv F687-0882 and ChemDiv F687-0884 and compounds 50 and 64 gave IC$_{50}$ values>38 µM and were deemed relatively non-toxic. In summary, we have identified specific inhibitors of Ant44 toxicity and spermidine rescue of DEMO treated cells.

Additional compounds were synthesized to better understand the structure activity relationships. As shown in Table 9, some compounds were active in both the Ant44 and DEMO assays and others were active in one assay.

TABLE 9

Additional example hits observed in the DFMO and Ant44 assays in the L3.6pl pancreatic cancer cell line.

| Compound | 72 h IC$_{50}$ (μM) | MTD (μM) | EC value in DFMO/Spd rescue assay | EC value in Ant44 (3 μM) assay |
|---|---|---|---|---|
| [structure: 5-chloro-2-methylphenyl piperazine linked to benzene with COOH and NH-C(O)-(4-methoxyphenyl)] | 16.8 ± 0.1 | 8 μM | EC$_{49}$ = 8 μM | EC$_{21}$ = 8 μM |
| [structure: 5-chloro-2-methylphenyl piperazine linked to benzene with COOH and NH-C(O)-(2,4-dimethoxyphenyl)] | >50 μM | >20 μM | EC$_{15}$ = 20 μM | inactive |
| [structure: 5-chloro-2-methylphenyl piperazine linked to benzene with COOH and NH-C(O)-(2-methoxyphenyl)] | 29.1 ± 0.03 | >5 μM | EC$_{29}$ = 5 μM | not working as a PTI |
| [structure: 4-phenoxypiperidine linked to benzene with COOH and NH-C(O)-benzofuran-2-yl] | 44.4 ± 0.04 μM | 10 μM | EC$_{30}$ = 10 μM | EC$_{7}$ = 10 μM |
| [structure: 4-phenoxypiperidine linked to benzene with COOH and NH-C(O)-indol-2-yl] | 38.3 ± 0.04 μM | 10 μM | EC$_{30}$ = 9 μM | not working as a PTI |

TABLE 9-continued

Additional example hits observed in the DFMO and Ant44 assays in the L3.6pl pancreatic cancer cell line.

| Compound | 72 h IC$_{50}$ (μM) | MTD (μM) | EC value in DFMO/Spd rescue assay | EC value in Ant44 (3 μM) assay |
|---|---|---|---|---|
| [HCl salt; piperazine-phenyl-furan-2-carboxamide benzoic acid structure] | Not toxic up to 50 μM | 40 μM | EC$_{10}$ = 40 μM | EC$_{22}$ = 40 μM |
| [4-phenoxypiperidine-phenyl-nicotinamide benzoic acid structure] | Not toxic up to 50 μM | 10 μM | EC$_{25}$ = 8 μM | Not working |
| [4-phenoxypiperidine-phenyl-(5-(4-chlorophenyl)furan-2-carboxamide) benzoic acid structure] | Not toxic up to 1 uM | 1 μM | EC$_6$ = 1 μM | Not working |
| [4-fluoro-phenyl-furan-2-carboxamide benzoic acid structure] | Not toxic up to 100 μM | >100 μM | EC$_{67}$ = 100 μM | EC$_{36}$ = 50 μM |

The higher EC value denotes the compound is giving a relative % growth of L3.6 pl cells consistent with inhibiting either Ant44 uptake or blocking the uptake of the rescuing dose of spermidine. Alternatively these compounds may disrupting the intracellular trafficking of Ant44 and spermidine so they cannot reach their intended intracellular target.

Table 10 shows experimental data pertaining to select synthesized compounds.

TABLE 10

Experimental data for select compounds

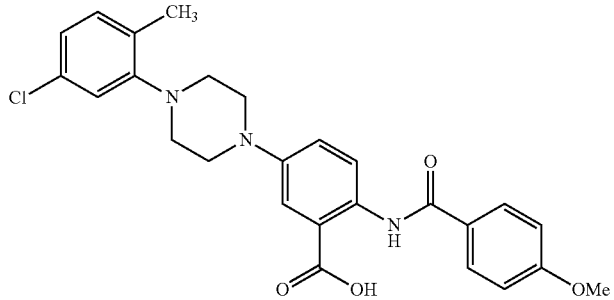 [SMILES: COc1ccc(C(=O)Nc2ccc(N3CCN(c4cc(Cl)ccc4C)CC3)cc2C(=O)O)cc1]

Light yellow solid (81%), $^1$H NMR (400 MHz, DMSO-d$_6$) δ 8.59 (d, J = 8.9 Hz, 1H), 7.97 (d, J = 8.7 Hz, 2H), 7.72 (d, J = 3.0 Hz, 1H), 7.20 (d, J = 8.1 Hz, 1H), 7.09-7.01 (m, 5H), 3.82 (s, 3H), 3.27-3.21 (m, 4H), 3.05-2.98 (m, 4H), 2.26 (s, 3H); $^{13}$C NMR (100 MHz, DMSO-d$_6$) δ 171.2, 163.9, 162.4, 153.4, 146.3, 134.9, 133.0, 131.5, 131.4, 129.6, 128.7, 125.3, 123.3, 120.2, 119.7, 119.2, 119.1, 114.6, 56.1, 51.9, 50.2, 18.0; HRMS (ESI) calcd for C$_{26}$H$_{27}$ClN$_3$O$_4$ [M + H]$^+$ 480.1690, found 480.1702.

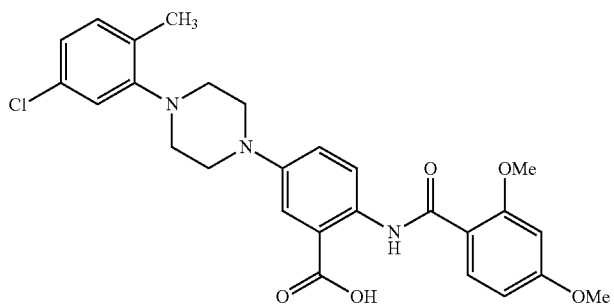 [SMILES: COc1ccc(C(=O)Nc2ccc(N3CCN(c4cc(Cl)ccc4C)CC3)cc2C(=O)O)c(OC)c1]

Off white solid (82%), $^1$H NMR (400 MHz, DMSO-d$_6$) δ 8.64 (d, J = 9.1 Hz, 1H), 7.84 (d, J = 9.1 Hz, 1H), 7.68 (s, 1H), 7.19 (d, J = 7.9 Hz, 1H), 7.08 (dd, J = 9.0, 2.7 Hz, 1H), 7.02 (d, J = 7.4 Hz, 2H), 6.68-6.59 (m, 2H), 3.93 (s, 3H), 3.82 (s, 3H), 3.23 (s, 4H), 2.99 (s, 4H), 2.24 (s, 3H); $^{13}$C NMR (100 MHz, DMSO-d$_6$) δ 163.6, 163.5, 159.3, 153.3, 146.3, 134.1, 133.2, 133.0, 131.5, 131.4, 123.3, 121.9, 119.7, 119.5, 119.4, 118.6, 118.6, 117.3, 106.3, 98.9, 56.4, 56.2, 51.9, 50.0, 18.0; HRMS (ESI) calcd for C$_{27}$H$_{29}$ClN$_3$O$_5$ [M + H]$^+$ 510.1796, found 510.1808.

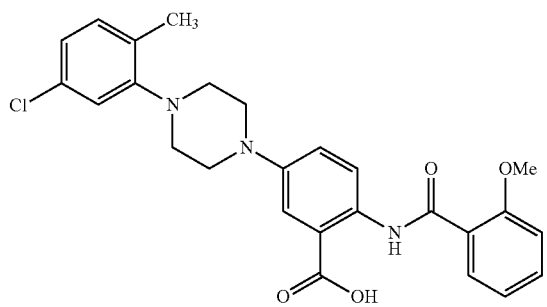 [SMILES: COc1ccccc1C(=O)Nc1ccc(N2CCN(c3cc(Cl)ccc3C)CC2)cc1C(=O)O]

Off white solid (87%), $^1$H NMR (400 MHz, DMSO-d$_6$) δ 8.60 (d, J = 9.0 Hz, 1H), 7.74-7.66 (m, 2H), 7.48-7.46 (m, 1H), 7.20 (d, J = 8.0 Hz, 1H), 7.13 (d, J = 8.0 Hz, 1H), 7.08-7.00 (m, 4H), 3.88 (s,3H), 3.28-3.21 (m, 4H), 3.06-2.98 (m, 4H), 2.26 (s, 3H); $^{13}$C NMR (100 MHz, DMSO-d$_6$) δ 170.9, 164.1, 157.5, 153.4, 146.4, 134.2, 133.0, 132.5, 131.5, 131.4, 130.8, 126.4, 126.3, 123.3, 121.0, 119.7, 118.9, 118.7, 112.7, 56.4, 51.9, 50.2, 18.0; HRMS (ESI) calcd for C$_{26}$H$_{27}$ClN$_3$O$_4$ [M + H]$^+$ 480.1690, found 480.1695.

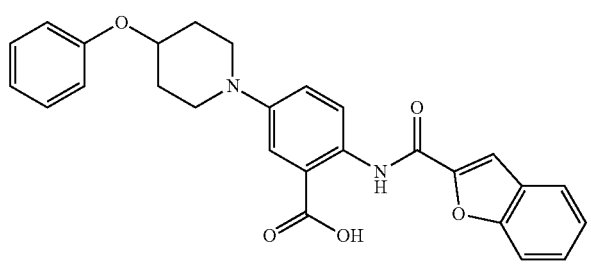 [SMILES: O=C(Nc1ccc(N2CCC(Oc3ccccc3)CC2)cc1C(=O)O)c1cc2ccccc2o1]

$^1$H NMR (400 MHz, DMSO-d$_6$) δ 7.64 (t, J = 6.7 Hz, 3H), 7.50 (d, J = 4.0 Hz, 2H), 7.28-7.21 (m, 3H), 7.18 (s, 1H), 7.04 (s, 1H), 6.95-6.87 (m, 3H), 4.38 (s, 1H), 3.51-3.39 (m, 2H), 3.34-3.23 (m, 2H), 2.33-2.23 (m, 2H), 2.04-1.93 (m, 2H); $^{13}$C NMR (100 MHz, DMSO-d$_6$) δ 157.8, 156.1, 155.2, 151.0, 146.8, 133.5, 130.3, 130.1, 128.2, 127.4, 124.4, 123.4, 121.4, 120.4, 119.5, 119.4, 116.7, 116.1, 112.6, 109.9, 72.8, 47.4, 31.1; HRMS (ESI) calcd for C$_{27}$H$_{25}$N$_2$O$_5$ [M + H]$^+$ 457.1763, found 457.1735.

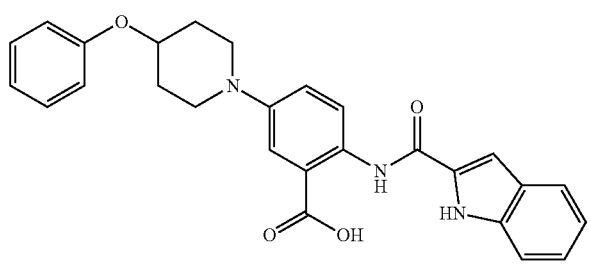

$^1$H NMR (400 MHz, DMSO-d$_6$) δ 11.69 (s, 1H), 8.50 (d, J = 9.0 Hz, 1H), 7.66 (d, J = 3.0 Hz,1H), 7.59 (d, J = 7.8 Hz, 1H), 7.42 (d, J = 8.2 Hz, 1H), 7.33-7.21 (m, 2H), 7.17-7.13 (m, 1H), 7.11-7.03 (m, 2H), 7.03-6.99 (m, 1H), 6.95 (dd, J = 8.7, 1.0 Hz, 2H), 6.92-6.84 (m, 1H), 4.58-4.46 (m, 1H), 3.49-3.40 (m, 2H), 3.06-2.93 (m, 2H), 2.05-2.02 (m, 2H), 1.80-1.66 (m, 2H); $^{13}$C NMR (100 MHz, DMSO-d$_6$) δ 168.5, 161.9, 159.3, 157.8, 146.5, 137.6, 134.2, 133.9, 130.3, 128.0, 124.1, 122.2, 121.4, 120.6, 120.2, 120.1, 119.4, 116.7, 113.2, 102.7, 72.7, 47.5, 31.1; HRMS (ESI) calcd for C$_{27}$H$_{26}$N$_3$O$_4$ [M + H]$^+$ 456.1923, found 456.1915.

TABLE 10-continued

Experimental data for select compounds

| Structure | NMR Data |
|---|---|
| 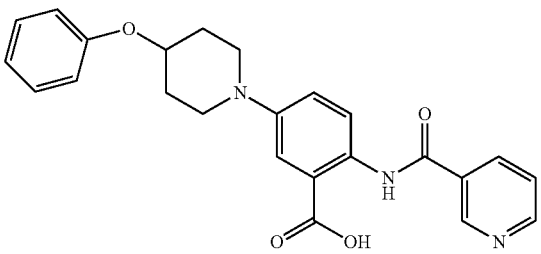 [SMILES: O=C(Nc1ccc(N2CCC(Oc3ccccc3)CC2)cc1C(=O)O)c1cccnc1] | ¹H NMR (400 MHz, DMSO-$d_6$) δ 11.87 (s, 1H), 9.53 (s, 2H), 8.55 (d, J = 9.2 Hz, 1H), 7.97 (dd, J =1.7,0.8 Hz, 1H), 7.58 (d, J = 3.0 Hz, 1H), 7.36 (dd, J = 9.2, 3.0 Hz, 1H), 7.23 (dd, J = 3.5, 0.7 Hz, 1H), 6.73 (dd, J = 3.5, 1.7 Hz, 1H), 3.44-3.34 (m, 4H), 3.22 (s, 4H); ¹³C NMR (100 MHz, DMSO-$d_6$) δ 169.9, 155.9, 148.1, 146.4, 145.8, 134.1, 122.9, 121.6, 118.2, 117.8, 115.5, 113.1, 46.2, 42.9. |
|  | ¹H NMR (500 MHz, DMSO-$d_6$) δ 11.84 (s, 1H), 9.11 (s, 1H), 8.80 (s, 1H), 8.44 (d, J = 9.1 Hz, 1H), 8.27 (d, J = 8.1 Hz, 1H), 7.61 (dd, J = 7.8, 4.8 Hz, 1H), 7.57 (d, J = 3.0 Hz, 1H), 7.33 (dd, J = 9.2, 3.0 Hz, 1H), 7.29 (dd, J = 8.6, 7.4 Hz, 2H), 6.99 (d, J = 7.8 Hz, 2H), 6.93 (t, J = 7.3 Hz, 1H), 4.63-4.53 (m, 1H), 3.56-3.48 (m, 2H), 3.13-3.04 (m, 2H), 2.09-2.07 (m, 2H), 1.81-1.70 (m, 2H); ¹³C NMR (125 MHz, DMSO-$d_6$) δ 170.3, 163.1, 157.5, 152.8, 148.5, 147.2, 135.2, 132.6, 130.9, 130.0, 124.4, 122.4, 122.2, 121.1, 119.3, 117.7, 116.4, 72.1, 46.6, 30.5. |
| 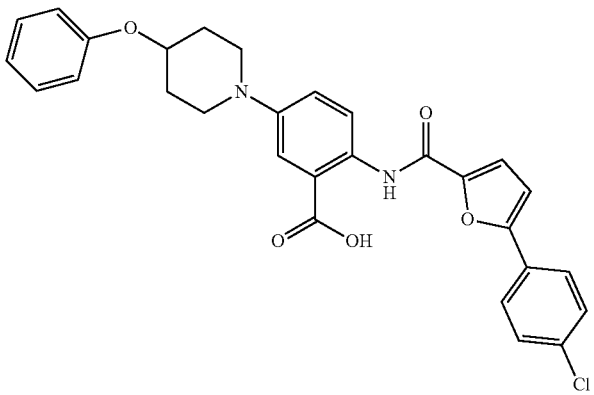 [SMILES: O=C(Nc1ccc(N2CCC(Oc3ccccc3)CC2)cc1C(=O)O)c1ccc(-c2ccc(Cl)cc2)o1] | ¹H NMR (400 MHz, DMSO-$d_6$) δ 8.58 (d, J = 9.2 Hz, 1H), 7.91 (d, J = 8.5 Hz, 2H), 7.59-7.54 (m, 3H), 7.34-7.26 (m, 5H), 7.05-6.89 (m, 3H), 4.63-4.51 (m, 1H), 3.59-3.47 (m, 2H), 3.07 (t, J = 9.3 Hz, 2H), 2.08-2.05 (m, 2H), 1.82-1.67 (m, 2H); ¹³C NMR (100 MHz, DMSO-$d_6$) δ 170.5, 157.5, 155.4, 154.1, 147.6, 146.8, 133.8, 133.0, 130.0, 129.6, 128.5, 126.3, 122.7, 121.3, 121.1, 117.8, 117.5, 116.4, 109.6, 72.1, 46.6, 30.5. |
| 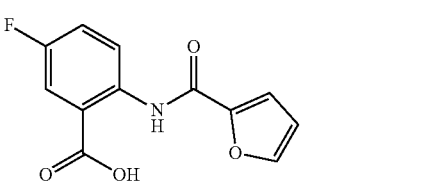 [SMILES: O=C(Nc1ccc(F)cc1C(=O)O)c1ccco1] | ¹H NMR (500 MHz, DMSO-$d_6$) δ 8.68 (dd, J = 9.3, 5.2 Hz, 1H), 7.99 (dd, J = 1.7, 0.8 Hz, 1H), 7.76 (dd, J = 9.3, 3.2 Hz, 1H), 7.57-7.53 (m, 1H), 7.28 (dd, J = 3.5, 0.8 Hz, 1H), 6.75 (dd, J = 3.5, 1.7 Hz, 1H); ¹³C NMR (125 MHz, DMSO-$d_6$) δ 169.0, 168.9, 158.3, 156.4, 156.2, 147.8, 146.7, 137.5, 137.4, 122.5, 122.4, 121.7, 121.5, 118.8, 118.7, 117.6, 117.4, 116.0, 113.2. |

Although the present invention has been described in considerable detail with reference to certain preferred versions thereof, other versions are possible. Therefore, the spirit and scope of the appended claims should not be limited to the description of the preferred versions contained herein.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C § 112, sixth paragraph. In particular, the use of "step of" in the claims herein is not intended to invoke the provisions of 35 U.S.C § 112, sixth paragraph.

REFERENCES

1. Massaro, C.; Thomas, J.; Phanstiel, O., Investigation of Polyamine Metabolism and Homeostasis in Pancreatic Cancers. Med Sci (Basel) 2017, 5 (4).
2. Muth, A.; Madan, M.; Archer, J. J.; Ocampo, N.; Rodriguez, L.; Phanstiel, O., Polyamine transport inhibitors: design, synthesis, and combination therapies with difluoromethylornithine. J Med Chem 2014, 57 (2), 348-363.
3. Meyskens, F. L., Jr.; Gerner, E. W., Development of difluoromethylornithine (DFMO) as a chemoprevention agent. Clin Cancer Res 1999, 5 (5), 945-951.

4. Meyskens, F. L.; Kingsley, E. M.; Glattke, T.; Loescher, L.; Booth, A., A phase II study of alpha-difluoromethylornithine (DFMO) for the treatment of metastatic melanoma. Investigational new drugs 1986, 4 (3), 257-262.
5. Raul, F., Revival of 2-(difluoromethyl)ornithine (DFMO), an inhibitor of polyamine biosynthesis, as a cancer chemopreventive agent. Biochem Soc Trans 2007, 35 (Pt 2), 353-355.
6. Burns, M. R.; Graminski, G. F.; Weeks, R. S.; Chen, Y.; O'Brien, T. G., Lipophilic lysine-spermine conjugates are potent polyamine transport inhibitors for use in combination with a polyamine biosynthesis inhibitor. J Med Chem 2009, 52 (7), 1983-1993.
7. Chen, Y.; Weeks, R. S.; Burns, M. R.; Boorman, D. W.; Klein-Szanto, A.; O'Brien, T. G., Combination therapy with 2-difluoromethylornithine and a polyamine transport inhibitor against murine squamous cell carcinoma. Int J Cancer 2006, 118 (9), 2344-2349.
8. Graminski, G. F.; Carlson, C. L.; Ziemer, J. R.; Cai, F.; Vermeulen, N. M.; Vanderwerf, S. M.; Burns, M. R., Synthesis of bis-spermine dimers that are potent polyamine transport inhibitors. Bioorg Med Chem Lett 2002, 12 (1), 35-40.
9. Hayes, C. S.; Burns, M. R.; Gilmour, S. K., Polyamine blockade promotes antitumor immunity. Oncoimmunology 2014, 3 (1), e27360.
10. Hayes, C. S.; Shicora, A. C.; Keough, M. P.; Snook, A. E.; Burns, M. R.; Gilmour, S. K., Polyamine-blocking therapy reverses immunosuppression in the tumor microenvironment. Cancer Immunology Research 2014, 2 (3), 274-285.
11. Samal, K.; Zhao, P.; Kendzicky, A.; Yco, L. P.; McClung, H.; Gerner, E.; Burns, M.; Bachmann, A. S.; Sholler, G., AMXT-1501, a novel polyamine transport inhibitor, synergizes with DFMO in inhibiting neuroblastoma cell proliferation by targeting both ornithine decarboxylase and polyamine transport. Int J Cancer 2013, 133 (6), 1323-1333.
12. Skorupski, K. A.; O'Brien, T. G.; Guerrero, T.; Rodriguez, C. O.; Burns, M. R., Phase I/II clinical trial of 2-difluoromethyl-ornithine (DFMO) and a novel polyamine transport inhibitor (MQT 1426) for feline oral squamous cell carcinoma. Vet Comp Oncol 2011, 9 (4), 275-282.
13. Weeks, R. S.; Vanderwerf, S. M.; Carlson, C. L.; Burns, M. R.; O'Day, C. L.; Cai, F.; Devens, B. H.; Webb, H. K., Novel lysine-spermine conjugate inhibits polyamine transport and inhibits cell growth when given with DFMO. Exp Cell Res 2000, 261 (1), 293-302.
14. Design of Polyamine Transport Inhibitors as Therapeutics. Otto Phanstiel IV; Jennifer J. Archer, in *Polyamine Drug Discovery*, P. Woster and R. A. Casero, eds., RSC Publishing, 2012. 162-187. ISBN 9781849731904.
15. U.S. Provisional Patent Application 62/097,896, entitled: NON-POLYAMINE-CONTAINING POLYAMINE TRANSPORT INHIBITORS AND USES THEREOF TO TREAT CANCERS AND OTHER DISEASES.
16. Chantal Reigada, Otto Phanstiel IV, Mariana R. Miranda, Claudio A. Pereira. Targeting polyamine transport in *Trypanosoma cruzi*. Eur. J. Med. Chem. 2018, 147,1-6.
17. "$N^1$-Substituent Effects in the Selective Delivery of Polyamine-Conjugates into Cells Containing Active Polyamine Transporters." Gardner, R. A.; Delcros, J-G.; Konate, F.; Breitbeil III, F.; Martin, B.; Sigman, M.; Huang, M.; Phanstiel IV, O. *J. Med. Chem.* 2004, 47, 6055-6069.
18. Structure-activity Investigations of Polyamine-anthracene Conjugates and their Uptake via the Polyamine Transporter. Phanstiel, IV, O.; Kaur, N.; Delcros, J-G. *Amino Acids*, 2007, 33, No. 2, 305-313.
19. A *Drosophila* model to identify polyamine-drug conjugates that target the polyamine transporter in an intact epithelium, Chung Tsen, Mark Iltis, Navneet Kaur, Cynthia Bayer, Jean-Guy Delcros, Laurence von Kalm and Otto Phanstiel IV *J. Med Chem.*, 2008, 51, 324-330.
20. A Comparison of Chloroambucil- and Xylene-containing polyamines leads to improved ligands for accessing the polyamine transporter. Navneet Kaur, Jean-Guy Delcros, and Otto Phanstiel IV. *J. Med. Chem.* 2008, 51, 1393-1401.
21. Designing the Polyamine Pharmacophore: Influence of N-substituents on the transport behavior of polyamine conjugates, Kaur, N.; Delcros, J-G.; Archer, J.; Weagraff, N. Z.; Martin, B.; Phanstiel IV, O. *J. Med. Chem.* 2008, 51, 2551-2560.
22. Design of Polyamine Transport Inhibitors as Therapeutics. Otto Phanstiel IV; Jennifer J. Archer, in *Polyamine Drug Discovery*, P. Woster and R. A. Casero, eds., RSC Publishing, 2012. 162-187. ISBN 9781849731904.
23. Ant 4,4, a polyamine-anthracene conjugate, induces cell death and recovery in human promyelogenous leukemia cells (HL-60). Traquete, R.; Ghani, R. A.; Phanstiel, O.; Wallace, H. M. *Amino Acids* 2013, 44,1193-1203.
24. Anthracene-polyamine conjugates inhibit in vitro proliferation of intraerythrocytic *Plasmodium falciparum* parasites. Niemand, J.; Burger, P.; Verlinden, B.; Reader, J.; Joubert, A.; Kaiser, A.; Louw, A. I.; Kirk, K.; Phanstiel IV, O.; Birkholtz, L-M. *Antimicrobial Agents and Chemotherapy.* 2013, 57, 2874-2877.
25. Putrescine importer PlaP contributes to swarming motility and urolithelial cell invasion in *Proteus mirabilis*. Kurihara, S.; Sakai, Y.; Suzuki, H.; Muth, A.; Phanstiel, O.; Rather, P. N. *J. Biol. Chem.* 2013, 288,15668-15676.
26. Development of Polyamine Transport Ligands with Improved Metabolic Stability and Selectivity against Specific Human Cancers. Aaron Muth, Joseph Kamel, Navneet Kaur, Allyson C. Shicora, Iraimoudi S. Ayene, Susan K. Gilmour, and Otto Phanstiel IV. *J. Med. Chem.* 2013, 56, 5819-5828.
27. Polyamine transport inhibitors: Design, Synthesis and Combination therapies with Difluoromethylornithine. Aaron Muth, Jennifer Archer, Nicolette Ocampo, Meenu Madan, Luis Rodriguez, and Otto Phanstiel IV. *J. Med. Chem.* 2014, 57, 348-363.
28. Inhibition of Polyamine Uptake Potentiates the Anti-Proliferative Effect of Polyamine Synthesis Inhibition and Preserves the Contractile Phenotype of Vascular Smooth Muscle Cells. Grossi, M.; Phanstiel, O.; Rippe, K.; Sward, K.; Alajbegovic, A.; Albinsson, S.; Forte, A.; Persson, L.; Hellstrand, P.; Nilsson, B-O. *J. Cell. Physiol.* 2015, 9999, 1-9.
29. Alexander, E.; Minton, A.; Peters, M.; Phanstiel, O.; Gilmour, S., A Novel Polyamine Blockade Therapy Activates an Anti-Tumor Immune Response. *Oncotarget* 2017, 8, 84140-84152.
30. Minpei Wang, Otto Phanstiel IV, Laurence von Kalm. Evaluation of Polyamine Transport Inhibitors in a Drosophila Epithelial Model Suggests the Existence of Multiple Transport Systems. *Med. Sci.* 2017, 5, 27. doi:10.3390/medsci5040027
31. Gitto, Sarah; Pandey, Veethika; Oyer, Jeremiah; Copik, Alicja; Hogan, Frederick; Phanstiel, Otto; Altomare, Deborah. Difluoromethylornithine Combined with a Polyamine Transport Inhibitor is Effective against Gemcitabine Resistant Pancreatic Cancer. *Mol Pharm.* 2017, in press. http://pubs.acs.org/doi/10.1021/acs.molpharmaceut.7b00718

32. Chelsea Massaro, Jenna Thomas, and Otto Phanstiel IV. Investigation of Polyamine Metabolism and Homeostasis in Pancreatic Cancers. *Med Sci.* 2017, 5, 32. doi:10.3390/medsci5040032

33. NON-POLYAMINE-CONTAINING POLYAMINE TRANSPORT INHIBITORS AND USES THEREOF TO TREAT CANCERS AND OTHER DISEASES. Jan. 26, 2015, Appl No. 62/097,896, PTAS #503156356

34. Polyamine Transport Inhibitors as Novel Therapeutics. US-2012-0172449-A1, Pub Date: Jul. 5, 2012.

35. Polyamine Transporter Selective Compounds as Anti-Cancer Agents. Otto Phanstiel, U.S. Pat. No. 8,497,398 (Jul. 30, 2013).

36. Polyamine Transporter Selective Compounds as Anti-cancer agents, Otto Phanstiel, U.S. Patent US-2014-0057989-A1 (Feb. 27, 2014).

37. Polyamine Transport Selective Therapeutic Agents with Enhanced Stability. Otto Phanstiel IV and Aaron Muth, U.S. Patent US2016/0311756 A1, (Oct. 27, 2016).

38. Polyamine Transport Selective Compounds as Anti-Cancer Agents. Otto Phanstiel, U.S. Pat. No. 9,598,351, (Mar. 21, 2017)

39. Mark R. Burns, Gerard F. Graminski, Reitha S. Weeks, Yan Chen, and Thomas G. O'Brien. Lipophilic Lysine-Spermine Conjugates Are Potent Polyamine Transport Inhibitors for Use in Combination with a Polyamine Biosynthesis Inhibitor. *J. Med. Chem.* 2009, 52, 1983-1993.

40. K. A. Skorupski, T. G. O'Brien, T. Guerrero, C. O. Rodriguez and M. R. Burns. Phase 1/II clinical trial of 2-difluoromethylornithine (DFMO) and a novel polyamine transport inhibitor (MQT 1426) for feline oral squamous cell carcinoma. Veterinary and Comparative Oncology. 2011, 9, No. 4, 275-282. DOI: 10.1111/j.1476-5829.2011.00264.x 41. Katherine Samal, Ping Zhao, Ann Kendzicky, Lisette P. Yco, Heather McClung, Eugene Gerner, Mark Burns, Andre S. Bachmann and Giselle Sholler. AMXT-1501, a novel polyamine transport inhibitor, synergizes with DFMO in inhibiting neuroblastoma cell proliferation by targeting both ornithine decarboxylase and polyamine transport. *Int. J. Cancer,* 2013, 133, 1323-1334.

42. John R. Lewis; Thomas G. O'Brien; Katherine A. Skorupski; Erika L. Krick; Alexander M. Reiter.; Michael W. Jennings; Carrie H. Jurney; Shofer F S; Karin U. Sorenmo. Polyamine Inhibitors for Treatment of Feline Oral Squamous Cell Carcinoma: A Proof-of-Concept Study. J Vet Dent 2013, 30, No. 3, 140-145.

43. Gerard F. Graminski, C. Lance Carlson, Josh R. Ziemer, Feng Cai, Nicolaas M. J. Vermeulen, Scott M. Vanderwerf and Mark R. Burns. Synthesis of Bis-Spermine Dimers that are Potent 44. Polyamine Transport Inhibitors. *Bioorganic & Medicinal Chemistry Letters* 2002, 12, 35-40.

45. Yan Chen, Reitha S. Weeks, Mark R. Burns, David W. Boorman, Andres Klein-Szanto and Thomas G. O'Brien. Combination therapy with 2-difluoromethylornithine and a polyamine transport inhibitor against murine squamous cell carcinoma. *Int. J. Cancer* 2006, 118, 2344-2349.

46. Mark R. Burns, C. Lance Carlson, Scott M. Vanderwerf, Josh R. Ziemer, Reitha S. Weeks, Feng Cai, Heather K. Webb, and Gerard F. Graminski. Amino Acid/Spermine Conjugates: Polyamine Amides as Potent Spermidine Uptake Inhibitors. *J. Med. Chem.* 2001, 44, 3632-3644.

47. Richard Poulin, Marie Audette, Rene Charest-Gaudrealt. Polyamine transport Inhibitors. U.S. Pat. No. 6,949,679 B1. Issued Sep. 27, 2005

What is claimed is:

1. A method for treating pancreatic cancer in a subject, the method comprising administering to a subject in need thereof a composition comprising a therapeutically effective amount of compound having the structure:

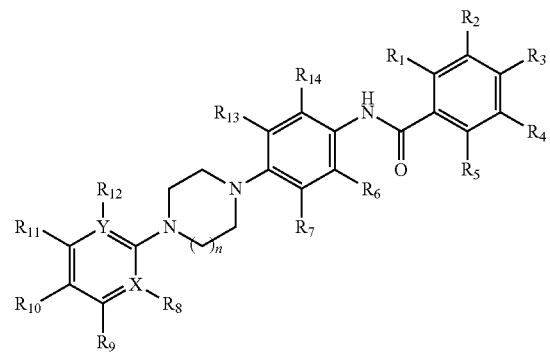

wherein:

n is selected from 1 and 2;

X is selected from C and N;

Y is selected from C and N;

$R_1$ is selected from H, Cl, Me, and OMe;

$R_2$ is selected from H and Me;

$R_3$ is selected from H, F, Me, and OMe;

$R_4$ is selected from H and Me;

$R_5$ is selected from H, Cl, Me, and OMe;

$R_6$ is selected from H and COOH;

$R_7$ is selected from H and COOH;

$R_8$ is selected from a lone pair of electrons, H, Cl, Me, OMe, OEt, OH, and $CH_2OH$;

$R_9$ is selected from H, Cl and Me;

$R_{10}$ is selected from H, OH, F, OMe, and COMe;

$R_{11}$ is selected from H, Cl, and Me;

$R_{12}$ is selected from a lone pair of electrons, H, Cl, Me, OMe, OEt, OH, and $CH_2OH$;

$R_{13}$ is selected from H and COOH; and $R_{14}$ is selected from H and COOH;

or an analog, a derivative, a prodrug, or a pharmaceutically acceptable salt thereof, wherein at least one of $R_1$, $R_3$, or $R_5$ is OMe, and either $R_6$ or $R_7$ is COOH;

and a pharmaceutically acceptable carrier.

2. The method of claim 1, further comprising administering a cytotoxic chemotherapeutic agent to the subject in conjunction with the composition.

3. The method of claim 1, further comprising administering an ornithine decarboxylase inhibitor to the subject.

4. The method according to claim 3, wherein the ornithine decarboxylase inhibitor is difluoromethylornithine (DFMO).

5. The method of claim 3, further comprising administering a cytotoxic chemotherapeutic agent to the subject in conjunction with the composition.

6. The method according to claim 1, wherein the compound has the structure:

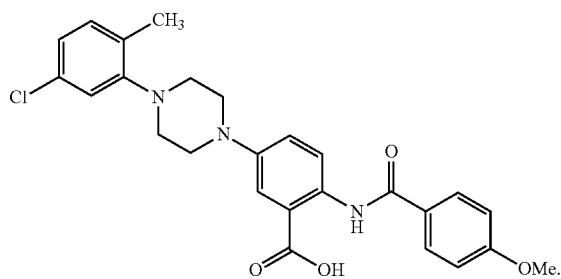

7. The method according to claim 1, wherein the compound has the structure:

2a

8. The method according to claim 1, wherein the compound has the structure:

* * * * *